United States Patent
Smith et al.

(10) Patent No.: US 11,261,193 B2
(45) Date of Patent: Mar. 1, 2022

(54) MORPHIC FORMS OF G1T38 AND METHODS OF MANUFACTURE THEREOF

(71) Applicant: G1 Therapeutics, Inc., Research Triangle Park, NC (US)

(72) Inventors: Alexander Smith, Apex, NC (US); Hannah S. White, Chapel Hill, NC (US); Patricia Andres, Bend, OR (US); Xufeng Sun, Albany, NY (US); Lei Zhu, Schenectady, NY (US); Petinka I. Vlahova, West Lafayette, IN (US)

(73) Assignee: GI Therapeutics, Inc., Research Triangle Park, NC (US)

( * ) Notice: Subject to any disclaimer, the term of this patent is extended or adjusted under 35 U.S.C. 154(b) by 0 days.

(21) Appl. No.: 16/721,631

(22) Filed: Dec. 19, 2019

(65) Prior Publication Data

US 2020/0123168 A1    Apr. 23, 2020

Related U.S. Application Data

(63) Continuation of application No. PCT/US2018/040435, filed on Jun. 29, 2018.

(60) Provisional application No. 62/526,937, filed on Jun. 29, 2017.

(51) Int. Cl.
  *C07D 487/14*  (2006.01)
  *A61K 45/06*  (2006.01)

(52) U.S. Cl.
  CPC .......... *C07D 487/14* (2013.01); *A61K 45/06* (2013.01); *C07B 2200/13* (2013.01)

(58) Field of Classification Search
  CPC .................................................. C07D 487/14
  See application file for complete search history.

(56) References Cited

U.S. PATENT DOCUMENTS

| | | | |
|---|---|---|---|
| 6,962,993 B2 | 11/2005 | Blumenkopf et al. | |
| 7,345,171 B2 | 3/2008 | Beylin et al. | |
| 2004/0236084 A1 | 11/2004 | Biwersi et al. | |
| 2011/0009353 A1 | 1/2011 | Chen-Kiang et al. | |
| 2011/0312909 A1 | 12/2011 | Ciomei et al. | |
| 2014/0274896 A1 | 9/2014 | Sharpless et al. | |
| 2014/0275067 A1 | 9/2014 | Sharpless et al. | |
| 2015/0246925 A1 | 9/2015 | Tavares et al. | |
| 2015/0299212 A1 | 10/2015 | Strum et al. | |
| 2016/0108054 A1 | 4/2016 | Tavares et al. | |
| 2017/0119774 A1 | 5/2017 | Strum et al. | |
| 2017/0246171 A1 | 8/2017 | Strum et al. | |

FOREIGN PATENT DOCUMENTS

| | | |
|---|---|---|
| JP | 2007-530425 | 11/2007 |
| WO | WO 1998/033798 | 8/1998 |
| WO | WO 1999/015500 A1 | 4/1999 |
| WO | WO 2003/062236 A1 | 7/2003 |
| WO | WO 2005/005426 | 1/2005 |
| WO | WO 2005/040166 A1 | 5/2005 |
| WO | WO 2005/052147 A2 | 6/2005 |
| WO | WO 2005/105213 A2 | 11/2005 |
| WO | WO 2006/074985 | 7/2006 |
| WO | WO 2007/048847 A2 | 5/2007 |
| WO | WO 2009/003003 A2 | 12/2008 |
| WO | WO 2009/085185 A1 | 7/2009 |
| WO | WO 2010/020675 A1 | 2/2010 |
| WO | WO 2010/039997 A2 | 4/2010 |
| WO | WO 2010/051127 A2 | 5/2010 |
| WO | WO 2010/132725 A2 | 11/2010 |
| WO | WO 2011/101409 | 8/2011 |
| WO | WO 2011/103485 A1 | 8/2011 |
| WO | WO 2012/061156 | 10/2012 |
| WO | WO 2013/148748 A1 | 10/2013 |
| WO | WO 2013/163239 A1 | 10/2013 |
| WO | WO 2015/061407 | 4/2015 |
| WO | WO 2018/156812 A1 | 8/2018 |

OTHER PUBLICATIONS

US, U.S. Pat. No. 8,598,186, B2, U.S. Appl. No. 13/869,520, Tavares et al., Dec. 3, 2013.
US, U.S. Pat. No. 8,598,197, B2, U.S. Appl. No. 13/869,576, Tavares et al., Dec. 3, 2013.
US, U.S. Pat. No. 8,691,830, B2, U.S. Appl. No. 13/869,594, Tavares et al., Apr. 8, 2014.
US, U.S. Pat. No. 8,822,683, B2, U.S. Appl. No. 14/162,649, Tavares et al., Sep. 2, 2014.
US, U.S. Pat. No. 8,829,012, B2, U.S. Appl. No. 14/162,637, Tavares et al., Sep. 9, 2014.
US, U.S. Pat. No. 9,102,682, B2, U.S. Appl. No. 14/452,296, Tavares et al., Aug. 11, 2015.
US, U.S. Pat. No. 9,260,442, B2, U.S. Appl. No. 14/498,796, Tavares et al., Jan. 27, 2016.
US, U.S. Pat. No. 9,464,092, B2, U.S. Appl. No. 14/212,911, Strum et al., Oct. 11, 2016.
US, U.S. Pat. No. 9,481,691, B2, U.S. Appl. No. 14/712,630, Tavares et al., Nov. 1, 2016.
US, U.S. Pat. No. 9,487,530, B2, U.S. Appl. No. 14/212,430, Strum et al., Nov. 8, 2016.

(Continued)

*Primary Examiner* — Brian E McDowell
(74) *Attorney, Agent, or Firm* — Knowles Intellectual Property Strategies, LLC

(57) ABSTRACT

This invention provides an unexpectedly stable, highly crystalline form of the di-HCl salt of

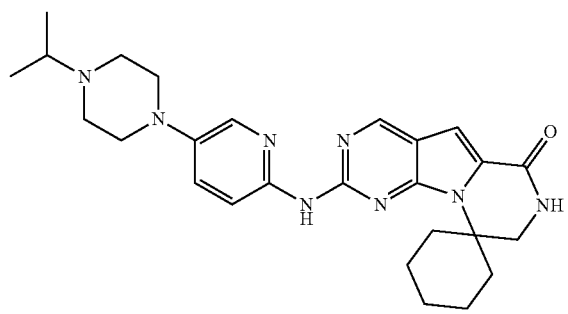

for advantageous therapeutic pharmaceutical efficacy and dosage form stability.

20 Claims, 34 Drawing Sheets

(56) References Cited

OTHER PUBLICATIONS

US, U.S. Pat. No. 9,499,564, B2, U.S. Appl. No. 14/712,582, Tavares et al., Nov. 22, 2016.
US, U.S. Pat. No. 9,527,857, B2, U.S. Appl. No. 14/214,048, Strum et al., Dec. 27, 2016.
US, U.S. Pat. No. 9,717,735, B2, U.S. Appl. No. 14/690,180, Strum et al., Aug. 1, 2017.
US, U.S. Pat. No. 9,745,316, B2, U.S. Appl. No. 14/982,443, Tavares et al., Aug. 29, 2017.
US, U.S. Pat. No. 9,856,268, B2, U.S. Appl. No. 15/348,862, Tavares et al., Jan. 2, 2018.
US, U.S. Pat. No. 9,931,345, B2, U.S. Appl. No. 15/288,878, Strum et al., Apr. 3, 2018.
US, U.S. Pat. No. 9,957,276, B2, U.S. Appl. No. 15/348,770, Tavares et al., May 1, 2018.
US, U.S. Pat. No. 10,076,523, B2, U.S. Appl. No. 15/387,083, Strum et al., Sep. 18, 2018.
US, U.S. Pat. No. 10,085,992, B2, U.S. Appl. No. 15/342,990, Strum et al., Oct. 2, 2018.
US, U.S. Pat. No. 10,189,849, B2, U.S. Appl. No. 15/918,834, Tavares et al., Jan. 29, 2019.
US, U.S. Pat. No. 10,189,850, B2, U.S. Appl. No. 15/918,852, Tavares et al., Jan. 29, 2019.
US, U.S. Pat. No. 10,189,851, B2, U.S. Appl. No. 15/918,877, Tavares et al., Jan. 29, 2019.
US, U.S. Pat. No. 10,231,969, B2, U.S. Appl. No. 15/457,699, Strum, et al., Mar. 19, 2019.
US, U.S. Pat. No. 10,413,547, B2, U.S. Appl. No. 16/142,574, Strum, et al., Jan. 31, 2019.
US, U.S. Pat. No. 10,376,519, B2, U.S. Appl. No. 15/665,071, Strum, et al., Aug. 13, 2019.
US, U.S. Pat. No. 10,434,104, B2, U.S. Appl. No. 16/112,362, Strum, et al., Oct. 8, 2019.
US, U.S. Appl. No. 10,464,940, B2, U.S. Appl. No. 15/860,483, Tavares et al., Nov. 5, 2019.
US, 2018/0221378, A1, U.S. Appl. No. 15/943,278, Strum, et al., Aug. 9, 2018.
US, 2018/0360840, A1, U.S. Appl. No. 16/112,360, Strum, et al., Dec. 20, 2018.
US, 2019/0070185, A1, U.S. Appl. No. 16/178,419, Strum, et al., Mar. 7, 2019.
US, 2019/0119292, A1, U.S. Appl. No. 16/226,430, Tavares et al., Apr. 25, 2019.
US, 2019/0119294, A1, U.S. Appl. No. 16/230,412, Strum, et al., Apr. 25, 2019.
US, 2019/0125752, A1, U.S. Appl. No. 16/228,308, Strum, et al., May 2, 2019.
US, 2019/0135811, A1, U.S. Appl. No. 16/230,396, Strum et al., May 8, 2019.
US, 2019/0135784, A1, U.S. Appl. No. 16/230,388, Strum, et al., May 9, 2019.
US, 2019/0135820, A1, U.S. Appl. No. 16/230,308, Smith et al., May 9, 2019.
US, 2019/0151311, A1, U.S. Appl. No. 16/254,364, Strum, et al., May 23, 2019.
US, 2019/0167691, A1, U.S. Appl. No. 16/268,317, Strum et al., Jun. 6, 2019.
US, 2019/0321370, A1, U.S. Appl. No. 16/432,244, Sorrentino et al., Oct. 24, 2019.
US, 2019/0374545, A1, U.S. Appl. No. 16/547,342, Sorrentino et al., Dec. 12, 2019.
US, 2020/0022983, A1, U.S. Appl. No. 16/572,418, Strum et al., Jan. 23, 2020.
Bisi, J.E. et al. "Preclinical Characterization of G1T28: A Novel CDK4/6 Inhibitor for Reduction of Chemotherapy-Induced Myelosuppression", Molecular Cancer Therapeutics, 2016, 15(5), 783-793, XP055457141.
Bisi, John E., et al., "Preclinical development of G1T28: a novel potent and selective inhibitor of cyclin dependent kinases 4/6 for use as an oral antineoplastic in patients with CDK4/6 sensitive tumors", Oncotarget, 2017, 8(26), 42343-42358, XP055743204.
European extended Search Report for PCT/US2018/040435 dated Nov. 3, 2020.
Mino, R Caira., "Crystalline Polymorphism of Organic Compounds", Topics in Current Chemistry, Springer, berlin, DE, 1998, 198, 163-208; ISSN: 0340-1022; DOI: 10.1007/3-540-69178-2_5.
Stice, James P. et al., "CDK4/6 Therapeutic Intervention and viable alternative to taxane in CRPC", Molecular Cancer Research, 2017, 15(6), 660-669, XP55457140.
Chu et al. "Discovery of [4-Amino-2-(1-methanesulfonylpiperidin-4-ylamino)pyrimidin-5-yl](2,3-difluoro-6-methoxyphenyl)methanone (R547), a potent and selective cyclin-dependent kinase inhibitor with significant in vivo antitumor activity" J Med Chem, Nov. 2, 2006; 49(22): 6549-6560.
Goldberg et al. "Pyrazinoindolone inhibitors of MAPKAP-K2" Bioogranic & Medicinal Chemistry Letters, Dec. 23, 2007, 18, 938-941.
Guillard et al., "Synthesis and biological evaluations of new pyrrolo[2,3-b]pyrimidine as SDI analogs" Heterocyles, 2008, vol. 75(5), pp. 1163-1189.
International Search Report PCT//US18/40435 dated on Sep. 26. 2018.
Kubinyi (3D QSAR in Drug Design: Ligand-Protien Interactions and Molecular Similarity, vol. 2-3, Springer, 1998, 800 pages). p. 243-44.
Mcinnes, C. "Progress in the evaluation of CDK inhibitors as anti-tumor agents" Drug Discov Today, Oct. 2008; 13(19-20): 875-881.
Park et al. "Toxixogenetics in drug development" Toxicology Letters, Mar. 31, 2001, 120, 281-291.
Presser, Armin and Antje Hüfner "Trimethylsilyldiazomethane—A Mild and Efficient Reagent for the Methylation of Carboxylic Acids and Alcohols in Natural Products" Monatshefte für Chemie, 2004, vol. 135, Issue 8, pp. 1015-1022.
Schönauer, K. and E. Zibral "Reactions with organophosphorus compounds, 50.: Trimethylsilylethoxymethylene triphenylphosphorane, a novel reagent for the homologation of carbonyl compounds." Tetrahedron Letters, 1983, vol. 24, pp. 573-576.
Shimamura, T. et al. "Identification of potent 5-pyrimidinyl-2-aminothiazole CDK4, 6 inhibitors with significant selectivity over CDK1, 2, 5, 7, and 9" Bioorg Med Chem Lett., Jul. 15, 2006; 16(14): 3751-3754.
Sielecki et al (BMCL 11 (2001) 1157-1160).
Soni, R. et al. "Selective in vivo and in vitro effects of a small molecule inhibitor of cyclin-dependent kinase 4" J Natl Cancer Inst, Mar. 21, 2001; 93(6): 436-446.
Toogood, P. L. et al. "Discovery of a potent and selective inhibitor of cyclin-dependent kinase 4/6" J Med Chem, Apr. 7, 2005; 48(7): 2388-2406.
Wermuth, The Practice of Medicinal Chemistry, 2d ed. (2003), 768 pages. Chs. 9-10.
White, J.D. et al. "Transformations of Quinic Acid. Asymmetric Synthesis and Absolute Configuration of Mycosporin I and Mycosporin-gly" Journal of Organic Chemistry, 1995, vol. 60, Issue 12, pp. 3600-3611.
US, U.S. Pat. No. 10,618,905, B2, U.S. Appl. No. 16/230,412, Strum, et al., Apr. 14, 2020.
US, U.S. Pat. No. 10,654,831, B2, U.S. Appl. No. 16/230,388, Strum, et al., May 19, 2020.
US, U.S. Pat. No. 10,660,896, B2, U.S. Appl. No. 15/943,278, Strum, et al., May 26, 2020.
US, U.S. Pat. No. 10,696,682, B2, U.S. Appl. No. 16/226,430, Tavares et al., Jun. 30, 2020.
US, U.S. Pat. No. 10,709,711, B2, U.S. Appl. No. 16/228,308, Strum, et al., Jul. 14, 2020.
US, U.S. Pat. No. 10,829,490, B2, U.S. Appl. No. 16/230,396, Strum, et al., Nov. 10, 2020.
US, 2020/0239486, A1, U.S. Appl. No. 16/847,426, Strum, et al., Jul. 30, 2020.

(56) References Cited

OTHER PUBLICATIONS

US, 2020/0277300, A1, U.S. Appl. No. 15/931,330, Tavares et al., Sep. 3, 2020.
US, 2020/0283406, A1, U.S. Appl. No. 16/877,249, Strum, et al., Sep. 10, 2020.
US, 2020/0331925, A1, U.S. Appl. No. 16/918,985, Strum, et al., Oct. 22, 2020.
US, 2020/0345742, A1, U.S. Appl. No. 16/886,309, Strum, et al., Nov. 5, 2020.
US, 2020/0345743, A1, U.S. Appl. No. 16/926,035, Strum, et al., Nov. 5, 2020.
U.S. Appl. No. 16/924,033, Beelen et al., filed Jul. 8, 2020.
U.S. Appl. No. 17/067,549, Strum, et al., filed Oct. 9, 2020.
U.S. Appl. No. 17/088,298, Strum, et al., filed Nov. 3, 2020.

MORPHIC FORMS OF G1T38 AND METHODS OF MANUFACTURE THEREOF

CROSS-REFERENCE TO RELATED APPLICATIONS

This application is a continuation of International Application No. PCT/US2018/040435, filed in the International Patent Cooperation Treaty, U.S. Receiving Office on Jun. 29, 2018, which claims the benefit of U.S. Provisional Application No. 62/526,937 which was filed on Jun. 29, 2017. The entirety of these applications are hereby incorporated by reference herein for all purposes.

FIELD OF THE INVENTION

This invention provides an advantageous isolated morphic form of the di-HCl salt, of G1T38, which is (2'-((5-(4-isopropylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one).

BACKGROUND

U.S. Pat. Nos. 8,822,683; 8,598,197; 8,829,102 and 9,102,683 and corresponding WO 2012/061156 assigned to G1 Therapeutics, Inc. describe a class of N-(heteroaryl)-pyrrolo[3,2-d]pyrimidin-2-amine cyclin dependent kinase inhibitors including 2'-((5-(4-isopropylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one (Compound 1) with the formula Compound 1

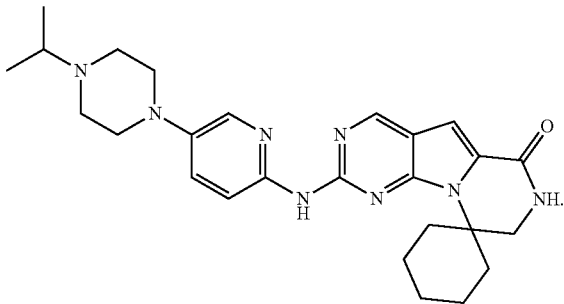

The compound is currently referred to as "G1T38". The di-HCl salt of G1T38 (Compound 2) is currently in Phase Ib/2a human clinical trials in the United States with the U.S. Food and Drug Administration for the treatment of estrogen positive, HER2-negative breast cancer after endocrine therapy failure. G1T38 has also been favorably evaluated in a Phase 1a toxicity trial in 75 women and found to be well tolerated with no significant adverse events.

Compound 2

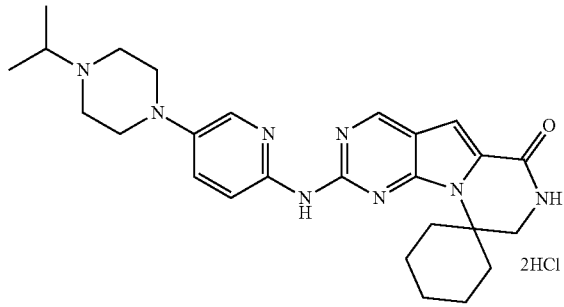 [SMILES: CC(C)N1CCN(c2ccc(Nc3ncc4cc5n(c4n3)C3(CCCCC3)CNC5=O)nc2)CC1]

G1T38 induces inhibition of cell proliferation in a variety of CDK4/6-dependent tumorigenic cell lines including breast, melanoma, leukemia, and lymphoma cells and inhibits RB phosphorylation in vitro and in vivo. Additional favorable therapeutic properties of G1T38, including the selectivity for tumors over plasma in mouse xenograft tumors, are highlighted in an article recently released in a peer reviewed journal (Bisi, et al., Preclinical development of G1T38: A novel, potent and selective inhibitor of cyclin dependent kinases 4/6 for use as an oral antineoplastic in patients with CDK 4/6 sensitive tumors", *Oncotarget*, Mar. 15, 2017). See also U.S. Pat. No. 9,527,857.

Other publications that describe compounds of this general class include the following. WO 2014/144326 filed by Strum et al. and assigned to G1 Therapeutics describes compounds and methods for protection of normal cells during chemotherapy using pyrimidine based CDK4/6 inhibitors. WO 2014/144596 filed by Strum et al. and assigned to G1 Therapeutics describes compounds and methods for protection of hematopoietic stem and progenitor cells against ionizing radiation using pyrimidine based CDK4/6 inhibitors. WO 2014/144847 filed by Strum et al. and assigned to G1 Therapeutics describes HSPC-sparing treatments of abnormal cellular proliferation using pyrimidine based CDK4/6 inhibitors. WO2014/144740 filed by Strum et al. and assigned to G1 Therapeutics describes highly active anti-neoplastic and anti-proliferative pyrimidine based CDK 4/6 inhibitors. WO 2015/161285 filed by Strum et al. and assigned to G1 Therapeutics describes tricyclic pyrimidine based CDK inhibitors for use in radioprotection. WO 2015/161287 filed by Strum et al. and assigned to G1 Therapeutics describes analogous tricyclic pyrimidine based CDK inhibitors for the protection of cells during chemotherapy. WO 2015/161283 filed by Strum et al. and assigned to G1 Therapeutics describes analogous tricyclic pyrimidine based CDK inhibitors for use in HSPC-sparing treatments of RB-positive abnormal cellular proliferation. WO 2015/161288 filed by Strum et al. and assigned to G1 Therapeutics describes analogous tricyclic pyrimidine based CDK inhibitors for use as anti-neoplastic and anti-proliferative agents. WO 2016/040858 filed by Strum et al. and assigned to G1 Therapeutics describes the use of combinations of pyrimidine based CDK4/6 inhibitors with other anti-neoplastic agents. WO 2016/040848 filed by Strum et al. and assigned to G1 Therapeutics describes compounds and methods for treating certain Rb-negative cancers with CDK4/6 inhibitors and topoisomerase inhibitors.

Other biologically active fused spirolactams and their syntheses are described, for example, in the following publications. Griffith, D. A., et al. (2013). "Spirolactam-Based Acetyl-CoA Carboxylase Inhibitors: Toward Improved Metabolic Stability of a Chromanone Lead Structure." Journal of Medicinal Chemistry 56(17): 7110-7119, describes metabolically stable spirolactams wherein the lactam resides on the fused ring for the inhibition of acetyl-CoA carboxylase. WO 2013/169574 filed by Bell et al. describes aliphatic spirolactams as CGRP receptor antagonists wherein the lactam resides on the spiro ring. WO 2007/061677 filed by Bell et al. describes aryl spirolactams as CGRP receptor antagonists wherein the lactam resides on the spiro ring. WO 2008/073251 filed by Bell et al. describes constrained spirolactam compounds wherein the lactam resides on the spiro ring as CGRP receptor antagonists. WO 2006/031606 filed by Bell et al. describes carboxamide spirolactam compounds wherein the spirolactam resides on the spiro ring as CGRP receptor antagonists. WO 2006/031610, WO 2006/031491, and WO 2006/029153 filed by Bell et al. describe anilide spirolactam compounds wherein the spirolactam resides on the spiro ring. WO 2008/109464 filed by Bhunai et al. describes spirolactam compounds wherein the lactam resides on the spiro ring which is optionally further fused.

Given the therapeutic importance of G1T38 to patients suffering from a proliferative disorder such as a tumor or cancer, it would be beneficial to provide an advantageous means for delivery that may increase therapeutic activity and/or stability.

SUMMARY

It has been discovered that Compound 2, di-HCl salt of G1T38 (2'-((5-(4-isopropylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one) can be prepared in a highly purified, advantageous morphic form, referred to herein as Form B.

Form B of Compound 2 is an unexpected, highly stable, highly crystalline form of solid Compound 2, which is beneficial for therapeutic efficacy and for the manufacture of pharmaceutical formulations. As discussed in Example 4, Form B is stable under thermal stress of 60° C. for 7 days. Additionally, a long-term stability study at 25° C. and 60% relative humidity revealed that isolated Compound 2 Form B is stable for at least 1 year (Example 7). In one embodiment isolated Compound 2 Form B is stable for at least about 6, 7, 8, 9, 10, 11, 12, 14, 16, 18, 20, 22, or 24 months.

Compound 2

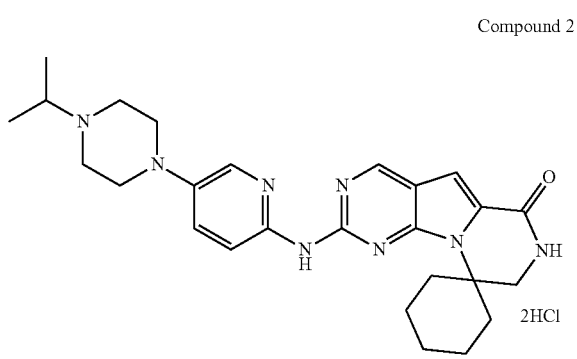 [SMILES: CC(C)N1CCN(c2ccc(Nc3ncc4cc5n(c4n3)C3(CCCCC3)CNC5=O)nc2)CC1]

A number of crystallization and slurry experiments were conducted (Example 2, Tables 1-4) by varying temperature, cooling procedure, and isolation procedure. From these experiments, eleven unique forms of Compound 2 were discovered, but only Form A, Form B, and Form D were appropriate for evaluation. The other forms resulted in weak crystalline forms, solvates, unstable hydrates, or anhydrates. Of the three solid forms, Form B was discovered to be an unexpectedly superior highly crystalline stable material for therapeutic dosage forms. In the dynamic vapor sorption experiment, Compound 2 remained in Form B after exposure to 90% relative humidity (Example 3).

Form B has advantageous properties for use as an active pharmaceutical ingredient in a solid dosage form and may have increased efficacy in such a formulation. In one embodiment, Form B is produced by recrystallization from HCl and acetone, as described in more detail below. In one embodiment, Form B is characterized by an XRPD pattern substantially similar to that set forth in FIG. 7. In one embodiment, Form B is characterized by an XRPD pattern comprising at least three 2theta values selected from 6.5°±0.2, 9.5±0.2°, 14.0±0.2°, 14.4±0.2°, 18.1±0.2°, 19.7±0.2°, and 22.4±0.2°. In one embodiment, Form B is characterized by an XRPD pattern comprising at least the 2theta values of 9.5±0.2°. In some embodiments isolated Compound 2, Form B is characterized by the absence of at least one of the peaks at 4.6±0.2° 2theta. In some embodiments isolated Compound 2, Form B is characterized by the absence of a peak at 5.0±0.2° 2theta. In one embodiment, isolated Form B is characterized as having a 7.5% weight loss between 31 and 120° C. in a thermogravimetric infrared (TG-IR) analysis. In one embodiment, isolated Form B is characterized as having differential scanning calorimetry (DSC) onset endotherms at about 105±20° C., about 220±20° C., and about 350±20° C., for example at 105° C., 220° C., and 350° C. or 92° C., 219° C., and 341° C.

Thus, the present invention generally provides an isolated morphic Form B of Compound 2, pharmaceutical compositions containing such morphic form, methods of inhibiting or reducing the activity of CDK4 or CDK6 in a host using said isolated morphic form, and treating a host having a pRb-positive cancer such as, for example, estrogen receptor-positive (ER+) breast cancer, non-small cell lung cancer (NSCLC), or prostate cancer, using the morphic form described herein, and methods of preparing such morphic form.

Compound 2 Form B can be produced, for example, by recrystallizing Compound 1 in concentrated HCl and acetone. In one embodiment, Compound 1 is dissolved in concentrated HCl and heated. This is followed by the addition of acetone and isolation of the product by cooling and filtration.

In one embodiment, Compound 2 Form B is produced by the recrystallization of Compound 2 Form D. In an alternative embodiment, Compound 2 Form B is produced by repeated recrystallizations. In one embodiment, pure Compound 2 Form B is purified from impure Compound 2 Form B by a water:acetone (1:2) (v/v) slurry followed by vacuum drying.

Compound 2 Form A has less stability than Form B. Form A was produced when MeOH, EtOH, and 1-BuOH were used as solvents in the single solvent crystallizations and it was also produced in the binary solvent crystallizations using water and MeOH as the primary solvent. Slurry experiments using n-heptane and c-hexane produced Form A as well.

Compound 2 Form D has less stability than Form B. In one embodiment, Form D is produced by stirring a slurry of Compound 2 in acetonitrile at room temperature. In another embodiment, Form D is produced by dissolving Compound 1 in concentrated HCl before heating. Then the solution is allowed to cool and acetone is only added after crystallization begins to drive the precipitation to completion. The precipitate is then isolated via filtration. In an alternative embodiment, Form D is produced by dissolving Compound 1 in concentrated HCl before heating. Then the solution is allowed to cool and acetone is only added once crystallization has occurred and all solids are collected via filtration.

In alternative embodiments, a combination of two or more Forms of Compound 2 is provided, such as Forms B and D; Forms B and A; or Forms A and D. In an alternative embodiment, an isolated combination of three forms is provided, for example, Forms A, B, and D.

In one embodiment a pharmaceutical composition is provided comprising isolated Compound 2 morphic Form B and a pharmaceutically acceptable excipient. In another embodiment, the pharmaceutical composition further comprises one or more additional therapeutic agents, for example but not limited to, an anti-estrogen, anti-androgen, an antineoplastic agent, an aromatase inhibitor, a Bruton's tyrosine kinase (BTK) inhibitor, a CYP17 inhibitor, an extracellular signal-regulated kinase (ERK) inhibitor, a gonadotropin releasing hormone superagonist (GnRH agonist), a luteinizing hormone-releasing hormone (LH-RH) agonist, a luteinizing hormone-releasing hormone (LH-RH) antagonist, a mechanistic target of rapamycin (mTOR) inhibitor, a mitogen-activated protein kinase (MEK) inhibitor, a nucleoside or nucleotide analogue or prodrug, a phosphatidylinositol 3-kinase (PI3K) pathway inhibitor, a rapidly accelerated fibrosarcoma (RAF) kinase inhibitor, a renin-angiotensin system (RAS) inhibitor, a selective estrogen receptor degrader (SERD), a selective estrogen receptor modulator (SERM), a serine-threonine protein kinase B (Akt) inhibitor, or a topoisomerase inhibitor. In one embodiment, the one or more additional therapeutic agents are selected from letrazole, anastrozole, fulvestrant, tamoxifen, etoposide, enzalutamide, pictilisib, exemestane, or a combination thereof.

In another embodiment Compound 2 morphic Form B is used in combination with a SERD described in WO 2017/100712, WO 2017/100715, US 2017/0166550, or US 2017/0166551. In yet another embodiment a pharmaceutical composition is provided comprising isolated Compound 2 morphic Form B, a pharmaceutically acceptable excipient, and a SERD described in WO 2017/100712, WO 2017/100715, US 2017/0166550, or US 2017/0166551.

In one aspect of the present invention, a method for treating a CDK4/6 dependent cellular proliferation disorder is provided comprising administering to a host in need thereof a therapeutically effective amount of isolated Form B of Compound 2.

Also provided is the use of isolated morphic Form B in the manufacture of a medicament for treating a pRb-positive cancer, such as estrogen receptor positive (ER+) breast cancer, non-small cell lung cancer (NSCLC), prostate cancer, or other abnormal cellular proliferation in a host.

DETAILED DESCRIPTION OF THE INVENTION

It cannot be predicted in advance whether a compound exists in more than one solid form or what the various properties of any solid form might be if one or more does exist, or whether the properties are advantageous for a therapeutic dosage form. As one example, the drug ritonavir is active in one polymorphic form and inactive in another form, and the inactive form is the more stable.

Solid forms of compounds can be characterized by analytical methods such as X-ray powder diffraction pattern (XRDP), thermogravimetric analysis (TGA), TGA with IR off-gas analysis, Differential Scanning Calorimetry (DSC), melting point, FT-Raman spectroscopy, Dynamic Vapor Sorption (DVS), polarized light microscopy (PLM) or other techniques known in the art.

Eleven forms of Compound 2 were discovered from slurry and crystallization experiments. Of these eleven forms, Form A, Form B, and Form D were found to have properties suitable for further development. Moisture sorption experiments revealed that Form B is an unexpected superior crystalline stable solid.

Morphic Form B

Isolated morphic Form B of Compound 2 is provided in this invention.

Figure 7:
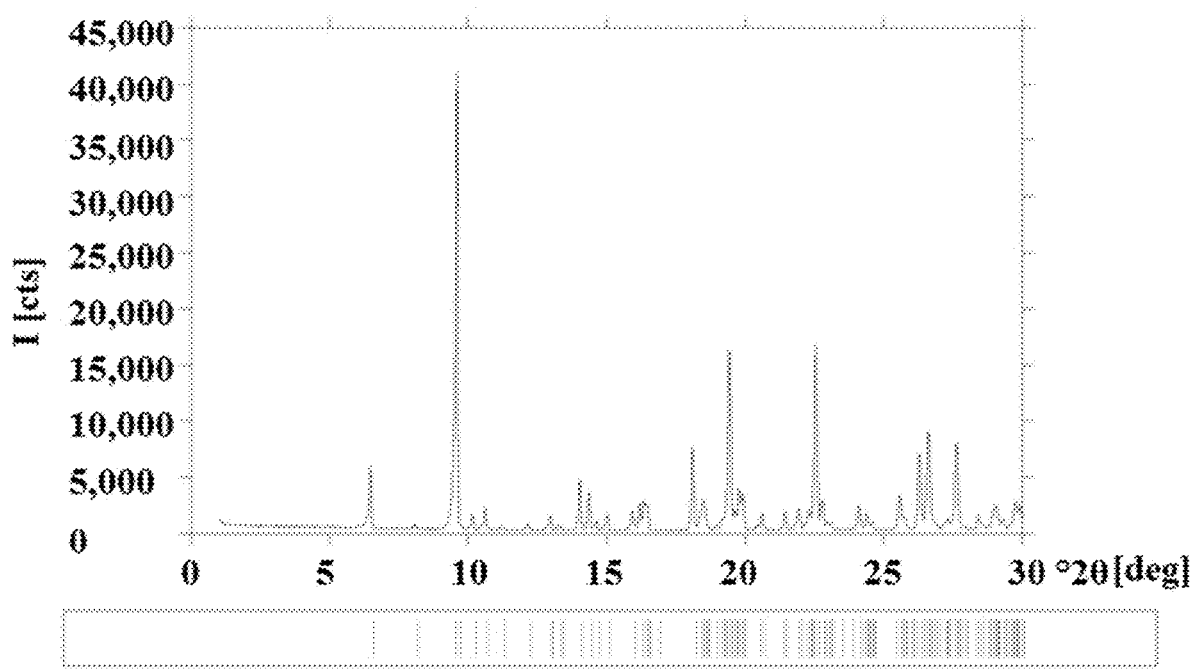
FIG. 7 is the XRPD pattern for pure Form B. The peaks, marked with bars, are listed in Example 6. The x-axis is 2Theta measured in degrees and the y-axis is intensity measured in counts.

In one embodiment, Form B is characterized by an XRPD pattern in or substantially similar to that set forth in FIG. 7. In one embodiment, Form B is characterized by an XRPD pattern comprising at least three 2theta values selected from 6.5±0.2°, 9.5±0.2°, 14.0±0.2°, 14.4±0.2°, 18.1±0.2°, 19.7±0.2°, and 22.4±0.2°. In one embodiment, Form B is characterized by an XRPD pattern comprising a peak with a 2theta value of 9.5±0.4°.

In one embodiment, Form B is characterized as having a 7.5% weight loss between 31 and 120° C. in a thermogravimetric infrared (TG-IR) analysis.

In one embodiment the isolated Compound 2 Form B does not have a peak at one or at both of 4.0±0.2° and 5.6±0.2° 2Theta, or the peak at one or at both of 4.0±0.2° and 5.6±0.2° 2Theta is not greater than 200, 150, 100, or 75 Counts Per Second (CPS).

Form B can be prepared using selective crystallization. The method can be carried out by treating a solution comprising a suitable solvent(s) and Compound 2 optionally in the presence of one or more seeds comprising Form B to conditions that provide for the crystallization of Form B. The selective crystallization can be carried out in any suitable solvent. For example, it can be carried out in an aprotic solvent or a mixture thereof. The selective crystallization can be carried out at, for example, a temperature in the range of about 40° C. to about 65° C. In another embodiment the selective crystallization can be carried out at, for example, a temperature in the range of about 45° C. to about 60° C. or about 45° C. to about 55° C.

In one embodiment, Compound 2 Form B is produced by recrystallization in a solution of hydrochloric acid. Compound 1 is dissolved in aqueous HCl and heated to at least 55±10° C. The solution is stirred for approximately 45 minutes and filtered through an in-line filter. Acetone is slowly added to the hot solution to induce crystallization. The temperature of the solution is then decreased to 25±5° C. or lower and stirred for at least 2 hours. The resulting solids are collected via filtration to afford Form B.

In an alternative embodiment, Compound 2 Form B is recrystallized from Compound 2 Form D. Compound 2 Form D is first formed by dissolving Compound 1 in aqueous HCl and heating the solution to about 55±10° C. The solution is stirred for approximately 45 minutes and the resulting solution is filtered through an in-line filter. The temperature of the solution is then decreased to about 25±5° C. and the solution is stirred for at least 2 hours. Acetone is added at a temperature of about 25±5° C. over the course of about one hour after crystallization has begun to drive crystallization to completion. The solution is stirred for about an additional 2 hours and the resulting solids are collected via filtration to afford Compound 2 Form D. Form D is then dissolved in concentrated HCl and the solution is heated. Acetone is added to the hot solution prior to the formation of any solids. As the solution cools, the solids are collected via filtration to afford Form B.

In one embodiment, impure Compound 2 Form B is converted to pure Form B in a water:acetone (1:2) (v/v) slurry at 30° C. This is followed by slow filtration that results in a wet cake. The wet cake is dried at ambient conditions for about 3.5 hours followed by vacuum drying at ambient temperature.

In certain embodiments, Form B is characterized by an XRPD pattern comprising all or at least 2, 3, 4, 5, 6, 7, 8, 9, 10, 11, 12, 13, 14, 15, 16, 17, 18, 19, or 20 2theta values selected from:

a. 6.5, 8.1, 9.4, 9.6, 10.2, 10.6, 11.2, 12.2, 12.9, 13.0, 13.3, 13.4, 14.0, 14.4, 14.6, 15.0, 15.9, 16.2, 16.4, 16.5, 16.8, 18.1, 18.4, 18.5, 18.6, 18.6, 18.9, 19.1, 19.2, 19.3, 19.4, 19.5, 19.6, 19.7, 19.8, 19.9, 20.4, 20.6, 21.3, 21.4, 21.8, 22.0, 22.2, 22.3, 22.4, 22.5, 22.8, 23.0, 23.1, 23.4, 23.8, 24.1, 24.2, 24.3, 24.4, 24.5, 24.6, 25.4, 25.6, 25.7, 25.9, 26.0, 26.1, 26.3, 26.4, 26.5, 26.6, 26.7, 26.8, 26.9, 27.2, 27.3, 27.5, 27.6, 27.7, 27.9, 28.3, 28.4, 28.5, 28.7, 28.9, 29.0, 29.1, 29.3, 29.4, 29.5, 29.6, 29.7, 29.8, 29.9, 30.0, 30.3, 30.4, 30.5, 30.6, 30.7, 30.9, 31.2, 31.5, 31.6, 31.7, 31.8, 31.9, 32.0, 32.2, 32.3, 32.4, 32.5, 32.6, 32.7, 32.8, 33.1, 33.2, 33.3, 33.6, 33.7, 33.8, 34.0, 34.1, 34.2, 34.3, 34.6, 34.7, 34.8, 35.0 35.2, 35.3, 35.5, 35.6, 35.9, 36.0, 36.2, 36.5, 36.6, 36.7, 36.8, 36.9, 37.1, 37.2, 37.3, 37.4, 37.5, 37.6, 37.7, 37.8, 37.9, 38.2, 38.3, 38.4, 38.5, 38.6, 38.7, 38.8, 38.9, 39.0, 39.1, 39.2, 39.3, 39.4, 39.5, 39.6, 39.7, 39.8, 39.9, and 40.0° 2θ; or b. 6.5, 9.4, 9.5, 9.6, 10.2, 10.6, 13.3, 13.4, 14.0, 14.4, 14.6, 15.0, 16.2, 16.4, 16.5, 16.8, 18.1, 18.4, 18.5, 18.6, 18.9, 19.1, 19.2, 19.3, 19.4, 19.5, 19.6, 19.7, 19.8, 19.9, 20.4, 22.3, 22.4, 22.5, 22.8, 23.0, 23.1, 23.4, 23.8, 26.3, 26.4, 26.5, 26.6, 26.7, 26.8, 26.9, 27.2, 27.3, 27.5, 27.6, 27.7, 27.9, 28.3, 28.4, 28.5, 28.7, 28.9, 29.0, 29.1, 29.3, 29.4, 29.5, 29.6, 29.7, 29.8, 29.9, and 30.0, ° 2θ; or c. 6.5, 9.4, 9.5, 9.6, 10.2, 10.6, 13.3, 13.4, 14.0, 14.4, 14.6, 15.0, 16.2, 16.4, 16.5, 16.8, 18.1, 18.4, 18.5, 18.6, 18.9, 19.1, 19.2, 19.3, 19.4, 19.5, 19.6, 19.7, 19.8, 19.9, 20.4, 22.3, 22.4, 22.5, 22.8, 26.3, 26.4, 26.5, 26.6, 26.7, 26.8, 26.9, 27.7, 27.9, 27.9, 29.0, 29.1, 29.3, 29.4, 29.5, 29.6, 29.7, 29.8, 29.9, and 30.0, ° 2θ; or d. 6.5, 9.4, 9.5, 9.6, 10.2, 10.6, 13.3, 13.4, 14.0, 14.4, 14.6, 15.0, 16.2, 16.4, 16.5, 16.8, 18.1, 18.4, 18.5, 18.6, 18.9, 19.1, 19.2, 19.3, 19.4, 19.5, 19.6, 19.7, 19.8, 19.9, 20.4, 22.3, 22.4, 22.5, 22.8, 26.3, 26.4, 26.5, 26.6, 26.7, 26.8, 26.9, 27.7, 27.9, and 27.9, ° 2θ; or e. 6.5, 9.4, 9.5, 9.6, 10.2, 10.6, 14.0, 14.4, 14.6, 15.0, 16.2, 16.4, 16.5, 18.1, 18.4, 18.5, 18.6, 18.9, 19.1, 19.2, 19.3, 19.4, 19.5, 19.6, 19.7, 19.8, 19.9, 20.4, 22.3, 22.4, 22.5, 22.8, 26.3, 26.4, 26.5, 26.6, 26.7, 26.8, 26.9, 27.7, 27.9, and 27.9, ° 2θ; or f. 6.5, 9.5, 14.0, 14.4, 14.6, 18.1, 18.4, 18.5, 18.6, 18.9, 19.1, 19.2, 19.3, 19.4, 19.5, 19.6, 19.7, 19.8, 19.9, 20.4, 22.3, 22.4, 22.5, 22.8, 26.3, 26.4, 26.5, 26.6, 26.7, 26.8, 26.9, 27.7, 27.9, and 27.9, ° 2θ; or g. 9.5, 14.6, 18.1, 18.4, 18.5, 18.6, 18.9, 19.1, 19.2, 19.3, 19.4, 19.5, 19.6, 19.7, 19.8, 19.9, 20.4, 22.3, 22.4, 22.5, 22.8, 26.3, 26.4, 26.5, 26.6, 26.7, 26.8, 26.9, 27.7, 27.9, and 27.9, ° 2θ; or h. 9.5, 14.6, 18.1, 18.4, 18.5, 18.6, 18.9, 19.2, 19.3, 19.4, 19.5, 19.6, 19.7, 20.4, 22.3, 22.4, 22.5, 22.8, 26.3, 26.4, 26.5, 26.6, 26.7, 26.8, 26.9, 27.7, 27.9, and 27.9, ° 2θ; or i. 9.5, 14.6, 18.1, 18.4, 18.5, 18.6, 18.9, 19.2, 19.3, 19.4, 19.5, 19.6, 19.7, 22.3, 22.4, 22.5, 26.3, 26.4, 26.5, 26.6, 26.7, 26.8, 26.9, 27.7, 27.9, and 27.9, ° 2θ; or j. 9.5, 18.1, 18.4, 19.2, 19.3, 19.4, 19.5, 19.6, 19.7, 22.3, 22.4, 22.5, 26.3, 26.4, 26.5, 26.6, 26.7, 26.8, 26.9, 27.7, 27.9, and 27.9, ° 2θ; or k. 9.5, 18.1, 18.4, 19.3, 19.7, 22.3, 22.4, 22.5, 26.3, 26.4, 26.5, 26.6, 26.7, 26.8, 26.9, 27.7, 27.9, and 27.9, ° 2θ; or l. 9.5, 18.1, 18.4, 19.3, 19.7, 22.4, 26.3, 26.4, 26.5, 26.6, 26.7, 26.8, 26.9, 27.7, 27.9, and 27.9, ° 2θ; or m. 9.5, 18.1, 18.4, 19.3, 19.7, 22.4, 26.6, 27.7, 27.9, and 27.9, ° 2θ; or n. 9.5, 18.1, 18.4, 19.3, 19.7, 22.4, 26.6, and 27.7, ° 2θ; or o. 9.5, 18.1, 19.3, 19.7, 22.4, 26.6, and 27.7, ° 2θ; or p. 9.5, 18.1, 19.3, 22.4, 26.6, and 27.7, ° 2θ; or q. any of the above peak lists wherein the ° 2θ are ±0.1; or r. any of the above peak lists wherein the ° 2θ are ±0.2;

s. any of the above peak lists wherein the ° 2θ are ±0.3;

t. any of the above peak lists wherein the ° 2θ are ±0.4;

u. any of the above peak lists wherein the ° 2θ of the peak at 9.5 is ±0.4;

v. any of the above peak lists wherein the ° 2θ of the peak at 9.5 is ±0.4 and the remaining peaks are ±0.1° 2θ;

w. any of the above peak lists wherein the ° 2θ of the peak at 9.5 is ±0.4 and the remaining peaks are ±0.2° 2θ;

In one embodiment Form B is characterized by an XRPD pattern described above and is further characterized by having no peaks of greater than 200 CPS in between 4 and 6 ° 2θ. In one embodiment Form B is characterized by an XRPD pattern described above and is further characterized by having no peaks of greater than 150 CPS in between 4 and 6 ° 2θ. In one embodiment Form B is characterized by an XRPD pattern described above and is further characterized by having no peaks of greater than 100 CPS in between 4 and 6 ° 2θ. In one embodiment Form B is characterized by an XRPD pattern described above and is further characterized by having no peaks of greater than 75 CPS in between 4 and 6 ° 2θ.

In one embodiment Form B is characterized by an XRPD pattern described above and is further characterized by having no peak of about 4.0 ° 2θ of greater than 150 CPS. In one embodiment Form B is characterized by an XRPD pattern described above and is further characterized by having no peak of about 4.0 ° 2θ of greater than 100 CPS. In one embodiment Form B is characterized by an XRPD pattern described above and is further characterized by having no peak of about 4.0 ° 2θ greater than 75 CPS.

In one embodiment Form B is characterized by an XRPD pattern described above and is further characterized by having no peak of about 5.6 ° 2θ of greater than 150 CPS. In one embodiment Form B is characterized by an XRPD pattern described above and is further characterized by having no peak of about 5.6 ° 2θ of greater than 100 CPS. In one embodiment Form B is characterized by an XRPD pattern described above and is further characterized by having no peak of about 5.6 ° 2θ greater than 75 CPS in between 4 and 6 ° 2θ.

In one embodiment Form B is characterized by an XRPD pattern described above and is further characterized by having no peak of about 5.3 ° 2θ of greater than 150 CPS. In one embodiment Form B is characterized by an XRPD pattern described above and is further characterized by having no peak of about 5.3 ° 2θ of greater than 100 CPS. In one embodiment Form B is characterized by an XRPD pattern described above and is further characterized by having no peak of about 5.3 ° 2θ greater than 75 CPS in between 4 and 6 ° 2θ.

In a further embodiment, the CPS counts above are base-line corrected.

Methods utilized in preparing Form B are further described in Example 2 and Example 8 below.

Morphic Form D

In one embodiment, Form D is characterized by DSC onset endotherms at about 100±20° C., about 270±20° C., and about 347±20° C., for example at 108.3° C., 266.1° C., and 347.0° C. or 95° C., 257° C., and 344° C.

Form D can be prepared using selective crystallization. The method can be carried out by treating a solution comprising a suitable solvent(s) and Compound 2 optionally in the presence of one or more seeds comprising Form D to conditions that provide for the crystallization of Form D. The selective crystallization can be carried out in any suitable solvent. For example, it can be carried out in an aprotic solvent or a mixture thereof. In one embodiment, the solvent is acetonitrile. The selective crystallization can be carried out at, for example, a temperature in the range of about 5° C. to about 55° C.

In one embodiment, Compound 2 Form D is formed by dissolving Compound 1 in aqueous 2M HCl (10 volumes) and heating the solution to 55±10° C. The solution is stirred for approximately 45 minutes and the resulting solution is filtered through an in-line filter. The temperature of the solution is then decreased to 25±5° C. and the solution is stirred for at least 2 hours. Acetone (30 volumes) is added at a temperature of 25±5° C. over the course of an hour after crystallization has begun to drive crystallization to completion. The solution is stirred for an additional 2 hours and the resulting solids are collected via filtration to afford Compound 2 Form D.

In an alternative embodiment, Compound 2 Form D is formed by dissolving Compound 1 in aqueous 2M HCl (10 volumes) and heating the solution to 55±10° C. The solution is stirred for 45 minutes and the resulting solution is filtered through an in-line filter. The solution is cooled to 25±5° C. and the solution is stirred for at least 2 hours. The resulting solids are collected via filtration and acetone is added to afford Compound 2 Form D.

In one embodiment, Form D is again recrystallized to produce Form B.

Methods utilized in preparing Form D are further described in Example 2 below.

Morphic Form A

In one embodiment, Forma A is characterized by an XRPD peaks at about of 7.4±0.2 and 9.0±0.2 2theta. In an additional embodiment, Form A is characterized by DSC onset endotherms at about 110±20° C., about 275±20° C., and about 350±20° C., for example at 110.3° C., 275.6° C., and 344.8° C. or 103° C., 260° C., and 345° C.

Form A can be prepared using selective crystallization. The method can be carried out by treating a solution comprising a suitable solvent(s) and Compound 2 optionally in the presence of one or more seeds comprising Form A to conditions that provide for the crystallization of Form D. The selective crystallization can be carried out in any suitable solvent. For example, it can be carried out in a protic solvent or a mixture thereof. In one embodiment, the solvent is MeOH, EtOH, or 1-BuOH. The selective crystallization can be carried out at, for example, a temperature in the range of about 5° C. to about 75° C. In one embodiment, the crystallization is carried out at a temperature of about 60° C.

Methods utilized in preparing Form A are further described in Example 2 below.

Chemical Description and Terminology

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in any suitable order unless otherwise indicated herein or otherwise clearly contradicted by context. The use of any and all examples, or exemplary language (e.g., "such as"), is intended merely for illustration and does not pose a limitation on the scope of the invention unless otherwise claimed.

An "active agent" is a compound (including a compound disclosed herein), element, or mixture that when administered to a patient, alone or in combination with another compound, element, or mixture, confers, directly or indirectly, a physiological effect on the patient. The indirect physiological effect may occur via a metabolite or other indirect mechanism.

"Deuteration" and "deuterated" means that a hydrogen is replaced by a deuterium such that the deuterium exists over natural abundance and is thus "enriched". An enrichment of 50% means that rather than hydrogen at the specified position the deuterium content is 50%. For clarity, it is confirmed that the term "enriched" as used herein does not mean percentage enriched over natural abundance. In other embodiments, there will be at least 80%, at least 90%, or at least 95% deuterium enrichment at the specified deuterated position or positions. In other embodiments there will be at least 96%, at least 97%, at least 98%, or at least 99% deuterium enrichment at the specified deuterated position or positions indicated. In the absence of indication to the contrary, the enrichment of deuterium in the specified position of the compound described herein is at least 90%.

A "dosage form" means a unit of administration of an active agent. Non-limiting examples of dosage forms include tablets, capsules, injections, suspensions, liquids, intravenous fluids, emulsions, creams, ointments, suppositories, inhalable forms, transdermal forms, and the like.

"Pharmaceutical compositions" are compositions comprising at least one active agent, such as a compound or salt of one of the active compounds disclosed herein, and at least one other substance, such as a carrier. Pharmaceutical compositions optionally contain more than one active agent. "Pharmaceutical combinations" or "combination therapy" refers to the administration of at least two active agents, and in one embodiment, three or four or more active agents which may be combined in a single dosage form or provided together in separate dosage forms optionally with instructions that the active agents are to be used together to treat a disorder.

"Pharmaceutically acceptable salts" includes derivatives of the disclosed compounds in which the parent compound is modified by making inorganic and organic, suitably non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. The pharmaceutically acceptable salt can be in the form of a pure crystal, or single morphic form, or can be used in non-crystalline or amorphic, glassy, or vitreous form, or a mixture thereof. In an alternative embodiment, the active compound can be provided in the form of a solvate.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$-COOH where n is 0-4, and the like. Lists of additional suitable salts may be found, e.g., in Remington's Pharmaceutical Sciences, 17th ed., Mack Publishing Company, Easton, Pa., p. 1418 (1985).

The term "carrier" means a diluent, excipient, or vehicle with which an active compound is provided.

A "pharmaceutically acceptable excipient" means an excipient that is useful in preparing a pharmaceutical composition/combination that is generally safe, is sufficiently non-toxic, and neither biologically nor otherwise undesirable. A "pharmaceutically acceptable excipient" as used in the present application includes both one and more than one such excipient.

A "patient" or "host" is a human or non-human animal, including, but not limited to, simian, avian, feline, canine, bovine, equine or porcine in need of medical treatment. Medical treatment can include treatment of an existing condition, such as a disease or disorder, or a prophylactic or diagnostic treatment. In a particular embodiment, the patient or host is a human patient. In an alternative embodiment, the patient such as a host is treated to prevent a disorder or disease described herein.

The term "isolated" as used herein refers to the material in substantially pure form. An isolated compound does not have another component that materially affects the properties of the compound. In particular embodiments, an isolated form is at least 50, 60, 70, 80, 90, 95, 98 or 99% pure.

Methods of Treatment

In one aspect, a method of treating a proliferative disorder in a host, including a human, is provided comprising administering isolated Compound 2 morphic Form B as described herein optionally in a pharmaceutically acceptable carrier. Non-limiting examples of disorders include tumors, cancers, disorders related to abnormal cellular proliferation, inflammatory disorders, immune disorders, and autoimmune disorders.

Compound 2 morphic Form B is useful as a therapeutic agent in a dosage form when administered in an effective amount to a host, including a human, to treat a tumor, cancer (solid, non-solid, diffuse, hematological, etc.), abnormal cellular proliferation, immune disorder, inflammatory disorder, blood disorder, a myelo- or lymphoproliferative disorder such as B- or T-cell lymphomas, multiple myeloma, breast cancer, prostate cancer, AML, ALL, ACL, lung cancer, pancreatic cancer, colon cancer, skin cancer, melanoma, Waldenstrom's macroglobulinemia, Wiskott-Aldrich syndrome, or a post-transplant lymphoproliferative disorder; an autoimmune disorder, for example, Lupus, Crohn's Disease, Addison disease, Celiac disease, dermatomyositis, Graves disease, thyroiditis, multiple sclerosis, pernicious anemia, reactive arthritis, or type I diabetes; a disease of cardiologic malfunction, including hypercholesterolemia; an infectious disease, including a viral and/or bacterial infection; an inflammatory condition, including asthma, chronic peptic ulcers, tuberculosis, rheumatoid arthritis, periodontitis, ulcerative colitis, or hepatitis.

Exemplary proliferative disorders include, but are not limited to, benign growths, neoplasms, tumors, cancer (Rb positive or Rb negative), autoimmune disorders, inflammatory disorders graft-versus-host rejection, and fibrotic disorders.

Non-limiting examples of cancers that can be treated according to the present invention include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing's sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL)—also known as acute lymphoblastic leukemia or acute lymphoid leukemia (e.g., B-cell ALL, T-cell ALL), acute myelocytic leukemia (AML) (e.g., B-cell AML, T-cell AML), chronic myelocytic leukemia (CIVIL) (e.g., B-cell CIVIL, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CIVIL), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendocrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In another embodiment, the disorder is myelodysplastic syndrome (MDS).

In certain embodiments, the cancer is a hematopoietic cancer. In certain embodiments, the hematopoietic cancer is a lymphoma. In certain embodiments, the hematopoietic cancer is a leukemia. In certain embodiments, the leukemia is acute myelocytic leukemia (AML).

In certain embodiments, the proliferative disorder is a myeloproliferative neoplasm. In certain embodiments, the myeloproliferative neoplasm (MPN) is primary myelofibrosis (PMF).

In certain embodiments, the cancer is a solid tumor. A solid tumor, as used herein, refers to an abnormal mass of tissue that usually does not contain cysts or liquid areas. Different types of solid tumors are named for the type of cells that form them. Examples of classes of solid tumors include, but are not limited to, sarcomas, carcinomas, and lymphomas, as described above herein. Additional examples of solid tumors include, but are not limited to, squamous cell carcinoma, colon cancer, breast cancer, prostate cancer, lung cancer, liver cancer, pancreatic cancer, and melanoma.

In certain embodiments, the condition treated with Compound 2 morphic Form B is a disorder related to abnormal cellular proliferation.

Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic micro-angiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells, and to be caused by autoantibodies produced against collagen and IgE.

Other disorders that can include an abnormal cellular proliferative component include Bechet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

In certain embodiments a compound of the present invention and its pharmaceutically acceptable derivatives or pharmaceutically acceptable formulations containing these compounds are also useful in the prevention and treatment of HBV infections and other related conditions such as anti-HBV antibody positive and HBV-positive conditions, chronic liver inflammation caused by HBV, cirrhosis, acute hepatitis, fulminant hepatitis, chronic persistent hepatitis, and fatigue. These compounds or formulations can also be used prophylactically to prevent or retard the progression of clinical illness in individuals who are anti-HBV antibody or HBV-antigen positive or who have been exposed to HBV.

In certain embodiments, the condition is associated with an immune response.

Cutaneous contact hypersensitivity and asthma are just two examples of immune responses that can be associated with significant morbidity. Others include atopic dermatitis, eczema, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, cutaneous lupus erythematosus, scleroderma, vaginitis, proctitis, and drug eruptions. These conditions may result in any one or more of the following symptoms or signs: itching, swelling, redness, blisters, crusting, ulceration, pain, scaling, cracking, hair loss, scarring, or oozing of fluid involving the skin, eye, or mucosal membranes.

In atopic dermatitis, and eczema in general, immunologically mediated leukocyte infiltration (particularly infiltration of mononuclear cells, lymphocytes, neutrophils, and eosinophils) into the skin importantly contributes to the pathogenesis of these diseases. Chronic eczema also is associated with significant hyperproliferation of the epidermis. Immunologically mediated leukocyte infiltration also occurs at sites other than the skin, such as in the airways in asthma and in the tear producing gland of the eye in keratoconjunctivitis sicca.

In one non-limiting embodiment compounds of the present invention are used as topical agents in treating contact dermatitis, atopic dermatitis, eczematous dermatitis, psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, and drug eruptions. The novel method may also be useful in reducing the infiltration of skin by malignant leukocytes in diseases such as mycosis fungoides. These compounds can also be used to treat an aqueous-deficient dry eye state (such as immune mediated keratoconjunctivitis) in a patient suffering therefrom, by administering the compound topically to the eye.

The term "neoplasia" or "cancer" is used throughout the specification to refer to the pathological process that results in the formation and growth of a cancerous or malignant neoplasm, i.e., abnormal tissue (solid) or cells (non-solid) that grow by cellular proliferation, often more rapidly than normal and continues to grow after the stimuli that initiated the new growth cease. Malignant neoplasms show partial or complete lack of structural organization and functional coordination with the normal tissue and most invade surrounding tissues, can metastasize to several sites, are likely to recur after attempted removal and may cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present disclosed compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CIVIL), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CIVIL, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+ DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

In another aspect, a method of increasing BIM expression (e.g., BCLC2L11 expression) is provided to induce apoptosis in a cell comprising contacting a compound of the present invention or a pharmaceutically acceptable composition, salt, isotopic analog, or prodrug thereof with the cell. In certain embodiments, the method is an in vitro method. In certain embodiments, the method is an in vivo method. BCL2L11 expression is tightly regulated in a cell. BCL2L11 encodes for BIM, a proapoptotic protein. BCL2L11 is down-regulated in many cancers and BIM is inhibited in many cancers, including chronic myelocytic leukemia (CIVIL) and non-small cell lung cancer (NSCLC) and that suppression of BCL2L11 expression can confer resistance to tyrosine kinase inhibitors. See, e.g., Ng et al., Nat. Med. (2012) 18:521-528.

In yet another aspect, a method of treating a condition associated with angiogenesis is provided, such as, for example, a diabetic condition (e.g., diabetic retinopathy), an inflammatory condition (e.g., rheumatoid arthritis), macular degeneration, obesity, atherosclerosis, or a proliferative disorder, comprising administering to a subject in need thereof a compound of the present invention or a pharmaceutically acceptable composition, salt, isotopic analog, or prodrug thereof.

In certain embodiments, the condition associated with angiogenesis is macular degeneration. In certain embodiments, provided is a method of treating macular degeneration comprising administering to a subject in need thereof a compound of the present invention or a pharmaceutically acceptable composition, salt, isotopic analog, or prodrug thereof.

In certain embodiments, the condition associated with angiogenesis is obesity. As used herein, "obesity" and "obese" as used herein, refers to class I obesity, class II obesity, class III obesity and pre-obesity (e.g., being "over-weight") as defined by the World Health Organization. In certain embodiments, a method of treating obesity is provided comprising administering to a subject in need thereof a compound of the present invention or a pharmaceutically acceptable composition, salt, isotopic analog, or prodrug thereof.

In certain embodiments, the condition associated with angiogenesis is atherosclerosis. In certain embodiments, provided is a method of treating atherosclerosis comprising administering to a subject in need thereof a compound of the present invention or a pharmaceutically acceptable composition, salt, isotopic analog, or prodrug thereof.

In certain embodiments, the condition associated with angiogenesis is a proliferative disorder. In certain embodiments, provided is a method of treating a proliferative disorder comprising administering to a subject in need thereof a compound of the present invention or a pharmaceutically acceptable composition, salt, isotopic analog, or prodrug thereof.

In an alternative embodiment Compound 2 Form A or D is administered in an effective amount to treat a proliferative disorder.

In another alternative embodiment Compound 2 Form C, E, G, or H is administered in an effective amount to treat a proliferative disorder.

Methods to Reduce the Side Effects Related to Chemotherapy

In certain embodiments, the isolated Compound 2 Form B of the present invention decreases the effect of chemotherapeutic agent toxicity on CDK4/6 replication dependent healthy cells, such as hematopoietic stem cells and hematopoietic progenitor cells (together referred to as HSPCs), and/or renal epithelial cells, in subjects, typically humans, that will be, are being, or have been exposed to the chemotherapeutic agent (typically a DNA-damaging agent).

In one embodiment, the subject has been exposed to a chemotherapeutic agent, and, using the isolated Compound 2 Form B described herein, the subject's CDK4/6-replication dependent healthy cells are placed in G1 arrest following exposure in order to mitigate, for example, DNA damage. In one embodiment, the compound is administered at least ½ hour, at least 1 hour, at least 2 hours, at least 3 hours, at least 4 hours, at least 5 hours, at least 6 hours, at least 7 hours, at least 8 hours, at least 10 hours, at least 12 hours, at least 14 hours, at least 16 hours, at least 18 hours, at least 20 hours or more post chemotherapeutic agent exposure.

In one embodiment, the isolated Compound 2 Form B can allow for dose intensification (e.g., more therapy can be given in a fixed period of time) in medically related chemotherapies, which will translate to better efficacy. Therefore, the presently disclosed methods can result in chemotherapy regimens that are less toxic and more effective.

In some embodiments, the use of the isolated Compound 2 Form B described herein may result in reduced or substantially free of off-target effects, for example, related to inhibition of kinases other than CDK4 and/or CDK6 such as CDK2. Furthermore, in certain embodiments, the use of the isolated Compound 2 Form B described herein should not induce cell cycle arrest in CDK4/6 replication independent cells.

In some embodiments, the use of the isolated Compound 2 Form B described herein reduces the risk of undesirable off-target effects including, but not limited to, long term toxicity, anti-oxidant effects, and estrogenic effects. Anti-oxidant effects can be determined by standard assays known in the art. For example, a compound with no significant anti-oxidant effects is a compound that does not significantly scavenge free-radicals, such as oxygen radicals. The anti-oxidant effects of a compound can be compared to a compound with known anti-oxidant activity, such as genistein. Thus, a compound with no significant anti-oxidant activity can be one that has less than about 2, 3, 5, 10, 30, or 100 fold anti-oxidant activity relative to genistein. Estrogenic activities can also be determined via known assays. For instance, a non-estrogenic compound is one that does not significantly bind and activate the estrogen receptor. A compound that is substantially free of estrogenic effects can be one that has less than about 2, 3, 5, 10, 20, or 100 fold estrogenic activity relative to a compound with estrogenic activity, e.g., genistein.

In an alternative embodiment Compound 2 Form A or D is administered in an effective amount to decrease the effect of chemotherapeutic agent toxicity on CDK4/6 replication dependent healthy cells, such as hematopoietic stem cells and hematopoietic progenitor cells (together referred to as HSPCs), and/or renal epithelial cells, in subjects, typically humans, that will be, are being, or have been exposed to the chemotherapeutic agent (typically a DNA-damaging agent).

In an alternative embodiment Compound 2 Form C, E, G, or H is administered in an effective amount to decrease the effect of chemotherapeutic agent toxicity on CDK4/6 replication dependent healthy cells, such as hematopoietic stem cells and hematopoietic progenitor cells (together referred to as HSPCs), and/or renal epithelial cells, in subjects, typically humans, that will be, are being, or have been exposed to the chemotherapeutic agent (typically a DNA-damaging agent).

Methods to Treat Abnormal Proliferation of T-Cells, B-Cells, and/or NK-Cells

In certain aspects, the invention includes the use of an effective amount of the isolated Compound 2 Form B, or its pharmaceutically acceptable salt, prodrug or isotopic variant optionally in a pharmaceutical composition, to treat a host, typically a human, with a selected cancer, tumor, hyperproliferative condition or an inflammatory or immune disorder. Compound 2 Form B is also active against T-cell proliferation. Given the paucity of drugs for T-cell cancers and abnormal proliferation, the identification of such uses represents a substantial improvement in the medical therapy for these diseases.

Abnormal proliferation of T-cells, B-cells, and/or NK-cells can result in a wide range of diseases such as cancer, proliferative disorders and inflammatory/immune diseases. A host, for example a human, afflicted with any of these disorders can be treated with an effective amount of the isolated Compound 2 Form B as described herein to achieve a decrease in symptoms (a palliative agent) or a decrease in the underlying disease (a disease modifying agent).

Examples include T-cell or NK-cell lymphoma, for example, but not limited to: peripheral T-cell lymphoma; anaplastic large cell lymphoma, for example anaplastic lymphoma kinase (ALK) positive, ALK negative anaplastic large cell lymphoma, or primary cutaneous anaplastic large cell lymphoma; angioimmunoblastic lymphoma; cutaneous T-cell lymphoma, for example mycosis fungoides, Sézary syndrome, primary cutaneous anaplastic large cell lymphoma, primary cutaneous CD30+ T-cell lymphoproliferative disorder; primary cutaneous aggressive epidermotropic CD8+ cytotoxic T-cell lymphoma; primary cutaneous gamma-delta T-cell lymphoma; primary cutaneous small/medium CD4+ T-cell lymphoma, and lymphomatoid papulosis; Adult T-cell Leukemia/Lymphoma (ATLL); Blastic NK-cell Lymphoma; Enteropathy-type T-cell lymphoma; Hematosplenic gamma-delta T-cell Lymphoma; Lymphoblastic Lymphoma; Nasal NK/T-cell Lymphomas; Treatment-related T-cell lymphomas; for example lymphomas that appear after solid organ or bone marrow transplantation; T-cell prolymphocytic leukemia; T-cell large granular lymphocytic leukemia; Chronic lymphoproliferative disorder of NK-cells; Aggressive NK cell leukemia; Systemic EBV+ T-cell lymphoproliferative disease of childhood (associated with chronic active EBV infection); Hydroa vacciniforme-like lymphoma; Adult T-cell leukemia/lymphoma; Enteropathy-associated T-cell lymphoma; Hepatosplenic T-cell lymphoma; or Subcutaneous panniculitis-like T-cell lymphoma.

In one embodiment, the isolated Compound 2 Form B as disclosed herein, or its salt, prodrug, or isotopic variant can be used in an effective amount to treat a host, for example a human, with a lymphoma or lymphocytic or myelocytic proliferation disorder or abnormality. For example, the isolated Compound 2 Form B as described herein can be administered to a host suffering from a Hodgkin Lymphoma or a Non-Hodgkin Lymphoma. For example, the host can be suffering from a Non-Hodgkin Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non-Cleaved Cell Lymphoma); Chronic Lymphocytic Leukemia/Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; or Waldenstrom's Macroglobulinemia.

Alternatively, the isolated Compound 2 Form B disclosed herein, or its salt, prodrug, or isotopic variant can be used in an effective amount to treat a host, for example a human, with a Hodgkin Lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin Lymphoma; or Nodular Lymphocyte Predominant HL.

Alternatively, the isolated Compound 2 Form B disclosed herein, or its salt, prodrug, or isotopic variant can be used in an effective amount to treat a host, for example a human with a specific B-cell lymphoma or proliferative disorder such as, but not limited to: multiple myeloma; Diffuse large B cell lymphoma; Follicular lymphoma; Mucosa-Associated Lymphatic Tissue lymphoma (MALT); Small cell lymphocytic lymphoma; Mediastinal large B cell lymphoma; Nodal marginal zone B cell lymphoma (NMZL); Splenic marginal zone lymphoma (SMZL); Intravascular large B-cell lymphoma; Primary effusion lymphoma; or Lymphomatoid granulomatosis; B-cell prolymphocytic leukemia; Hairy cell leukemia; Splenic lymphoma/leukemia, unclassifiable; Splenic diffuse red pulp small B-cell lymphoma; Hairy cell leukemia-variant; Lymphoplasmacytic lymphoma; Heavy chain diseases, for example, Alpha heavy chain disease, Gamma heavy chain disease, Mu heavy chain disease; Plasma cell myeloma; Solitary plasmacytoma of bone; Extraosseous plasmacytoma; Primary cutaneous follicle center lymphoma; T cell/histiocyte rich large B-cell lymphoma; DLBCL associated with chronic inflammation; Epstein-Barr virus (EBV)+ DLBCL of the elderly; Primary mediastinal (thymic) large B-cell lymphoma; Primary cutaneous DLBCL, leg type; ALK+ large B-cell lymphoma; Plasmablastic lymphoma; Large B-cell lymphoma arising in HHV8-associated multicentric; Castleman disease; B-cell lymphoma, unclassifiable, with features intermediate between diffuse large B-cell lymphoma; or B-cell lymphoma, unclassifiable, with features intermediate between diffuse large B-cell lymphoma and classical Hodgkin lymphoma.

In one embodiment, the isolated Compound 2 Form B disclosed herein, or its salt, prodrug, or isotopic variant can be used in an effective amount to treat a host, for example a human with leukemia. For example, the host may be suffering from an acute or chronic leukemia of a lymphocytic or myelogenous origin, such as, but not limited to: Acute lymphoblastic leukemia (ALL); Acute myelogenous leukemia (AML); Chronic lymphocytic leukemia (CLL); Chronic myelogenous leukemia (CIVIL); juvenile myelomonocytic leukemia (JMML); hairy cell leukemia (HCL); acute promyelocytic leukemia (a subtype of AML); large granular lymphocytic leukemia; or Adult T-cell chronic leukemia. In one embodiment, the patient suffers from an acute myelogenous leukemia, for example an undifferentiated AML (M0); myeloblastic leukemia (M1; with/without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryoblastic leukemia (M7).

In an alternative embodiment Compound 2 Form A or D is administered in an effective amount to treat a host, typically a human, with a selected cancer, tumor, hyperproliferative condition or an inflammatory or immune disorder. Given the paucity of drugs for T-cell cancers and abnormal proliferation, the identification of such uses represents a substantial improvement in the medical therapy for these diseases.

In an alternative embodiment Compound 2 Form C, E, G, or H is administered in an effective amount to treat a host, typically a human, with a selected cancer, tumor, hyperproliferative condition or an inflammatory or immune disorder. Given the paucity of drugs for T-cell cancers and abnormal proliferation, the identification of such uses represents a substantial improvement in the medical therapy for these diseases.

Pharmaceutical Compositions and Dosage Forms

The isolated Compound 2 Form B described herein, or an alternative salt, isotopic analog, or prodrug can be administered in an effective amount to a host to treat any of the disorders described herein using any suitable approach which achieves the desired therapeutic result. The amount and timing of the isolated Compound 2 Form B administered will, of course, be dependent on the host being treated, the instructions of the supervising medical specialist, on the time course of the exposure, on the manner of administration, on the pharmacokinetic properties of the particular active compound, and on the judgment of the prescribing physician. Thus, because of host to host variability, the dosages given below are a guideline and the physician can titrate doses of the compound to achieve the treatment that the physician considers appropriate for the host. In considering the degree of treatment desired, the physician can balance a variety of factors such as age and weight of the host, presence of preexisting disease, as well as presence of other diseases.

The pharmaceutical composition may be formulated as any pharmaceutically useful form, e.g., a pill, a capsule, a tablet, a transdermal patch, a subcutaneous patch, a dry powder, an inhalation formulation, in a medical device, suppository, buccal, or sublingual formulation. Some dosage forms, such as tablets and capsules, are subdivided into suitably sized unit doses containing appropriate quantities of the active components, e.g., an effective amount to achieve the desired purpose.

The therapeutically effective dosage of the isolated Compound 2 Form B described herein will be determined by the health care practitioner depending on the condition, size and age of the patient as well as the route of delivery. In one non-limited embodiment, a dosage from about 0.1 to about 200 mg/kg has therapeutic efficacy, with all weights being calculated based upon the weight of the active compound. In some embodiments, the dosage may be the amount of the isolated Compound 2 Form B needed to provide a serum concentration of the active compound of up to about 10 nM, 50 nM, 100 nM, 200 nM, 300 nM, 400 nM, 500 nM, 600 nM, 700 nM, 800 nM, 900 nM, 1 µM, 5 µM, 10 µM, 20 µM, 30 µM, or 40 µM.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of the isolated Compound 2 Form B, measured alternatively either as the active compound or its salt, in a unit dosage form. Examples of dosage forms with at least 5, 10, 15, 20, 25, 50, 100, 200, 250, 300, 400, 500, 600, 700, or 750 mg of active compound, or its salt. The pharmaceutical composition may also include a molar ratio of the isolated Compound 2 Form B and an additional active agent, in a ratio that achieves the desired results.

The isolated Compound 2 Form B disclosed herein or used as described herein may be administered orally, topically, parenterally, by inhalation or spray, sublingually, via implant, including ocular implant, transdermally, via buccal administration, rectally, intramuscular, inhalation, intra-aortal, intracranial, subdermal, intraperitoneal, subcutaneous, transnasal, sublingual, or rectal or by other means, in dosage unit formulations containing conventional pharmaceutically acceptable carriers.

In accordance with the presently disclosed methods, an oral administration can be in any desired form in which the isolated Compound 2 Form B is stable as a solid. In certain embodiments, the isolated Compound 2 Form B is delivered in a solid microparticle or nanoparticle. When administered through inhalation the isolated Compound 2 Form B may be in the form of a plurality of solid particles or droplets having any desired particle size, and for example, from about 0.01, 0.1 or 0.5 to about 5, 10, 20 or more microns, and optionally from about 1 to about 2 microns. The isolated Compound 2 Form B as disclosed in the present invention has good pharmacokinetic and pharmacodynamics properties, for instance when administered by the oral or intravenous routes.

The pharmaceutical formulations can comprise the isolated Compound 2 Form B described herein or an alternative pharmaceutically acceptable salt thereof, in any pharmaceutically acceptable carrier.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

Depending on the intended mode of administration, the pharmaceutical compositions can be in the form of solid form or a semi-solid dosage form that the isolated Compound 2 Form B is stable in, such as, for example, tablets, suppositories, pills, capsules, powders, or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, and the like.

Thus, the compositions of the disclosure can be administered as pharmaceutical formulations including those suitable for oral (including buccal and sub-lingual), rectal, nasal, topical, pulmonary, vaginal administration or in a form suitable for administration by inhalation or insufflation. The preferred manner of administration is oral using a convenient daily dosage regimen which can be adjusted according to the degree of affliction. For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like.

In yet another embodiment is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally take the form of a tablet or capsule. Tablets and capsules are preferred oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like.

Disintegrators include, without limitation, starch, methyl cellulose, agar, bentonite, xanthan gum, and the like.

In addition to the active compounds or their salts, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. An antimicrobial preservative is typically employed when the formulations is placed in a vial designed for multi-dose use. The pharmaceutical formulations described herein can be lyophilized using techniques well known in the art.

For oral administration a pharmaceutical composition can take the form of a tablet, pill, capsule, powder, and the like. Tablets containing various excipients such as sodium citrate, calcium carbonate and calcium phosphate may be employed along with various disintegrants such as starch (e.g., potato or tapioca starch) and certain complex silicates, together with binding agents such as polyvinylpyrrolidone, sucrose, gelatin and acacia. Additionally, lubricating agents such as magnesium stearate, sodium lauryl sulfate, and talc are often very useful for tableting purposes. Solid compositions of a similar type may be employed as fillers in soft and hard-filled gelatin capsules.

Pharmaceutical formulations also are provided which provide a controlled release of a compound described herein, including through the use of a degradable polymer, as known in the art.

The term "pharmaceutically acceptable salts" as used herein refers to those salts which are, within the scope of sound medical judgment, suitable for use in contact with hosts (e.g., human hosts) without undue toxicity, irritation, allergic response, and the like, commensurate with a reasonable benefit/risk ratio, and effective for their intended use, as well as the zwitterionic forms, where possible, of the compounds of the presently disclosed host matter.

In an alternative embodiment Compound 2 morphic form B is not a HCl salt, but is instead a salt described below.

In one embodiment the additional therapeutic agent described in the Combination Section below is administered as a pharmaceutically acceptable salt, for example, a salt described below. Thus, the term "salts" refers to the relatively non-toxic, inorganic and organic acid addition salts of the presently disclosed compounds. These salts can be prepared during the final isolation and purification of the compounds or by separately reacting the purified compound in its free base form with a suitable organic or inorganic acid and isolating the salt thus formed. Basic compounds are capable of forming a wide variety of different salts with various inorganic and organic acids. Acid addition salts of the basic compounds are prepared by contacting the free base form with a sufficient amount of the desired acid to produce the salt in the conventional manner. The free base form can be regenerated by contacting the salt form with a base and isolating the free base in the conventional manner. The free base forms may differ from their respective salt forms in certain physical properties such as solubility in polar solvents. Pharmaceutically acceptable base addition salts may be formed with metals or amines, such as alkali and alkaline earth metal hydroxides, or of organic amines. Examples of metals used as cations, include, but are not limited to, sodium, potassium, magnesium, calcium, and the like. Examples of suitable amines include, but are not limited to, N,N'-dibenzylethylenediamine, chloroprocaine, choline, diethanolamine, ethylenediamine, N-methylglucamine, and procaine. The base addition salts of acidic compounds are prepared by contacting the free acid form with a sufficient amount of the desired base to produce the salt in the conventional manner. The free acid form can be regenerated by contacting the salt form with an acid and isolating the free acid in a conventional manner. The free acid forms may differ from their respective salt forms somewhat in certain physical properties such as solubility in polar solvents.

Salts can be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide such as hydrochloric, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts can also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like.

Pharmaceutically acceptable salts can include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. See, for example, Berge et al., J. Pharm. Sci., 1977, 66, 1-19, which is incorporated herein by reference.

Formulations suitable for rectal administration are typically presented as unit dose suppositories. These may be prepared by admixing the active disclosed compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil, which maintain the stability of the isolated Compound 2 Form B. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

In an alternative embodiment, Compound 2 Form B is an HCl salt, for example a mono-hydrochloride salt, an HCl salt with about 1 hydrochloride units per Compound 2 unit, about 1.5 hydrochloride units per Compound 2 unit, or about 2 hydrochloride units per Compound 2 unit.

In one embodiment, "about" means ±1%, 2%, 3%, 4%, 5%, 6%, 7%, 8%, 9%, or 10%. In one embodiment, Compound 2 Form B has about 2 HCl ions per Compound 2 molecule.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Combination Therapy

Isolated Compound 2 morphic Form B can be used in an effective amount alone or in combination with another compound of the present invention or another bioactive agent to treat a host such as a human with a disorder as described herein.

The isolated Compound 2 Form B described herein can be used in an effective amount alone or in combination with another compound of the present invention or another bioactive agent to treat a host such as a human with a disorder as described herein.

The term "bioactive agent" is used to describe an agent, other than the selected compound according to the present invention, which can be used in combination or alternation with a compound of the present invention to achieve a desired result of therapy. In one embodiment, the compound of the present invention and the bioactive agent are administered in a manner that they are active in vivo during overlapping time periods, for example, have time-period overlapping Cmax, Tmax, AUC or other pharmacokinetic parameter. In another embodiment, isolated Compound 2 Form B and the bioactive agent are administered to a host in need thereof that do not have overlapping pharmacokinetic parameter, however, one has a therapeutic impact on the therapeutic efficacy of the other.

In one aspect of this embodiment, the bioactive agent is an immune modulator, including but not limited to a checkpoint inhibitor, including as non-limiting examples, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or other inhibitor. In certain aspects, the immune modulator is an antibody, such as a monoclonal antibody.

PD-1 inhibitors that blocks the interaction of PD-1 and PD-L1 by binding to the PD-1 receptor, and in turn inhibit immune suppression include, for example, nivolumab (Opdivo), pembrolizumab (Keytruda), pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-L1/VISTA inhibitor CA-170 (Curis Inc.). PD-L1 inhibitors that block the interaction of PD-1 and PD-L1 by binding to the PD-L1 receptor, and in turn inhibits immune suppression, include for example, atezolizumab (Tecentriq), durvalumab (AstraZeneca and MedImmune), KN035 (Alphamab), and BMS-936559 (Bristol-Myers Squibb). CTLA-4 checkpoint inhibitors that bind to CTLA-4 and inhibits immune suppression include, but are not limited to, ipilimumab, tremelimumab (AstraZeneca and MedImmune), AGEN1884 and AGEN2041 (Agenus). LAG-3 checkpoint inhibitors, include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics). An example of a TIM-3 inhibitor is TSR-022 (Tesaro).

In yet another embodiment, isolated Compound 2 Form B as described herein can be administered in an effective amount for the treatment of abnormal tissue of the female reproductive system such as breast, ovarian, endometrial, or uterine cancer, in combination or alternation with an effective amount of an estrogen inhibitor including but not limited to a SERM (selective estrogen receptor modulator), a SERD (selective estrogen receptor degrader), a complete estrogen receptor degrader, or another form of partial or complete estrogen antagonist or agonist. Partial anti-estrogens like raloxifene and tamoxifen retain some estrogen-like effects, including an estrogen-like stimulation of uterine growth, and also, in some cases, an estrogen-like action during breast cancer progression which actually stimulates tumor growth. In contrast, fulvestrant, a complete anti-estrogen, is free of estrogen-like action on the uterus and is effective in tamoxifen-resistant tumors. Non-limiting examples of anti-estrogen compounds are provided in WO 2014/19176 assigned to Astra Zeneca, WO2013/090921, WO 2014/203129, WO 2014/203132, and US2013/0178445 assigned to Olema Pharmaceuticals, and U.S. Pat. Nos. 9,078,871, 8,853,423, and 8,703, 810, as well as US 2015/0005286, WO 2014/205136, and WO 2014/205138.

Additional non-limiting examples of anti-estrogen compounds include: SERMS such as anordrin, bazedoxifene, broparestriol, chlorotrianisene, clomiphene citrate, cyclofenil, lasofoxifene, ormeloxifene, raloxifene, tamoxifen, toremifene, and fulvestrant; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, cyproterone acetate, delmadinone acetate, dydrogesterone, medroxyprogesterone acetate, megestrol acetate, nomegestrol acetate, norethisterone acetate, progesterone, and spironolactone. Other estrogenic ligands that can be used according to the present invention are described in U.S. Pat. Nos. 4,418,068; 5,478,847; 5,393,763; and 5,457,117, WO2011/156518, U.S. Pat. Nos. 8,455,534 and 8,299,112, 9,078,871; 8,853,423; 8,703,810; US 2015/0005286; and WO 2014/205138, US2016/0175289, US2015/0258080, WO 2014/191726, WO 2012/084711; WO 2002/013802; WO 2002/004418; WO 2002/003992; WO 2002/003991; WO 2002/003990; WO 2002/003989; WO 2002/003988; WO 2002/003986; WO 2002/003977; WO 2002/003976; WO 2002/003975; WO 2006/078834; US 6821989; US 2002/0128276; US 6777424; US 2002/0016340; U.S. Pat. Nos. 6,326,392; 6,756,401; US 2002/0013327; U.S. Pat. Nos. 6,512,002; 6,632,834; US 2001/0056099; US 6583170; U.S. Pat. No. 6,479,535; WO 1999/024027; U.S. Pat. No. 6,005,102; EP 0802184; U.S. Pat. Nos. 5,998,402; 5,780,497, 5,880,137, WO 2012/048058 and WO 2007/087684.

In another embodiment, the isolated Compound 2 Form B described herein can be administered in an effective amount for the treatment of abnormal tissue of the male reproductive system such as prostate or testicular cancer, in combination or alternation with an effective amount of an androgen (such as testosterone) inhibitor including but not limited to a selective androgen receptor modulator, a selective androgen receptor degrader, a complete androgen receptor degrader, or another form of partial or complete androgen antagonist. In one embodiment, the prostate or testicular cancer is androgen-resistant. Non-limiting examples of anti-androgen compounds are provided in WO 2011/156518 and U.S. Pat. Nos. 8,455,534 and 8,299,112. Additional non-limiting examples of anti-androgen compounds include: enzalutamide, apalutamide, cyproterone acetate, chlormadinone acetate, spironolactone, canrenone, drospirenone, ketoconazole, topilutamide, abiraterone acetate, and cimetidine.

In one embodiment, an effective amount of Compound 2 Form B is administered in combination with an effective amount of abiraterone acetate (Zytiga) for the treatment of abnormal tissue of the male reproductive system.

In one embodiment, an effective amount of Compound 2 Form B is administered in combination with an effective amount of abiraterone acetate (Zytiga) for the treatment of prostate cancer.

In one embodiment, an effective amount of Compound 2 Form B is administered in combination with an effective amount of enzalutamide for the treatment of prostate cancer.

In one embodiment, the bioactive agent is an ALK inhibitor. Examples of ALK inhibitors include but are not limited to Crizotinib, Alectinib, ceritinib, TAE684 (NVP-TAE684), GSK1838705A, AZD3463, ASP3026, PF-06463922, entrectinib (RXDX-101), and AP26113. In one embodiment, the bioactive agent is an EGFR inhibitor. Examples of EGFR inhibitors include erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EA1045, tarloxotinib (TH-4000; PR-610), PF-06459988 (Pfizer), tesevatinib (XL647; EXEL-7647; KD-019), transtinib, WZ-3146, WZ8040, CNX-2006, dacomitinib (PF-00299804; Pfizer), brigatinib (Alunbrig), lorlatinib, and PF-06747775 (PF7775).

In one embodiment, an effective amount of Compound 2 Form B is administered in combination with an effective amount of afatinib dimaleate (Gilotrif) for the treatment of non-small cell lung cancer.

In one embodiment, an effective amount of Compound 2 Form B is administered in combination with an effective amount of alectinib (Alecensa) for the treatment of non-small cell lung cancer.

In one embodiment, an effective amount of Compound 2 Form B is administered in combination with an effective amount of ceritinib (Zykadia) for the treatment of non-small cell lung cancer.

In one embodiment, an effective amount of Compound 2 Form B is administered in combination with an effective amount of crizotinib (Xalkori) for the treatment of non-small cell lung cancer.

In one embodiment, an effective amount of Compound 2 Form B is administered in combination with an effective amount of osimertinib (Tagrisso) for the treatment of non-small cell lung cancer.

In one embodiment, an effective amount of Compound 2 Form B is administered in combination with an effective amount of brigatinib (Alunbrig) for the treatment of non-small cell lung cancer.

In one embodiment, an effective amount of Compound 2 Form B is administered in combination with an effective amount of lorlatinib for the treatment of non-small cell lung cancer.

In one embodiment, the bioactive agent is an HER-2 inhibitor. Examples of HER-2 inhibitors include trastuzumab, lapatinib, ado-trastuzumab emtansine, and pertuzumab.

In one embodiment, an effective amount of Compound 2 Form B is administered in combination with an effective amount of lapatinib ditosylate for the treatment of breast cancer.

In one embodiment, an effective amount of Compound 2 Form B is administered in combination with an effective amount of lapatinib ditosylate for the treatment of HER2+ breast cancer.

In one embodiment, an effective amount of Compound 2 Form B is administered in combination with an effective amount of PF7775 for the treatment of non-small cell lung cancer.

In one embodiment, the bioactive agent is a CD20 inhibitor. Examples of CD20 inhibitors include obinutuzumab, rituximab, fatumumab, ibritumomab, tositumomab, and ocrelizumab.

In one embodiment, the bioactive agent is a JAK3 inhibitor. Examples of JAK3 inhibitors include tasocitinib.

In one embodiment, the bioactive agent is a BCL-2 inhibitor. Examples of BCL-2 inhibitors include venetoclax, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide) (navitoclax), ABT-263 ((R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl)phenyl]sulfonyl]phenyl]-2,3,4-trihydroxy-5-[[2-(1-methylethyl)phenyl]methyl]benzamide), Apogossypolone (ApoG2), HA14-1, AT101, sabutoclax, gambogic acid, or G3139 (Oblimersen).

In one aspect, a treatment regimen is provided comprising the administration of Compound 2 morphic Form B in combination with at least one additional chemotherapeutic agent. The combinations disclosed herein can be administered for beneficial, additive, or synergistic effect in the treatment of abnormal cellular proliferative disorders.

In specific embodiments, the treatment regimen includes the administration of isolated Compound 2 morphic Form B in combination with at least one kinase inhibitor. In one embodiment, the at least one kinase inhibitor is selected from a phosphoinositide 3-kinase (PI3K) inhibitor, a Bruton's tyrosine kinase (BTK) inhibitor, or a spleen tyrosine kinase (Syk) inhibitor, or a combination thereof.

PI3k inhibitors that may be used in the present invention are well known. Examples of PI3 kinase inhibitors include but are not limited to Wortmannin, demethoxyviridin, perifosine, idelalisib, Pictilisib, Palomid 529, ZSTK474, PWT33597, CUDC-907, and AEZS-136, duvelisib, GS-9820, BKM120, GDC-0032 (Taselisib), (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo){[(2R)-1-phenoxy-2-butanyl]oxy}phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide) (omipalisib), TGX-221 ((±)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl)phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide), Buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl) thieno[3,2-d]pyrimidine), GDC-0980 ((S)-1-(4-((2-(2-aminopyrimidin-5-yl)-7-methyl-4-morpholinothieno[3,2-d] pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate), PF-05212384 (N-[4-[[4-(Dimethylamino)-1-piperidinyl]carbonyl]phenyl]-N'-[4-(4,6-di-4-morpholinyl-1,3,5-triazin-2-yl)phenyl]urea) (gedatolisib), LY3023414, BEZ235 (2-Methyl-2-{4-[3-methyl-2-oxo-8-(quinolin-3-yl)-2,3-dihydro-1H-imidazo[4,5-c]quinolin-1-yl]phenyl}propanenitrile) (dactolisib), XL-765 (N-(3-(N-(3-(3,5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R,11aS)-6-[[bis(prop-2-enyl)amino] methylidene]-5-hydroxy-9-(methoxymethyl)-9a,11a-dimethyl-1,4,7-trioxo-2,3,3a,9,10,11-hexahydroindeno[4,5h]isochromen-10-yl] acetate (also known as sonolisib)) LY294002, AZD8186, PF-4989216, pilaralisib, GNE-317, PI-3065, PI-103, NU7441 (KU-57788), HS 173, VS-5584 (SB2343), CZC24832, TG100-115, A66, YM201636, CAY10505, PIK-75, PIK-93, AS-605240, BGT226 (NVP-BGT226), AZD6482, voxtalisib, alpelisib, IC-87114, TGI100713, CH5132799, PKI-402, copanlisib (BAY 80-6946), XL 147, PIK-90, PIK-293, PIK-294, 3-MA (3-methyladenine), AS-252424, AS-604850, apitolisib (GDC-0980; RG7422), and the structures described in WO2014/071109. In one embodiment, isolated Compound 2 Form B is combined in a single dosage form with the PIk3 inhibitor.

In one embodiment, an effective amount of Compound 2 Form B is administered in combination with an effective amount of alpelisib for the treatment of solid tumors.

In one embodiment, an effective amount of Compound 2 Form B is administered in combination with an effective amount of alpelisib for the treatment of abnormal tissue of the female reproductive system.

In one embodiment, an effective amount of Compound 2 Form B is administered in combination with an effective amount of alpelisib for the treatment of breast cancer.

In one embodiment, an effective amount of Compound 2 Form B is administered in combination with an effective amount of copanlisib hydrochloride (Aliqopa) for the treatment of lymphoma.

In one embodiment, an effective amount of Compound 2 Form B is administered in combination with an effective amount of copanlisib hydrochloride (Aliqopa) for the treatment of follicular lymphoma.

In one embodiment, an effective amount of Compound 2 Form B is administered in combination with an effective amount of idelalisib (Zydelig) for the treatment of chronic lymphocytic leukemia.

In one embodiment, an effective amount of Compound 2 Form B is administered in combination with an effective amount of idelalisib (Zydelig) for the treatment of Non-Hodgkin lymphoma, including follicular B-cell non-Hodgkin lymphoma or small lymphocytic lymphoma.

BTK inhibitors for use in the present invention are well known. Examples of BTK inhibitors include ibrutinib (also known as PCI-32765)(Imbruvica™)(1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 2011/0117073, incorporated herein in its entirety), Dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl) phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g] quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino) pyrimidine-5-carboxamide hydrochloride), QL-47 (1-(1-acryloylindolin-6-yl)-9-(1-methyl-1H-pyrazol-4-yl)benzo

[h][1,6]naphthyridin-2(1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, Journal of Hematology & Oncology, 2013, 6:59, the entirety of which is incorporated herein by reference. In one embodiment, an effective amount of the isolated Compound 2 Form B is combined in a single dosage form with the BTK inhibitor.

In one embodiment, an effective amount of Compound 2 Form B is administered in combination with an effective amount of ibrutinib (Imbruvica) for the treatment of chronic lymphocytic leukemia.

In one embodiment, an effective amount of Compound 2 Form B is administered in combination with an effective amount of ibrutinib (Imbruvica) for the treatment of lymphoma, including small lymphocytic lymphoma, mantle cell lymphoma, marginal zone lymphoma, or Waldenström macroglobulinemia.

Syk inhibitors for use in the present invention are well known, and include, for example, Cerdulatinib (4-(cyclopropylamino)-2-((4-(4-(ethylsulfonyl)piperazin-1-yl)phenyl)amino)pyrimidine-5-carboxamide), entospletinib (6-(1H-indazol-6-yl)-N-(4-morpholinophenyl)imidazo[1,2-a]pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate), fostamatinib disodium salt (sodium (6-((5-fluoro-2-((3,4,5-trimethoxyphenyl)amino)pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), RO9021 (6-[(1R,2S)-2-Amino-cyclohexylamino]-4-(5,6-dimethyl-pyridin-2-ylamino)-pyridazine-3-carboxylic acid amide), imatinib (Gleevac; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R,2S)-2-aminocyclohexyl)amino)-4-(m-tolylamino)pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'-((5-fluoropyrimidine-2,4-diyl)bis(azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4]oxazin-3(4H)-one), piceatannol (3-Hydroxyresveratol), YM193306(see Singh et al. Discovery and Development of Spleen Tyrosine Kinase (SYK) Inhibitors, J. Med. Chem. 2012, 55, 3614-3643), 7-azaindole, piceatannol, ER-27319 (see Singh et al. Discovery and Development of Spleen Tyrosine Kinase (SYK) Inhibitors, J. Med. Chem. 2012, 55, 3614-3643 incorporated in its entirety herein), Compound D (see Singh et al. Discovery and Development of Spleen Tyrosine Kinase (SYK) Inhibitors, J. Med. Chem. 2012, 55, 3614-3643 incorporated in its entirety herein), PRT060318 (see Singh et al. Discovery and Development of Spleen Tyrosine Kinase (SYK) Inhibitors, J. Med. Chem. 2012, 55, 3614-3643 incorporated in its entirety herein), luteolin (see Singh et al. Discovery and Development of Spleen Tyrosine Kinase (SYK) Inhibitors, J. Med. Chem. 2012, 55, 3614-3643 incorporated in its entirety herein), apigenin (see Singh et al. Discovery and Development of Spleen Tyrosine Kinase (SYK) Inhibitors, J. Med. Chem. 2012, 55, 3614-3643 incorporated in its entirety herein), quercetin (see Singh et al. Discovery and Development of Spleen Tyrosine Kinase (SYK) Inhibitors, J. Med. Chem. 2012, 55, 3614-3643 incorporated in its entirety herein), fisetin (see Singh et al. Discovery and Development of Spleen Tyrosine Kinase (SYK) Inhibitors, J. Med. Chem. 2012, 55, 3614-3643 incorporated in its entirety herein), myricetin (see Singh et al. Discovery and Development of Spleen Tyrosine Kinase (SYK) Inhibitors, J. Med. Chem. 2012, 55, 3614-3643 incorporated in its entirety herein), morin (see Singh et al. Discovery and Development of Spleen Tyrosine Kinase (SYK) Inhibitors, J. Med. Chem. 2012, 55, 3614-3643 incorporated in its entirety herein). In one embodiment an effective amount of the isolated Compound 2 Form B is combined in a single dosage form with the Syk inhibitor.

In one embodiment, the at least one additional chemotherapeutic agent is a protein cell death-1 (PD-1) inhibitor. PD-1 inhibitors are known in the art, and include, for example, nivolumab (BMS), pembrolizumab (Merck), pidilizumab (CureTech/Teva), AMP-244 (Amplimmune/GSK), BMS-936559 (BMS), and MEDI4736 (Roche/Genentech). In one embodiment, an effective amount of the isolated Compound 2 Form B is combined in a single dosage form with the PD-1 inhibitor.

In an alternative embodiment isolated Compound 2 morphic Form A or D can be used in an effective amount alone or in combination with another compound of the present invention or another bioactive agent to treat a host such as a human with a disorder as described herein.

In one embodiment, the at least one additional chemotherapeutic agent is a B-cell lymphoma 2 (Bcl-2) protein inhibitor. BCL-2 inhibitors are known in the art, and include, for example, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide), ABT-263 ((R)-4-(4-((4'-chloro-4,4-dimethyl-3,4,5,6-tetrahydro-[1, 1'-biphenyl]-2-yl)methyl)piperazin-1-yl)-N-((4-((4-morpholino-1-(phenylthio)butan-2-yl)amino)-3-((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl)phenyl]sulfonyl]phenyl]-2,3,4-trihydroxy-5-[[2-(1-methylethyl)phenyl]methyl]benzamide), Apogossypolone (ApoG2), or G3139 (Oblimersen). In one embodiment, an effective amount of the isolated Compound 2 Form B is combined in a single dosage form with the at least one BCL-2 inhibitor.

In one embodiment, a combination described herein can be further combined with an additional therapeutic to treat the cancer. The second therapy can be an immunotherapy. As discussed in more detail below, an effective amount of the isolated Compound 2 Form B can be conjugated to an antibody, radioactive agent, or other targeting agent that directs the compound to the diseased or abnormally proliferating cell. In another embodiment, the combination is used in combination with another pharmaceutical or a biologic agent (for example an antibody) to increase the efficacy of treatment with a combined or a synergistic approach. In an embodiment, combination can be used with T-cell vaccination, which typically involves immunization with inactivated autoreactive T cells to eliminate a cancer cell population as described herein. In another embodiment, the combination is used in combination with a bispecific T-cell Engager (BiTE), which is an antibody designed to simultaneously bind to specific antigens on endogenous T cells and cancer cells as described herein, linking the two types of cells.

In one embodiment, the bioactive agent is a MEK inhibitor. MEK inhibitors are well known, and include, for example, trametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl) acetamide), selumetinib (6-(4-bromo-2-chloroanilino)-7-fluoro-N-(2-hydroxyethoxy)-3-methylbenzimidazole-5-carboxamide), pimasertib/AS703026/MSC 1935369 ((S)—N-(2,3-dihydroxypropyl)-3-((2-fluoro-4-iodophenyl)amino) isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEA1 19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), RO5126766 (3-[[3-Fluoro-2-(methylsulfamoylamino)-4-pyridyl]methyl]-4-methyl-7-pyrimidin-2-yloxychromen-2-one), WX-554, RO4987655/CH4987655 (3,4-difluoro-2-((2-fluoro-4-iodophenyl) amino)-N-(2-hydroxyethoxy)-5-((3-oxo-1,2-oxazinan-2yl) methyl)benzamide), or AZD8330 (2-((2-fluoro-4-iodophenyl)amino)-N-(2 hydroxyethoxy)-1,5-dimethyl-6-oxo-1,6-dihydropyridine-3-carboxamide), U0126-EtOH, PD184352 (CI-1040), GDC-0623, BI-847325, cobimetinib, PD98059, BIX 02189, BIX 02188, binimetinib, SL-327, TAK-733, PD318088.

In one embodiment, an effective amount of Compound 2 Form B is administered in combination with an effective amount of binimetinib for the treatment of melanoma, including BRAF-mutant melanoma and NRAS-mutant melanoma.

In one embodiment, an effective amount of Compound 2 Form B is administered in combination with an effective amount of cobimetinib (Cotellic) for the treatment of melanoma, including BRAF-mutant melanoma and NRAS-mutant melanoma.

In one embodiment, an effective amount of Compound 2 Form B is administered in combination with an effective amount of binimetinib for the treatment of ovarian cancer.

In one embodiment, an effective amount of Compound 2 Form B is administered in combination with an effective amount of selumetinib for the treatment of non-small cell lung cancer.

In one embodiment, an effective amount of Compound 2 Form B is administered in combination with an effective amount of selumetinib for the treatment of thyroid cancer.

In one embodiment, an effective amount of Compound 2 Form B is administered in combination with an effective amount of trametinib (Mekinist) for the treatment of thyroid cancer.

In one embodiment, an effective amount of Compound 2 Form B is administered in combination with an effective amount of trametinib (Mekinist) for the treatment of melanoma.

In one embodiment, an effective amount of Compound 2 Form B is administered in combination with an effective amount of trametinib (Mekinist) for the treatment of non-small cell lung cancer.

In one embodiment, the bioactive agent is a Raf inhibitor. Raf inhibitors are known and include, for example, Vemurafinib (N-[3-[[5-(4-Chlorophenyl)-1H-pyrrolo[2,3-b]pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carboxamide;4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265 (1-methyl-5-[2-[5-(trifluoromethyl)-1H-imidazol-2-yl]pyridin-4-yl]oxy-N-[4-(trifluoromethyl)phenyl]benzimidazol-2-amine), 2-Bromoaldisine (2-Bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), Sorafenib N-Oxide (4-[4-[[[[4-Chloro-3(trifluoroMethyl) phenyl]aMino]carbonyl]aMino]phenoxy]-N-Methyl-2pyridinecarboxaMide 1-Oxide), PLX-4720, dabrafenib (GSK2118436), GDC-0879, RAF265, AZ 628, SB590885, ZM336372, GW5074, TAK-632, CEP-32496, LY3009120, and GX818 (Encorafenib).

In one embodiment, an effective amount of Compound 2 Form B is administered in combination with an effective amount of dabrafenib (Tafinlar) for the treatment of thyroid cancer.

In one embodiment, an effective amount of Compound 2 Form B is administered in combination with an effective amount of dabrafenib (Tafinlar) for the treatment of melanoma.

In one embodiment, an effective amount of Compound 2 Form B is administered in combination with an effective amount of dabrafenib (Tafinlar) for the treatment of non-small cell lung cancer.

In one embodiment, an effective amount of Compound 2 Form B is administered in combination with an effective amount of encorafenib for the treatment of melanoma, including BRAF-mutant melanoma.

In one embodiment, the additional therapy is a monoclonal antibody (MAb). Some MAbs stimulate an immune response that destroys cancer cells. Similar to the antibodies produced naturally by B cells, these MAbs "coat" the cancer cell surface, triggering its destruction by the immune system. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs that bind to cell surface growth factor receptors prevent the targeted receptors from sending their normal growth-promoting signals. They may also trigger apoptosis and activate the immune system to destroy tumor cells.

Another group of cancer therapeutic MAbs are the immunoconjugates. These MAbs, which are sometimes called immunotoxins or antibody-drug conjugates, consist of an antibody attached to a cell-killing substance, such as a plant or bacterial toxin, a chemotherapy drug, or a radioactive molecule. The antibody latches onto its specific antigen on the surface of a cancer cell, and the cell-killing substance is taken up by the cell. FDA-approved conjugated MAbs that work this way include ado-trastuzumab emtansine, which targets the HER-2 molecule to deliver the drug DM1, which inhibits cell proliferation, to HER-2 expressing metastatic breast cancer cells.

Immunotherapies with T cells engineered to recognize cancer cells via bispecific antibodies (bsAbs) or chimeric antigen receptors (CARs) are approaches with potential to ablate both dividing and non/slow-dividing subpopulations of cancer cells.

Bispecific antibodies, by simultaneously recognizing target antigen and an activating receptor on the surface of an immune effector cell, offer an opportunity to redirect immune effector cells to kill cancer cells. The other approach is the generation of chimeric antigen receptors by fusing extracellular antibodies to intracellular signaling domains. Chimeric antigen receptor-engineered T cells are able to specifically kill tumor cells in a MHC-independent way.

In some embodiments, the combination can be administered to the subject in further combination with other chemotherapeutic agents. If convenient, the combination described herein can be administered at the same time as another chemotherapeutic agent, in order to simplify the treatment regimen. In some embodiments, the combination and the other chemotherapeutic can be provided in a single formulation. In one embodiment, the use of the compounds described herein is combined in a therapeutic regime with other agents. Such agents may include, but are not limited to, tamoxifen, midazolam, letrozole, bortezomib, anastrozole, goserelin, an mTOR inhibitor, a PI3 kinase inhibitors, dual mTOR-PI3K inhibitors, MEK inhibitors, RAS inhibitors, ALK inhibitors, HSP inhibitors (for example, HSP70 and HSP 90 inhibitors, or a combination thereof), BCL-2 inhibitors, apoptotic inducing compounds, AKT inhibitors, including but not limited to, MK-2206, GSK690693, Perifosine, (KRX-0401), GDC-0068, Triciribine, AZD5363, Honokiol, PF-04691502, and ipatasertib, Miltefosine; PD-1 inhibitors including but not limited to, Nivolumab, CT-011, MK-3475, BMS936558, and AMP-514 or FLT-3 inhibitors, including but not limited to, P406, Dovitinib, Quizartinib (AC220), Amuvatinib (MP-470), Tandutinib (MLN518), ENMD-2076, and KW-2449, or combinations thereof.

In one embodiment, an effective amount of Compound 2 Form B is administered in combination with an effective amount of ipatasertib for the treatment of breast cancer, including triple negative breast cancer.

In one embodiment, the bioactive agent is an mTOR inhibitor. Examples of mTOR inhibitors include but are not limited to vistusertib and rapamycin and its analogs, everolimus (Afinitor), temsirolimus, ridaforolimus, sirolimus, and deforolimus. Examples of MEK inhibitors include but are not limited to tametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinob (6-(4-bromo-2-chloroanilino)-7-fluoro-N-(2-hydroxyethoxy)-3-methylbenzimidazole-5-carboxamide), pimasertib/AS703026/MSC1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl] azetidin-3-ol), refametinib/BAY869766/RDEA119 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3d]pyrimidine-4,7 (3H,8H)-dione), MEK162/ARRY438162 (5-[(4-Bromo-2-fluorophenyl)amino]-4-fluoro-N-(2-hydroxyethoxy)-1-methyl-1H-benzimidazole-6 carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2 yl)methyl)benzamide), or AZD8330 (2-((2-fluoro-4-iodophenyl)amino)-N-(2-hydroxyethoxy)-1,5-dimethyl-6-oxo-1,6-dihydropyridine-3-carboxamide).

In one embodiment, the bioactive agent is a RAS inhibitor. Examples of RAS inhibitors include but are not limited to Reolysin and siG12D LODER.

In one embodiment, the bioactive agent is an ALK inhibitor. Examples of ALK inhibitors include but are not limited to Crizotinib, AP26113, and LDK378.

In one embodiment, the bioactive agent is a HSP inhibitor. HSP inhibitors include but are not limited to Geldanamycin or 17-N-Allylamino-17-demethoxygeldanamycin (17AAG), and Radicicol. In a particular embodiment, a compound described herein is administered in combination with letrozole and/or tamoxifen. Other chemotherapeutic agents that can be used in combination with the compounds described herein include, but are not limited to, chemotherapeutic agents that do not require cell cycle activity for their anti-neoplastic effect.

Additional bioactive compounds include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an aurora kinase inhibitor, a PIK-1 modulator, an HDAC inhibitor, a c-MET inhibitor, a PARP inhibitor, a Cdk inhibitor, an IGFR-TK inhibitor, an anti-HGF antibody, a focal adhesion kinase inhibitor, a Map kinase (mek) inhibitor, a VEGF trap antibody, pemetrexed, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdRi KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methyl sulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, a platelet-derived growth factor receptor alpha (PDGFR-α) antibody, epoetin alfa, darbepoetin alfa and mixtures thereof.

In one embodiment, an effective amount of the isolated Compound 2 Form B described herein can be combined with a PARP inhibitor selected from niraparib tosylate monohydrate (Zejula), olaparib (Lynparza), rucaparib camsylate (Rubraca), and talazoparib.

In one embodiment, an effective amount of Compound 2 Form B is administered in combination with an effective amount of niraparib tosylate monohydrate (Zejula) for the treatment of abnormal tissue of the female reproductive system, including ovarian epithelial cancer or fallopian tube cancer.

In one embodiment, an effective amount of Compound 2 Form B is administered in combination with an effective amount of niraparib tosylate monohydrate (Zejula) for the treatment of peritoneal cancer.

In one embodiment, an effective amount of Compound 2 Form B is administered in combination with an effective amount of olaparib (Lynparza) for the treatment of abnormal tissue of the female reproductive system, including breast cancer, ovarian cancer, ovarian epithelial cancer or fallopian tube cancer.

In one embodiment, an effective amount of Compound 2 Form B is administered in combination with an effective amount of olaparib (Lynparza) for the treatment of BRAC1 or BRAC2-mutated breast cancer.

In one embodiment, an effective amount of Compound 2 Form B is administered in combination with an effective amount of olaparib (Lynparza) for the treatment of HER2– breast cancer.

In one embodiment, an effective amount of Compound 2 Form B is administered in combination with an effective amount of olaparib (Lynparza) for the treatment of peritoneal cancer.

In one embodiment, an effective amount of Compound 2 Form B is administered in combination with an effective amount of rucaparib camsylate (Rubraca) for the treatment of abnormal tissue of the female reproductive system, including breast cancer, ovarian cancer, ovarian epithelial cancer or fallopian tube cancer.

In one embodiment, an effective amount of Compound 2 Form B is administered in combination with an effective amount of rucaparib camsylate (Rubraca) for the treatment of peritoneal cancer.

In one embodiment, an effective amount of Compound 2 Form B is administered in combination with an effective amount of talazoparib for the treatment of abnormal tissue of the female reproductive system, including breast cancer, ovarian cancer, ovarian epithelial cancer or fallopian tube cancer.

In one embodiment, an effective amount of Compound 2 Form B is administered in combination with an effective amount of talazoparib for the treatment of BRAC1 or BRAC2-mutated breast cancer.

In one embodiment, an effective amount of Compound 2 Form B is administered in combination with an effective amount of olaratumab for the treatment of soft tissue sarcoma.

In one embodiment, an effective amount of Compound 2 Form B is administered in combination with an effective amount of savolitinib for the treatment of adenocarcinoma.

In one embodiment, an effective amount of Compound 2 Form B is administered in combination with an effective amount of savolitinib for the treatment of non-small cell lung cancer.

In one embodiment, an effective amount of Compound 2 Form B is administered in combination with an effective amount of savolitinib for the treatment of renal cell carcinoma.

In one embodiment, an effective amount of Compound 2 Form B is administered in combination with an effective amount of vistusertib for the treatment of advanced breast cancer.

In one embodiment, an effective amount of Compound 2 Form B is administered in combination with an effective amount of vistusertib for the treatment of advanced breast cancer.

In one embodiment, an effective amount of the isolated Compound 2 Form B described herein can be combined with a chemotherapeutic selected from, but are not limited to, Imatinib mesylate (Gleevac®), Dasatinib (Sprycel®), Nilotinib (Tasigna®), Bosutinib (Bosulif®), Trastuzumab (Herceptin®), Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Tagretin®), Alitretinoin (Panretin®), Tretinoin (Vesanoid®), Carfilizomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

In one embodiment, an effective amount of the isolated Compound 2 Form B described herein can be combined with a CD4/6 inhibitor including abemaciclib (Versenio), palbociclib (Ibrance), or trilaciclib.

In one embodiment, an effective amount of Compound 2 Form B is administered in combination with an effective amount of abemaciclib (Versenio) for the treatment of breast cancer.

In one embodiment, an effective amount of Compound 2 Form B is administered in combination with an effective amount of abemaciclib (Versenio) for the treatment of HR+ HER2− breast cancer.

In one embodiment, an effective amount of Compound 2 Form B is administered in combination with an effective amount of palbociclib (Ibrance) for the treatment of breast cancer.

In one embodiment, an effective amount of Compound 2 Form B is administered in combination with an effective amount of palbociclib (Ibrance) for the treatment of HR+ HER2− breast cancer.

In one embodiment, an effective amount of Compound 2 Form B is administered in combination with an effective amount of palbociclib (Ibrance) for the treatment of breast cancer.

In one embodiment, an effective amount of Compound 2 Form B is administered in combination with an effective amount of palbociclib (Ibrance) for the treatment of metastatic triple negative breast cancer.

In one embodiment, an effective amount of Compound 2 Form B is administered in combination with an effective amount of palbociclib (Ibrance) for the treatment of small cell lung cancer.

In one embodiment, an effective amount of Compound 2 Form B is administered in combination with an effective amount of cabozantinib S-malate (Cometriq™) for the treatment of thyroid cancer.

In one embodiment, an effective amount of Compound 2 Form B is administered in combination with an effective amount of cabozantinib S-maleate (Cometriq™) for the treatment of renal cell carcinoma.

In one embodiment, an effective amount of Compound 2 Form B is administered in combination with an effective amount of dasatinib (Sprycel) for the treatment of leukemia, including acute lymphoblastic leukemia or chronic myelogenous leukemia.

In one embodiment, an effective amount of Compound 2 Form B is administered in combination with an effective amount of dasatinib (Sprycel) for the treatment of prostate cancer.

In one embodiment, an effective amount of Compound 2 Form B is administered in combination with an effective amount of Erlotinib (Tarceva®) for the treatment of prostate cancer.

In one embodiment, an effective amount of Compound 2 Form B is administered in combination with an effective amount of Gefitinib (Iressa®) for the treatment of prostate cancer.

In one embodiment, an effective amount of Compound 2 Form B is administered in combination with an effective amount of imatinib mesylate (Gleevec) for the treatment of leukemia, including acute lymphoblastic leukemia, chronic eosinophilic leukemia, hypereosinophilic syndrome, or chronic myelogenous leukemia.

In one embodiment, an effective amount of Compound 2 Form B is administered in combination with an effective amount of trastuzumab (Herceptin) for the treatment of adenocarcinoma.

In one embodiment, an effective amount of Compound 2 Form B is administered in combination with an effective amount of trastuzumab (Herceptin) for the treatment of breast cancer, including HER2+ breast cancer.

In one embodiment, an effective amount of Compound 2 Form B is administered in combination with an effective amount of imatinib mesylate (Gleevec) for the treatment of tumors, including but not limited to dermatofibrosarcoma protuberans and gastrointestinal stromal tumors.

In one embodiment, an effective amount of Compound 2 Form B is administered in combination with an effective amount of imatinib mesylate (Gleevec) for the treatment of myelodysplastic/myeloproliferative neoplasms.

In one embodiment, an effective amount of Compound 2 Form B is administered in combination with an effective amount of imatinib mesylate (Gleevec) for the treatment of systemic mastocytosis.

In one embodiment, an effective amount of Compound 2 Form B is administered in combination with an effective amount of nilotinib (Tasigna) for the treatment of chronic myelogenous leukemia, including Philadelphia chromosome positive chronic myeloid leukemia (Ph+ CML).

In one embodiment, an effective amount of Compound 2 Form B is administered in combination with an effective amount of pazopanib hydrochloride (Votrient) for the treatment of renal cell carcinoma.

In one embodiment, an effective amount of Compound 2 Form B is administered in combination with an effective amount of pazopanib hydrochloride (Votrient) for the treatment of soft tissue sarcoma.

In one embodiment, an effective amount of Compound 2 Form B is administered in combination with an effective amount of regorafenib (Stivarga) for the treatment of colorectal cancer.

In one embodiment, an effective amount of Compound 2 Form B is administered in combination with an effective amount of regorafenib (Stivarga) for the treatment of gastrointestinal stromal tumor.

In one embodiment, an effective amount of Compound 2 Form B is administered in combination with an effective amount of regorafenib (Stivarga) for the treatment of hepatocellular carcinoma.

In one embodiment, an effective amount of Compound 2 Form B is administered in combination with an effective amount of sorafenib Tosylate (Nexavar) for the treatment of carcinoma, including hepatocellular carcinoma or renal cell carcinoma.

In one embodiment, an effective amount of Compound 2 Form B is administered in combination with an effective amount of sunitinib malate (Sutent) for the treatment of gastrointestinal stromal tumor.

In one embodiment, an effective amount of Compound 2 Form B is administered in combination with an effective amount of sunitinib malate (Sutent) for the treatment of pancreatic cancer.

In one embodiment, an effective amount of Compound 2 Form B is administered in combination with an effective amount of sunitinib malate (Sutent) for the treatment of renal cell carcinoma.

In one embodiment, an effective amount of Compound 2 Form B is administered in combination with an effective amount of vemurafenib (Zelboraf) for the treatment of Erdheim-Chester disease.

In one embodiment, an effective amount of Compound 2 Form B is administered in combination with an effective amount of vemurafenib (Zelboraf) for the treatment of melanoma.

In certain aspects, the additional therapeutic agent is an anti-inflammatory agent, a chemotherapeutic agent, a radiotherapeutic, additional therapeutic agents, or immunosuppressive agents.

Suitable chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™) Examples of additional suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), anti-mitotic agents, cis-dichlorodiamine platinum (II) (DDP) cisplatin), diamino dichloro platinum, anthracycline, an antibiotic, an antimetabolite, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCl, daunorucbicin citrate, denileukin diftitox, Dexrazoxane, Dibromomannitol, dihydroxy anthracin dione, Docetaxel, dolasetron mesylate, doxorubicin HCl, dronabinol, E. coli L-asparaginase, emetine, epoetin-α, Erwinia L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCl, glucocorticoids, goserelin acetate, gramicidin D, granisetron HCl, hydroxyurea, idarubicin HCl, ifosfamide, interferon α-2b, irinotecan HCl, letrozole, leucovorin calcium, leuprolide acetate, levamisole HCl, lidocaine, lomustine, maytansinoid, mechlorethamine HCl, medroxyprogesterone acetate, megestrol acetate, melphalan HCl, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCl, plimycin, polifeprosan 20 with carmustine implant, porfimer sodium, procaine, procarbazine HCl, propranolol, rituximab, sargramostim, streptozotocin, tamoxifen, taxol, teniposide, tenoposide, testolactone, tetracaine, thioepa chlorambucil, thioguanine, thiotepa, topotecan HCl, toremifene citrate, trastuzumab, tretinoin, valrubicin, vinblastine sulfate, vincristine sulfate, and vinorelbine tartrate.

In one embodiment, an effective amount of Compound 2 Form B is administered in combination with an effective amount of bosutinib (Bosulif®) for the treatment of chronic myelogenous leukemia (CML).

In one embodiment, an effective amount of Compound 2 Form B is administered in combination with an effective amount of ponatinib hydrochloride (Iclusig) for the treatment of leukemia, including acute lymphoblastic leukemia and chronic myelogenous leukemia.

Additional therapeutic agents that can be administered in combination with a compound disclosed herein can include bevacizumab, sutinib, sorafenib, 2-methoxyestradiol or 2ME2, finasunate, vatalanib, vandetanib, aflibercept, volociximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, celecoxib, bazedoxifene, AZD4547, rilotumumab, oxaliplatin (Eloxatin), PD0332991, ribociclib (LEE011), amebaciclib (LY2835219), HDM201, fulvestrant (Faslodex), exemestane (Aromasin), PIM447, ruxolitinib (INC424), BGJ398, necitumumab, pemetrexed (Alimta), and ramucirumab (IMC-1121B).

In one embodiment, an effective amount of Compound 2 Form B is administered in combination with an effective amount of everolimus (Afinitor) for the treatment of breast cancer.

In one embodiment, an effective amount of Compound 2 Form B is administered in combination with an effective amount of everolimus (Afinitor) for the treatment of HR+, HER2− breast cancer.

In one embodiment, an effective amount of Compound 2 Form B is administered in combination with an effective amount of everolimus (Afinitor) for the treatment of pancreatic cancer.

In one embodiment, an effective amount of Compound 2 Form B is administered in combination with an effective amount of everolimus (Afinitor) for the treatment of gastrointestinal cancer.

In one embodiment, an effective amount of Compound 2 Form B is administered in combination with an effective amount of everolimus (Afinitor) for the treatment of lung cancer.

In one embodiment, an effective amount of Compound 2 Form B is administered in combination with an effective amount of everolimus (Afinitor) for the treatment of renal cell carcinoma.

In one embodiment, an effective amount of Compound 2 Form B is administered in combination with an effective amount of everolimus (Afinitor) for the treatment of astrocytoma, including subependymal giant cell astrocytoma.

In one embodiment, an effective amount of Compound 2 Form B is administered in combination with an effective amount of fulvestrant (Faslodex) for the treatment of breast cancer.

In one embodiment, an effective amount of Compound 2 Form B is administered in combination with an effective amount of fulvestrant (Faslodex) for the treatment of HR+, HER2− breast cancer.

In one embodiment, an effective amount of Compound 2 Form B is administered in combination with an effective amount of ramucirumab for the treatment of adenocarcinoma.

In one embodiment, an effective amount of Compound 2 Form B is administered in combination with an effective amount of ramucirumab for the treatment of non-small cell lung cancer.

In one embodiment, an effective amount of Compound 2 Form B is administered in combination with an effective amount of ramucirumab for the treatment of colorectal cancer.

In one embodiment, an effective amount of Compound 2 Form B is administered in combination with an effective amount of ribociclib (Kisqali) for the treatment of breast cancer.

In one embodiment, an effective amount of Compound 2 Form B is administered in combination with an effective amount of ribociclib (Kisqali) for the treatment of HR+ and HER2− breast cancer.

In one aspect of the present invention, a compound described herein can be combined with at least one IDH1 or IDH2 inhibitor. In one embodiment, an effective amount of Compound 2 Form B is administered in combination with an effective amount of enasidenib mesylate (Idhifa) for the treatment of acute myeloid leukemia.

In one aspect of the present invention, a compound described herein can be combined with at least one fibroblast growth factor receptor (FGFR) tyrosine kinase inhibitor. In one embodiment, an effective amount of Compound 2 Form B is administered in combination with an effective amount of erdafitinib for the treatment of urothelial cancer, including metastatic urothelial cancer.

In one aspect of the present invention, a compound described herein can be combined with at least one ERK inhibitor.

In one embodiment, an effective amount of Compound 2 Form B is administered in combination with an effective amount of SCH772984 for the treatment of melanoma, including BRAF-mutant melanoma or NRAS-mutant melanoma.

In one embodiment, an effective amount of Compound 2 Form B is administered in combination with an effective amount of ulixertinib for the treatment of melanoma, including uveal melanoma.

In one embodiment, an effective amount of Compound 2 Form B is administered in combination with an effective amount of ulixertinib for the treatment of pancreatic cancer.

In one aspect of the present invention, a compound described herein can be combined with at least one immunosuppressive agent. The immunosuppressive agent is preferably selected from the group consisting of a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g., ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

In certain embodiments, a compound described herein is administered to the subject prior to treatment with another chemotherapeutic agent, during treatment with another chemotherapeutic agent, after administration of another chemotherapeutic agent, or a combination thereof.

In some embodiments, an effective amount of the isolated Compound 2 Form B can be administered to the subject such that the other chemotherapeutic agent can be administered either at higher doses (increased chemotherapeutic dose intensity) or more frequently (increased chemotherapeutic dose density). Dose-dense chemotherapy is a chemotherapy treatment plan in which drugs are given with less time between treatments than in a standard chemotherapy treatment plan. Chemotherapy dose intensity represents unit dose of chemotherapy administered per unit time. Dose intensity can be increased or decreased through altering dose administered, time interval of administration, or both.

In one embodiment of the invention, the compounds described herein can be administered in a concerted regimen with another agent such as a non-DNA-damaging, targeted anti-neoplastic agent or a hematopoietic growth factor agent. It has been recently been reported that the untimely administration of hematopoietic growth factors can have serious side effects. For example, the use of the EPO family of growth factors has been associated with arterial hypertension, cerebral convulsions, hypertensive encephalopathy, thromboembolism, iron deficiency, influenza like syndromes and venous thrombosis. The G-CSF family of growth factors has been associated with spleen enlargement and rupture, respiratory distress syndrome, allergic reactions and sickle cell complications. As such, in one embodiment, the use of the compounds or methods described herein is combined with the use of hematopoietic growth factors including, but not limited to, granulocyte colony stimulating factor (G-CSF, for example, sold as Neupogen (filgrastin), Neulasta (peg-filgrastin), or lenograstin), granulocyte-macrophage colony stimulating factor (GM-CSF, for example sold as molgramostim and sargramostim (Leukine)), M-CSF (macrophage colony stimulating factor), thrombopoietin (megakaryocyte growth development factor (MGDF), for example sold as Romiplostim and Eltrombopag) interleukin (IL)-12, interleukin-3, interleukin-11 (adipogenesis inhibiting factor or oprelvekin), SCF (stem cell factor, steel factor, kit-ligand, or KL) and erythropoietin (EPO), and their derivatives (sold as for example epoetin-α as Darbopoetin, Epocept, Nanokine, Epofit, Epogin, Eprex and Procrit; epoetin-β sold as for example NeoRecormon, Recormon and Micera), epoetin-delta (sold as for example Dynepo), epoetin-omega (sold as for example Epomax), epoetin zeta (sold as for example Silapo and Reacrit) as well as for example Epocept, EPOTrust, Erypro Safe, Repoeitin, Vintor, Epofit, Erykine, Wepox, Espogen, Relipoeitin, Shanpoietin, Zyrop and EPIAO). In one embodiment, an effective amount of the isolated Compound 2 Form B is administered prior to administration of the hematopoietic growth factor. In one embodiment, the hematopoietic growth factor administration is timed so that the compound's effect on HSPCs has dissipated. In one embodiment, the growth factor is administered at least 20 hours after the administration of a compound described herein.

If desired, multiple doses of a compound described herein can be administered to the subject. Alternatively, the subject can be given a single dose of a compound described herein. In one aspect of the invention, a compound disclosed herein can be beneficially administered in combination with any therapeutic regimen entailing radiotherapy, chemotherapy, or other therapeutic agents. In additional embodiments the compounds disclosed herein can be beneficially administered in combination with therapeutic agents targeting autoimmune disorders.

In an alternative embodiment Compound 2 Form A, C, D, E, G, or H, is administered in a combination described above instead of Compound 2 Form B to treat a host, typically a human, with a selected cancer, tumor, hyperproliferative condition or an inflammatory or immune disorder.

EXAMPLES

Example 1

Conversion of Compound 1 to its HCl Counterpart, Compound 2

A representative synthesis of Compound 2 is provided in Scheme 1.

Scheme 1

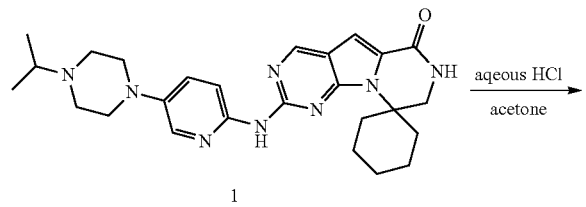

aqeous HCl
acetone

1

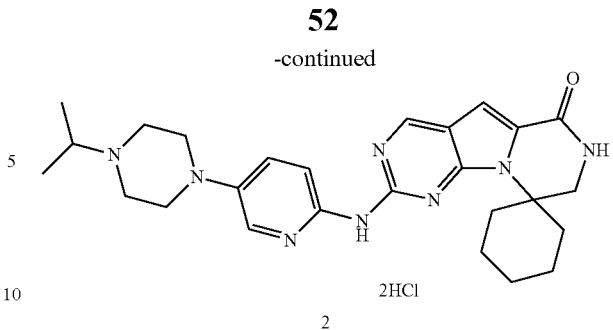

2HCl

2

Compound 1 (0.9 kg. 1.9 moles, 1 eq) was charged to a 22 L flask and dissolved in aqueous, 2 M hydrochloric acid solution (3.78 L). The solution was heated to 50±5° C., stirred for 30 minutes, and the resulting mixture filtered over Celite (alternatively the solution may be filtered through a 0.45 micron in-line filter) to afford Compound 2. The flask was rinsed with 0.1 M hydrochloric acid solution to collect any additional Compound 2. Compound 2 was then heated to 50±5° C. while acetone (6.44 L) was slowly added. The solution was stirred at 50±5° C. for 30 minutes, the temperature was decreased to 20±5° C., and stirring continued for 2 hours. The solids were collected by filtration, washed with acetone, and dried to afford 820.90 g of Compound 2 (82.1% yield). In one embodiment instead of acetone, ethanol is used.

Example 2

Morphic Forms of Compound 2

Figure 1:
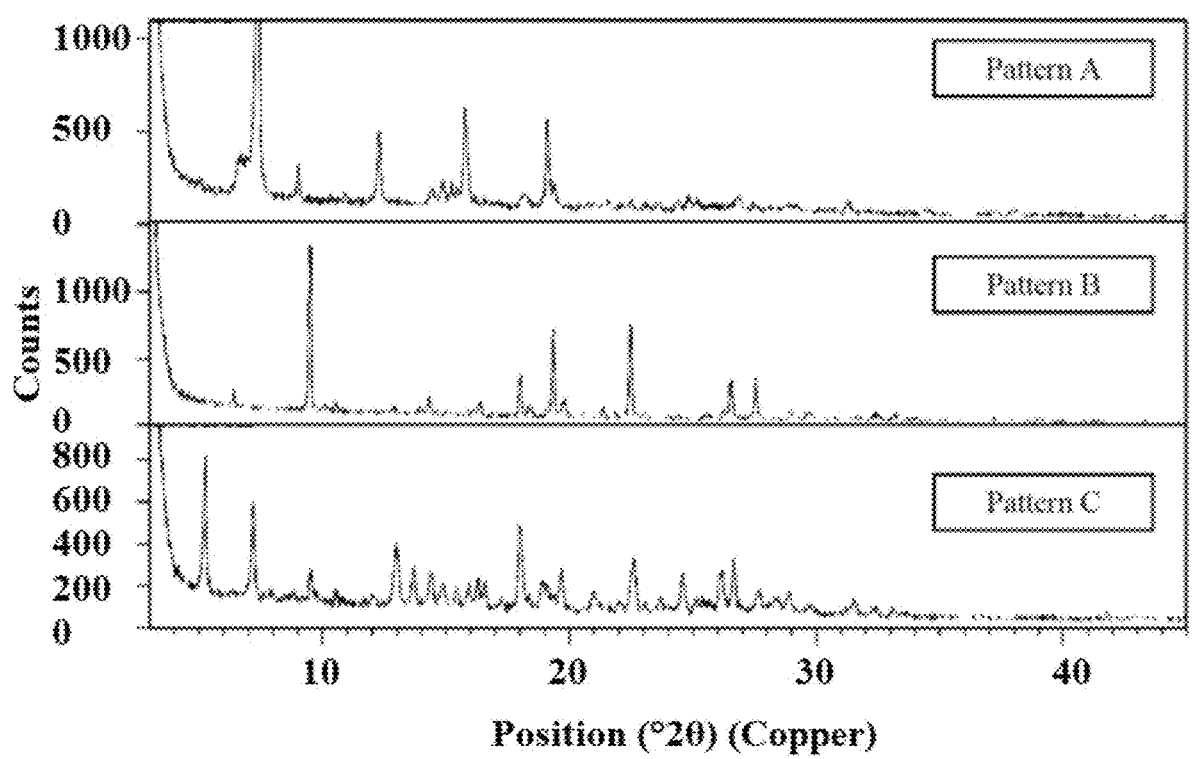
FIG. 1 is a comparison of XRPD patterns of Form A, Form B, and Form C. These three forms were obtained from crystallization and slurry experiments as described in Example 2 and shown in Tables 1-4. The x-axis is 2Theta measured in degrees and the y-axis is intensity measured in counts.
Figure 2:
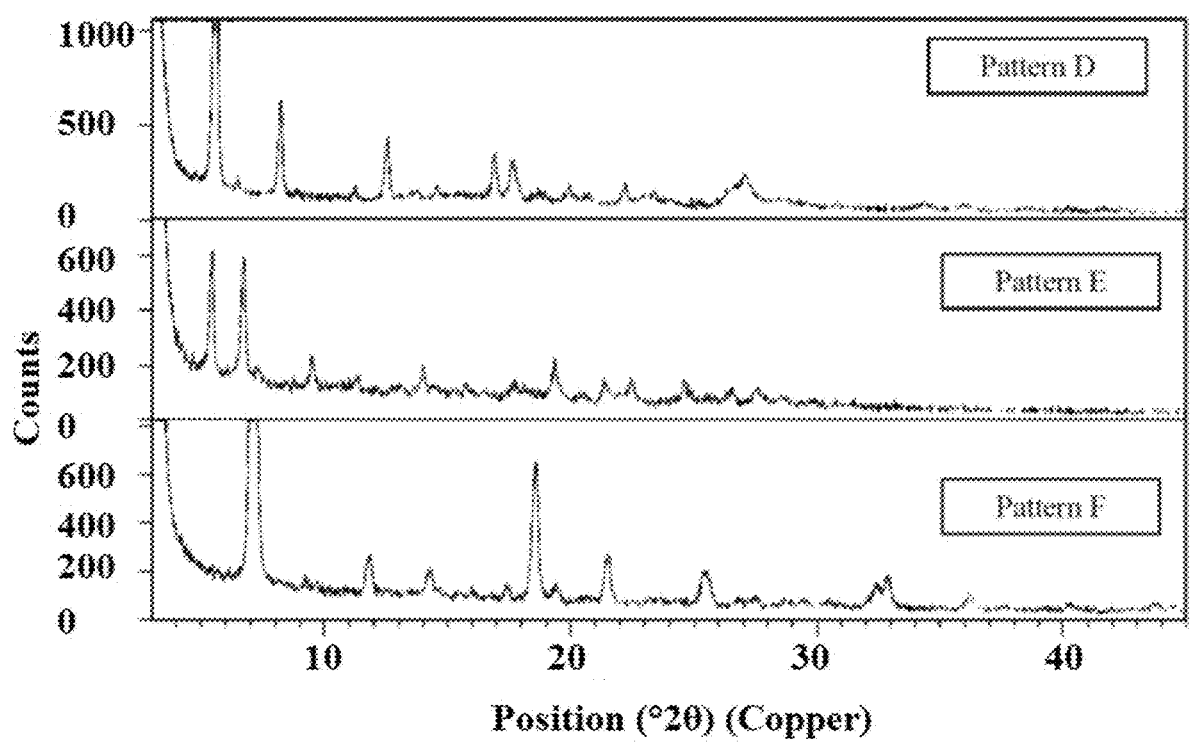
FIG. 2 is a comparison of XRPD patterns of Form D, Form E, and Form F. These three forms were obtained from crystallization and slurry experiments as described in Example 2 and shown in Tables 1-4. The x-axis is 2Theta measured in degrees and the y-axis is intensity measured in counts.
Figure 3:
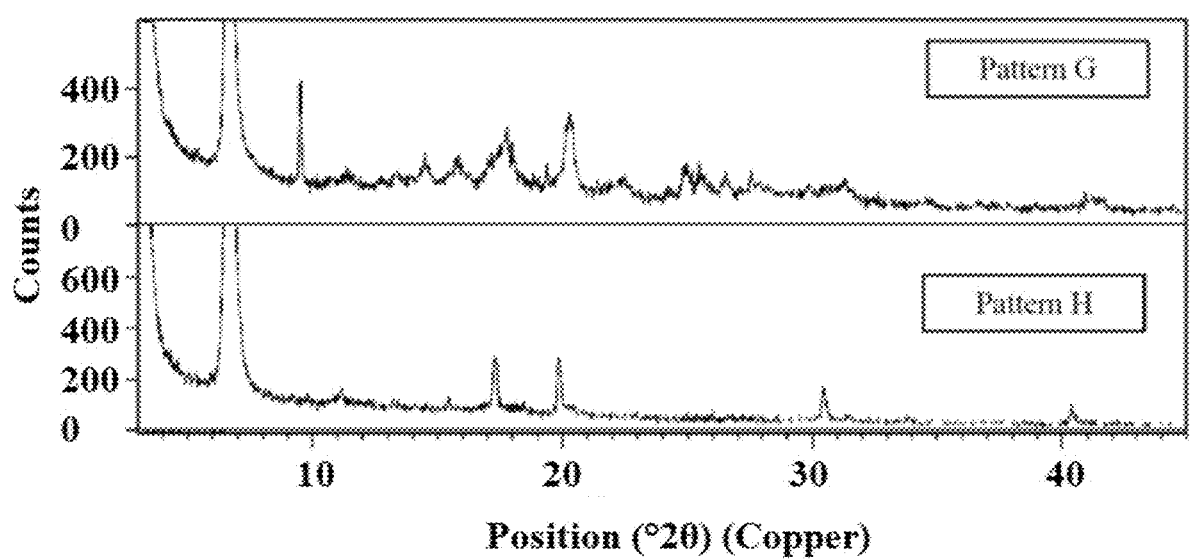
FIG. 3 is a comparison of XRPD patterns of Form G and Form H. These two forms were obtained from crystallization and slurry experiments as described in Example 2 and shown in Tables 1-4. Form G is an anhydrate and Form H is an n-PrOH solvate. The x-axis is 2Theta measured in degrees and the y-axis is intensity measured in counts.

Eleven unique XRPD patterns (Form A-Form K) of Compound 2 were obtained from crystallization and slurry experiments using various solvents. The conditions and XRPD results for these crystallization experiments are given in Tables 1-4. Single solvent crystallizations (Table 1) resulted in weak crystalline forms or Form A. Binary solvent crystallizations using water (Table 2) and MeOH (Table 3) as the primary solvent resulted in weak crystalline forms and Form A, Form B, Form F, Form G, and Form H. Solids recovered from slurry experiments after one and seven days of equilibration (Table 4) were analyzed by XRPD to determine the crystalline form, and after seven days, Form A, Form B, Form C, Form D, and Form E were observed. FIG. 1 shows the XRPD patterns of Form A, Form B, and Form C. FIG. 2 shows the XRPD patterns of Form D, Form E, and Form F. FIG. 3 shows the XRPD patterns of Form G and Form H.

TABLE 1

Single Solvent Crystallization Conditions and Results

| Solvent | Volume (mL) | Temp. (° C.) | Cooling | Precipitation/Isolation | XRPD |
| --- | --- | --- | --- | --- | --- |
| Water | 2.0 | 60 | Slow (20° C./hr) | Turbid/Evap. | Weak crystalline |
| MeOH | 0.5 | 60 | Slow (20° C./hr) | ppt/filter | A |
| EtOH | 4.0 | 60 | Slow (20° C./hr) | ppt/filter | A |
| 1-PrOH | 4.0 | 60 | Slow (20° C./hr) | ppt/filter | Weak crystalline |
| 1-BuOH | 4.0 | 60 | Slow (20° C./hr) | ppt/filter | A |
| Water | 2.0 | 60 | Fast Cooling (4° C.) | Turbid/Evap. | Weak crystalline |

TABLE 1-continued

Single Solvent Crystallization Conditions and Results

| Solvent | Volume (mL) | Temp. (° C.) | Cooling | Precipitation/ Isolation | XRPD |
|---|---|---|---|---|---|
| MeOH | 0.5 | 60 | Fast Cooling (4° C.) | ppt/filter | Weak crystalline |
| EtOH | 4.0 | 60 | Fast Cooling (4° C.) | ppt/filter | A |
| 1-PrOH | 4.0 | 60 | Fast Cooling (4° C.) | ppt/filter | Weak crystalline |
| 1-BuOH | 4.0 | 60 | Fast Cooling (4° C.) | ppt/filter | Weak crystalline |

TABLE 2

Binary Solvent Crystallizations using water as Primary Solvent

| Primary Solvent/Vol. (mL) | Temp. (° C.) | Cooling | Anti Solvent/Vol. (mL) | Precipitation/ Isolation | XRPD |
|---|---|---|---|---|---|
| Water/0.5 | 60.0 | Fast Cooling (4° C.) | EtOH/5.0 | Clear/Evap. | Weak crystalline |
| Water/0.5 | 60.0 | Fast Cooling (4° C.) | n-PrOH/5.0 | Clear/Evap. | Weak crystalline |
| Water/0.5 | 60.0 | Fast Cooling (4° C.) | IPA/5.0 | ppt/filter | G |
| Water/0.5 | 60.0 | Fast Cooling (4° C.) | MeCN/5.0 | ppt/filter | Weak crystalline |
| Water/0.5 | 60.0 | Fast Cooling (4° C.) | THF/3.0 | ppt/filter | Weak crystalline |
| Water/0.5 | 60.0 | Fast Cooling (4° C.) | Acetone/3.5 | ppt/filter | G |
| Water/0.5 | 60.0 | Slow Cooling (20° C./hr) | EtOH/5.0 | Clear/Evap. | Weak crystalline |
| Water/0.5 | 60.0 | Slow Cooling (20° C./hr) | n-PrOH/5.0 | Clear/Evap. | H |
| Water/0.5 | 60.0 | Slow Cooling (20° C./hr) | IPA/5.0 | ppt/filter | B |
| Water/0.5 | 60.0 | Slow Cooling (20° C./hr) | MeCN/5.0 | ppt/filter | A |
| Water/0.5 | 60.0 | Slow Cooling (20° C./hr) | THF/3.0 | ppt/filter | G |
| Water/0.5 | 60.0 | Slow Cooling (20° C./hr) | Acetone/3.5 | ppt/filter | B |

TABLE 3

Binary Solvent Crystallizations using MeOH as Primary Solvent

| Primary Solvent/Vol. (mL) | Temp. (° C.) | Cooling | Anti Solvent/Vol. (mL) | Precipitation/ Isolation | XRPD |
|---|---|---|---|---|---|
| MeOH/0.5 | 60.0 | Fast Cooling (4° C.) | EtOH/5.0 | ppt/filter | A |
| MeOH/0.5 | 60.0 | Fast Cooling (4° C.) | n-PrOH/5.0 | ppt/filter | Weak crystalline |
| MeOH/0.5 | 60.0 | Fast Cooling (4° C.) | IPA/2.5 | ppt/filter | F |
| MeOH/0.5 | 60.0 | Fast Cooling (4° C.) | n-BuOH/5.0 | ppt/filter | Weak crystalline |
| MeOH/0.5 | 60.0 | Fast Cooling (4° C.) | MeCN/2.5 | ppt/filter | A |
| MeOH/0.5 | 60.0 | Fast Cooling (4° C.) | THF/0.5 | ppt/filter | A |
| MeOH/0.5 | 60.0 | Fast Cooling (4° C.) | 2-MeTHF/0.1 | ppt/filter | A |
| MeOH/0.5 | 60.0 | Fast Cooling (4° C.) | EtOAc/0.2 | ppt/filter | Weak crystalline |
| MeOH/0.5 | 60.0 | Fast Cooling (4° C.) | IPAc/0.1 | ppt/filter | A |
| MeOH/0.5 | 60.0 | Fast Cooling (4° C.) | Acetone/0.5 | ppt/filter | A |
| MeOH/0.5 | 60.0 | Slow Cooling (20° C./hr) | MEK/0.2 | ppt/filter | A |
| MeOH/0.5 | 60.0 | Slow Cooling (20° C./hr) | MIBK/0.1 | ppt/filter | Weak crystalline |
| MeOH/0.5 | 60.0 | Slow Cooling (20° C./hr) | DCM/5.0 | Clear/Evap. | A |
| MeOH/0.5 | 60.0 | Slow Cooling (20° C./hr) | Toluene/1.5 | ppt/filter | A |
| MeOH/0.5 | 60.0 | Slow Cooling (20° C./hr) | MTBE/0.1 | ppt/filter | A |
| MeOH/0.5 | 60.0 | Slow Cooling (20° C./hr) | EtOH/5.0 | ppt/filter | Weak crystalline |
| MeOH/0.5 | 60.0 | Slow Cooling (20° C./hr) | n-PrOH/5.0 | ppt/filter | Weak crystalline |
| MeOH/0.5 | 60.0 | Slow Cooling (20° C./hr) | IPA/2.5 | ppt/filter | A |
| MeOH/0.5 | 60.0 | Slow Cooling (20° C./hr) | n-BuOH/5.0 | ppt/filter | Weak crystalline |
| MeOH/0.5 | 60.0 | Slow Cooling (20° C./hr) | MeCN/2.5 | ppt/filter | Weak crystalline |

TABLE 3-continued

Binary Solvent Crystallizations using MeOH as Primary Solvent

| Primary Solvent/Vol. (mL) | Temp. (° C.) | Solvent/Vol. Cooling | Anti Precipitation/ (mL) | Isolation | XRPD |
|---|---|---|---|---|---|
| MeOH/0.5 | 60.0 | Slow Cooling (20° C./hr) | THF/0.5 | ppt/filter | Weak crystalline |
| MeOH/0.5 | 60.0 | Slow Cooling (20° C./hr) | 2-MeTHF/0.1 | ppt/filter | A |
| MeOH/0.5 | 60.0 | Slow Cooling (20° C./hr) | EtOAc/0.2 | ppt/filter | A |
| MeOH/0.5 | 60.0 | Slow Cooling (20° C./hr) | IPAc/0.1 | ppt/filter | A |
| MeOH/0.5 | 60.0 | Slow Cooling (20° C./hr) | Acetone/0.5 | ppt/filter | Weak crystalline |
| MeOH/0.5 | 60.0 | Slow Cooling (20° C./hr) | MEK/0.2 | ppt/filter | A |
| MeOH/0.5 | 60.0 | Slow Cooling (20° C./hr) | MIBK/0.1 | ppt/filter | A |
| MeOH/0.5 | 60.0 | Slow Cooling (20° C./hr) | DCM/5.0 | Clear/Evap. | A |
| MeOH/0.5 | 60.0 | Slow Cooling (20° C./hr) | Toluene/1.5 | ppt/filter | Weak crystalline |
| MeOH/0.5 | 60.0 | Slow Cooling (20° C./hr) | MTBE/0.1 | ppt/filter | A |

TABLE 4

Slurry Experiments of Compound 2

| Solvent | Solvent Vol. (mL) | Method | Time point (1 day) XRPD | Time point (7 days) XRPD |
|---|---|---|---|---|
| IPA | 1.0 | Stirring at RT | A | F |
| MeCN | 1.0 | Stirring at RT | D | D |
| THF | 1.0 | Stirring at RT | Weak Crystalline | E |
| 2-MeTHF | 1.0 | Stirring at RT | Weak Crystalline | B |
| EtOAc | 1.0 | Stirring at RT | A | C |
| IPAc | 1.0 | Stirring at RT | A with extra peak | B |
| Acetone | 1.0 | Stirring at RT | E | B |
| MEK | 1.0 | Stirring at RT | Weak Crystalline | B |
| MIBK | 1.0 | Stirring at RT | E | B |
| Toluene | 1.0 | Stirring at RT | E | B |
| MTBE | 1.0 | Stirring at RT | A | B |
| n-Heptane | 1.0 | Stirring at RT | A | A |
| c-Hexane | 1.0 | Stirring at RT | A | A |

Example 2

Characterization of Compound 2 Morphic Forms

A summary of characterization data of all isolated forms of Compound 2 is given in Table 5. Forms A, B, and D were evaluated as solid state forms.

TABLE 5

Characterization Data of Morphic Forms of Compound 2

| XRPD Pattern | Possible Form | DSC (° C.) | TGA (wt loss) | 1H NMR (DMSO-$d_6$) | % Cl (API:HCl) |
|---|---|---|---|---|---|
| A | Hydrate | Endotherms at 110.3, 275.6, 344.8 | Onset 5.7 wt % loss at 66.0° C., Onset 5.4 wt % loss at 215.5° C., Onset 6.2 wt % loss at 314.0° C. | Contains water | 11.1% (1:1.67)* |
| B | Hydrate | Endotherms at 105.2, 220.8, 265.6, 350.6 | Onset 5.1 wt % loss at 60.9° C., Onset 7.2 wt % loss at 198.3° C., Onset 7.8 wt % loss at 319.6° C. | Contains water and residual solvent | 11.90% (1:1.81) |
| C | EtOAc solvate | Endotherms at 95.1, 235.6, 257.8, 344.6 | Onset 1.6 wt % loss at 72.9° C., Onset 5.1 wt % loss at 192.0° C., Onset 0.9 wt % loss at 223.4° C., Onset 6.9 wt % loss at 306.7° C. | Contains water and EtOAc as residual solvent | Not determined |
| D | Hydrate | Endotherms at 108.3, 266.1, 347.0 | Onset 6.0 wt % loss at 68.8° C., Onset 6.0 wt % loss at 207.6° C., Onset 3.6 wt % loss at 304.9° C., Onset 6.6 wt % loss at 324.7° C. | Contains water and residual solvent | 12.23% (1:1.87) |

TABLE 5-continued

Characterization Data of Morphic Forms of Compound 2

| XRPD Pattern | Possible Form | DSC (° C.) | TGA (wt loss) | 1H NMR (DMSO-$d_6$) | % Cl (API:HCl) |
|---|---|---|---|---|---|
| E | Acetone solvate | Endotherms at 70.3, 275.2, 345.9 Exotherm at 220.0 | Onset 1.0 wt % loss at 41.9° C., Onset 1.1 wt % loss at 61.5° C., Onset 1.0 wt % loss at 93.2° C., Onset 5.0 wt % loss at residual 211.6° C., Onset 5.6 wt % loss at 308.5° C. | Contains water and acetone as solvent | Not determined |
| F | Unstable hydrate | Endotherms at 73.2, 214.5, 303.4, 329.7 Exotherm at 277.8 | Onset 8.0 wt % loss at 43.7° C., Onset 2.1 wt % loss at 190.7° C., Onset 7.6 wt % loss at 308.8° C. | Contains water | Not determined |
| G | Anhydrate | Endotherms at 81.8, 120.8, 268.2, 347.9 | Onset 4.5 wt % loss at 47.2° C., Onset 3.1 wt % loss at 86.6° C., Onset 4.5 wt % loss at 213.3° C., Onset 4.6 wt % loss at 311.2° C. | Contains water | Not determined |
| H | n-PrOH solvate | Endotherms at 110.5, 225.6, 274.5, 346.3 | Onset 1.9 wt % loss at 45.6° C., Onset 4.6 wt % loss at 71.9° C., Onset 1.8 wt % loss at 187.9° C., Onset 2.2 wt % loss at 222.1° C., Onset 3.0 wt % loss at 303.0° C., Onset 2.2 wt % loss at 325.2° C. | Contains water and n-PrOH as residual solvent | Not determined |

In one embodiment Form A is characterized by at least one XRPD peaks at 7.4±0.2°, 9.0±0.2°, or 12.3±0.2° 2theta. In one embodiment Form B is characterized by at least one XRPD peaks at 6.4±0.2°, or 9.5±0.2° 2theta. In one embodiment Form C is characterized by at least one XRPD peaks at 5.3±0.2°, or 7.2±0.2° 2theta. In one embodiment Form D is characterized by at least one XRPD peaks at 5.6±0.2°, or 8.2±0.2° 2theta. In one embodiment Form E is characterized by at least one XRPD peak at 5.5±0.2°, or 6.7±0.2° 2theta. In one embodiment Form E is characterized by at least one XRPD peak at 5.5±0.2°, or 6.7±0.2° 2theta. In one embodiment Form F is characterized by a XRPD peak at 7.2±0.2° 2theta. In one embodiment Form G is characterized by a XRPD peak at 6.7±0.2° 2theta. In one embodiment Form H is characterized by a XRPD peak at 6.6±0.2° 2theta.

Example 3

Dynamic Vapor Sorption Experiments of Form A, Form B, and Form D

Dynamic vapor sorption experiments were performed on Form A, Form B, and Form D. Table 6 provides the results of the DVS experiment.

TABLE 6

Moisture Sorption Data of Forms A, B, and D

| XRPD (pre DVS) | % wt change at 60% RH | % wt change at 90% RH | XRPD (post DVS) |
|---|---|---|---|
| Form A | 14.9 | 15.8 | Form K |
| Form B | 5.8 | 5.9 | Form B |
| Form D | 4.4 | 17.0 | Form K |

Figure 4A:
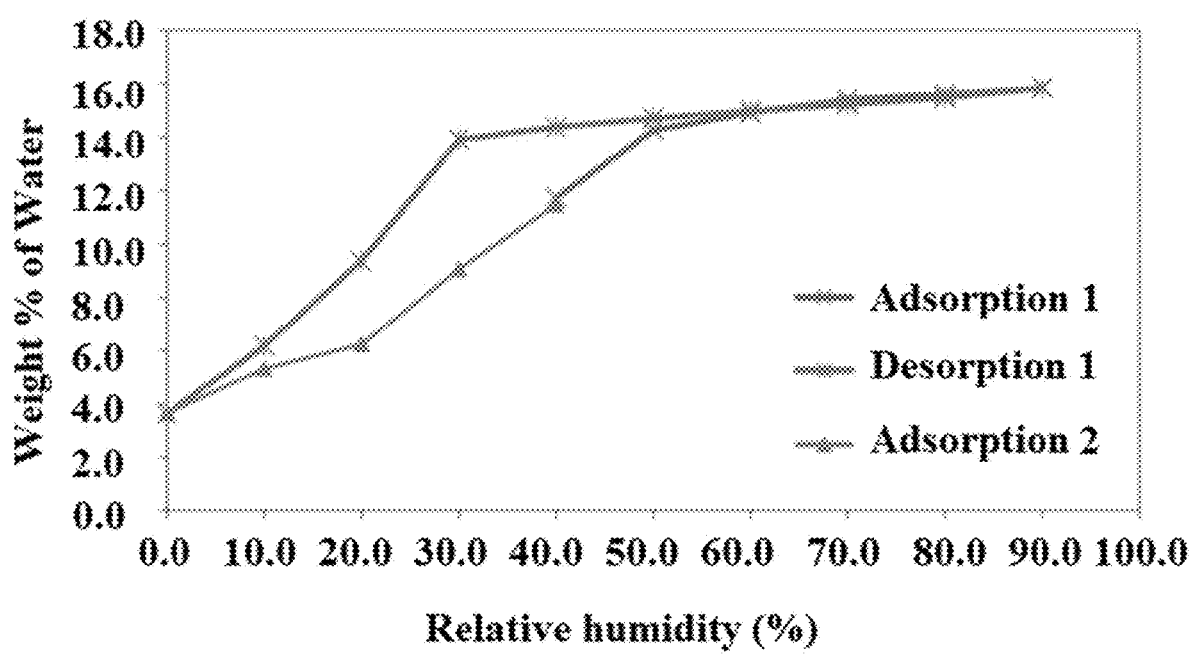
FIG. 4A is a dynamic vapor sorption analysis showing the results from a moisture sorption experiment of Form A (Example 3). The material was found to be unstable and the XRPD analysis of dried sample at the conclusion of the experiment revealed a new Form, Form K. Form A adsorbed 14.9 wt % at 60% RH (relative humidity) and 15.8 wt % at 90% RH. The x-axis is relative humidity measured as a percent and the y-axis is weight of water of the material measured as a percent.
Figure 4B:
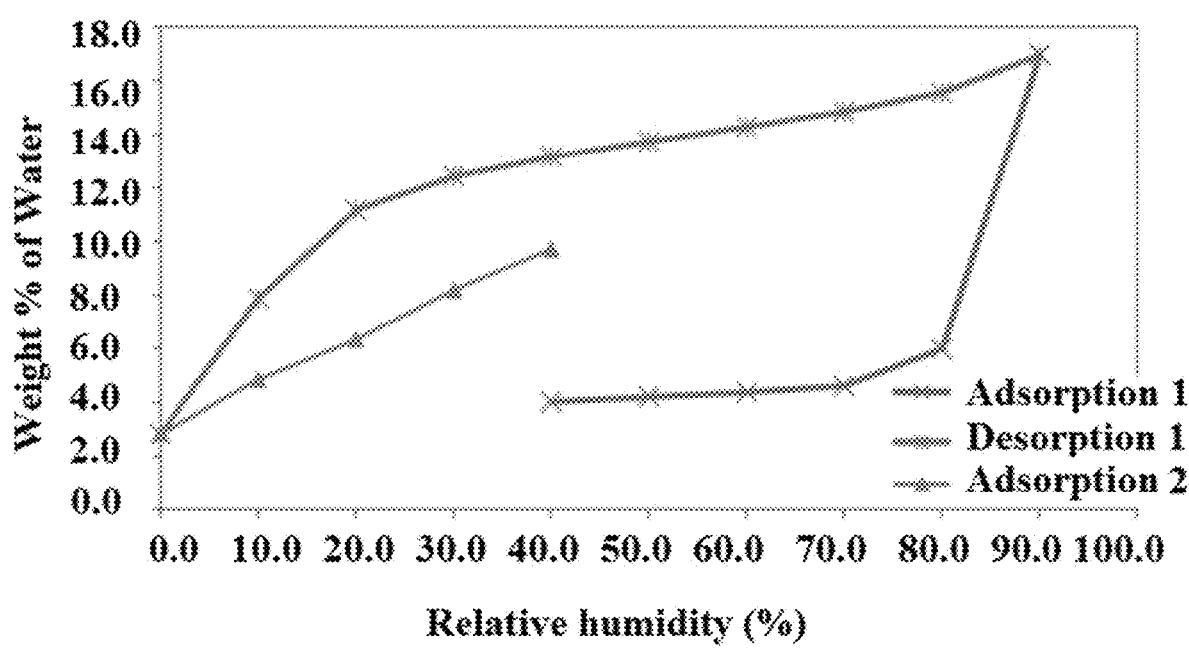
FIG. 4B is a dynamic vapor sorption analysis showing the results from a moisture sorption experiment of Form D (Example 3). The material was found to be unstable and the XRPD analysis of dried sample at the conclusion of the experiment revealed a new Form, Form K. Form D adsorbed 4.4 wt % at 60% RH (relative humidity) and 4.4 wt % at 90% RH. The x-axis is relative humidity measured as a percent and the y-axis is weight of water of the material measured as a percent.

Form A was found to be unstable in the moisture sorption experiment. The material adsorbed 14.9 wt % moisture at 60% RH and 15.8 wt % at 90% RH. After the moisture sorption experiment, the sample was dried at 60° C. and 0% RH and the result of the XRPD analysis of dried sample showed a new Form (Form K). The DVS analysis of Form A is shown in FIG. 4A. Form D was also found to be unstable in the moisture sorption experiment. The material adsorbed 4.4 wt % moisture at 60% RH and 17.0 wt % at 90% RH. After the moisture sorption experiment, the sample was dried at 60° C. and 0% RH and the result of the XRPD analysis of dried sample showed Form K. The DVS analysis of Form D is shown in FIG. 4B.

Figure 4C:
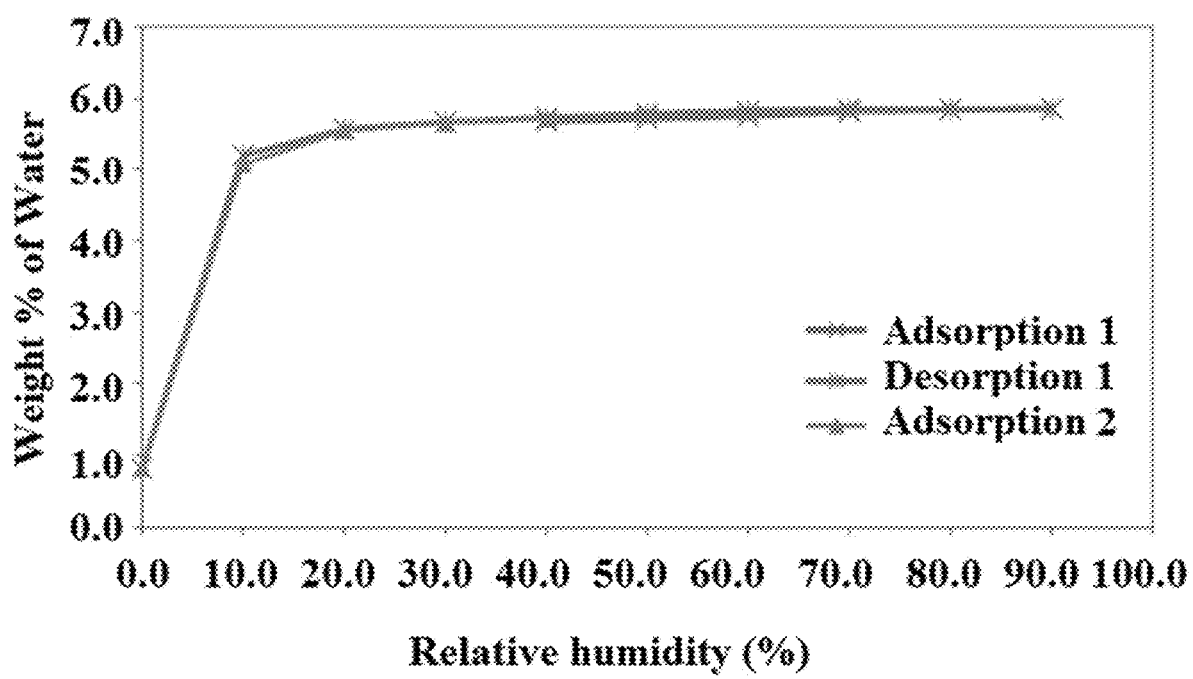
FIG. 4C is a dynamic vapor sorption analysis showing the results from a moisture sorption experiment of Form B (Example 3). The material is stable and the XRPD analysis of a dried sample at the conclusion of the experiment confirmed Form B. Form B adsorbed 5.8 wt % at 60% RH (relative humidity), and 5.9 wt % at 90% RH. The x-axis is relative humidity measured as a percent and the y-axis is weight of water of the material measured as a percent.

Unlike Form A and Form D, Form B was stable in the moisture sorption experiment. The material adsorbed 5.8 wt % moisture at 60% RH and 5.9 wt % at 90% RH. After drying at 60° C. and 0% RH for two hours, the XRPD pattern remained unchanged as Form B. The DVS analysis of Form B is shown in FIG. 4C.

Figure 5A:
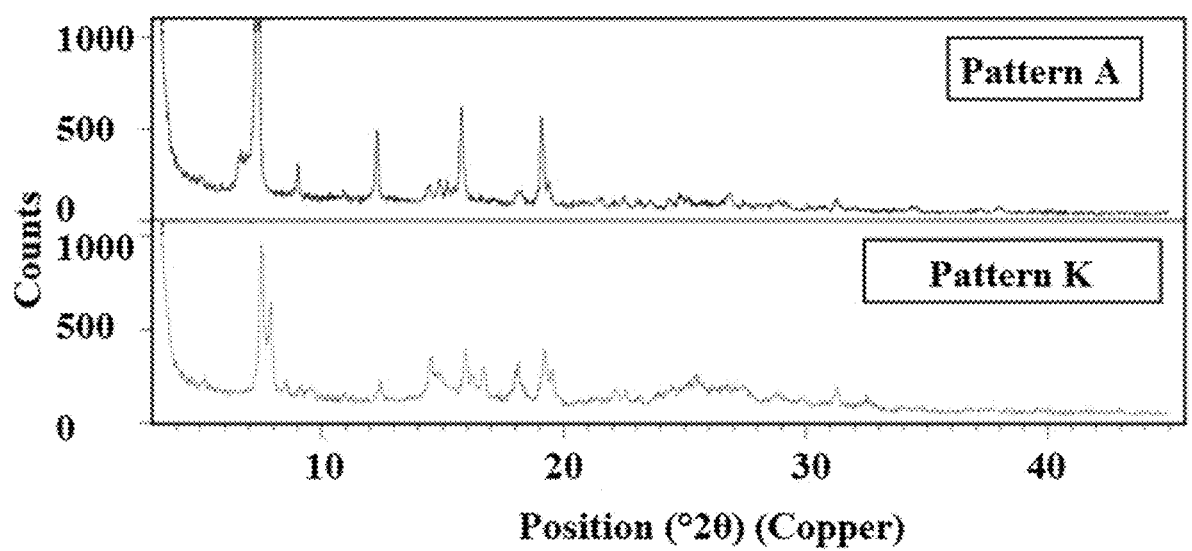
FIG. 5A is a comparison of XRPD patterns of Form A before the moisture sorption experiment (top) and after the moisture sorption experiment (bottom). After the moisture sorption experiment, XRPD analysis revealed that Form A is not stable and had converted to a new Form, Form K (Example 3). The x-axis is 2Theta measured in degrees and the y-axis is intensity measured in counts.
Figure 5B:
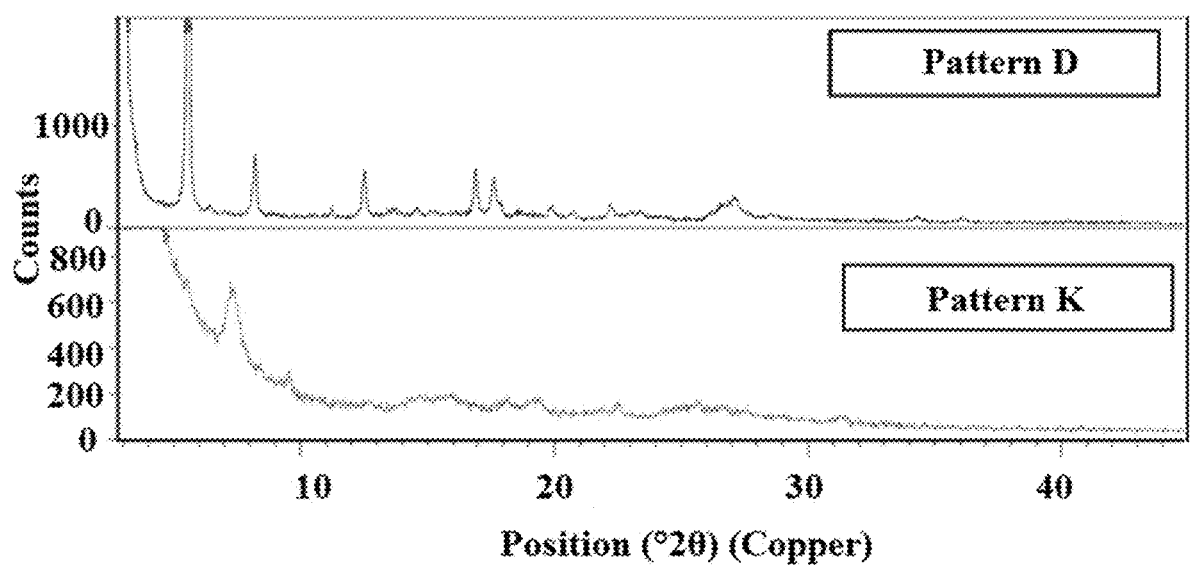
FIG. 5B is a comparison of XRPD patterns of Form D before the moisture sorption experiment (top) and after the moisture sorption experiment (bottom). After the moisture sorption experiment, XRPD analysis revealed that Form D is not stable and had converted to a new Form, Form K (Example 3). The x-axis is 2Theta measured in degrees and the y-axis is intensity measured in counts.

FIG. 5A is a comparison of the XRPD pattern of Form A before DVS analysis and the new pattern (Form K) that resulted from DVS. FIG. 5B is a comparison of the XRPD pattern of Form D before DVS and the pattern (Form K) that resulted after DVS.

Example 4

Stability Study of Forms A, B, and D Under Thermal Stress

Figure 6:
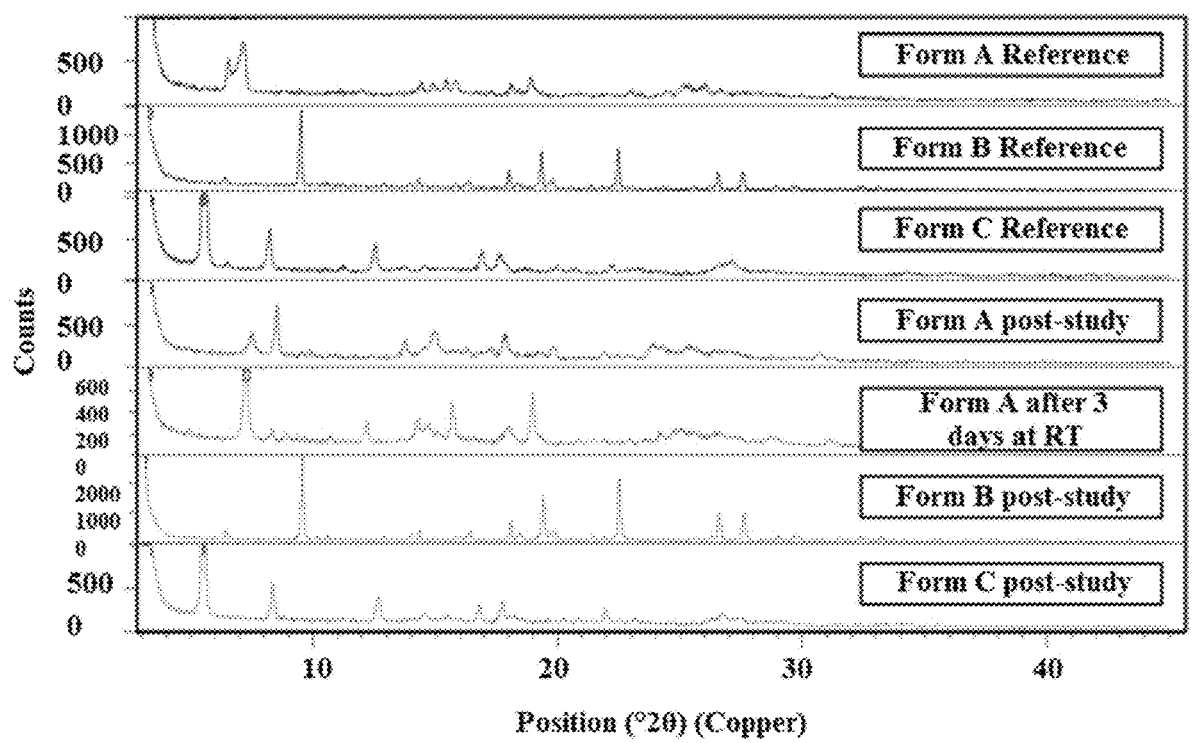
FIG. 6 is a comparison of the XRPD patterns of Form A, Form B, and Form C after the stability study (Example 4) to reference Form A, Form B and Form C. The top thee patterns are reference forms of Form A, Form B, and Form C. After the seven-day stability study, Form A converted to a new Form (Form A post-study), but after equilibrium at room temperature for 3 days, the new form changed back to Form A (Form A after 3 days). Form B and Form C remained unchanged during the stability study. The x-axis is 2Theta measured in degrees and the y-axis is intensity measured in counts.

Forms A, B, and D were stored in an oven maintained at 60° C. for 7 days. No change in the XRPD pattern was observed for Form B or Form D. A new pattern was found for Form A at the conclusion of the stability study, however after equilibrium for three days at room temperature, the XRPD of the new Form revealed that it had converted back to Form A. FIG. 6 compares the XRPD patterns of Form A, Form B, and Form D to reference material. FIG. 6 also shows the new pattern that resulted from exposing Form A to thermal stress along with the Form A pattern that resulted after three additional days at room temperature.

Example 5

Recrystallization Procedures to Produce Form B from Compound 2

Recrystallization studies were conducted to define a procedure to improve chromatographic purity. All recrystallization procedures in Table 7 involved dissolving Compound 2 in concentrated HCl and then adding the anti-solvent, acetone. The differences in the processes are subtle but important in terms of their results.

Recrystallization Process 1: Compound 1 was charged to an appropriately sized flask or reactor, dissolved in aqueous hydrochloric acid solution and heated to at least 55±10° C. The solution was stirred for about 45 minutes and the resulting mixture was filtered through an in-line filter. Acetone was added at 55±10° C. over the course of an hour and the solution was stirred for about an additional hour. The temperature was decreased to about 25±5° C., and the solution was stirred for at least 2 hours. The solids were collected by filtration, washed with acetone, and dried to afford Compound 2 form B.

Recrystallization Process 2: Compound 1 was charged to an appropriately sized flask or reactor, dissolved in aqueous hydrochloric acid solution and heated to at least 55±10° C. The solution was stirred for about 45 minutes and the resulting mixture was filtered through an in-line filter. The temperature was decreased to about 25±5° C., and the solution was stirred for at least 2 hours. Acetone was added at 25±5° C. over the course of an hour and the solution was stirred for an additional two hours. The solids were collected by filtration, washed with acetone, and dried to afford Compound 2 form D.

Recrystallization Process 3: Compound 1 was charged to an appropriately sized flask or reactor, dissolved in aqueous hydrochloric acid solution and heated to at least 55±10° C. The solution was stirred for about 45 minutes and the resulting mixture was filtered through an in-line filter. The temperature was decreased to about 25±5° C. and the solution was stirred for at least 2 hours. The solids were collected by filtration, washed with acetone, and dried to afford Compound 2 form D.

TABLE 7

Effect of crystallization procedures on purging of chromatographic impurities from Compound 1

| RRT | % area | Recrys Process 1 % area | Recrys Process 2 % area | Recrys Process 3 % area |
|---|---|---|---|---|
| 1.11 | 1.13 | 1.11 | 0.87 | 0.27 |
| 1.37 | 0.14 | 0.15 | 0.13 | ND |
| 1.62 | 0.14 | ND | 0.13 | ND |

While conducting the experiments presented in Table 7, it was discovered that not all recrystallization processes resulted in the preferred solid state form, Form B. Specifically, Recrystallization Processes 2 and 3 result in a different solid state form (putative Form D) whereas Recrystallization 1 reproducibly provides Form B. In one embodiment, Compound 2 is converted to Form D by Recrystallization Procedure 2 and 3 and Form D is converted to Form B by Recrystallization Process 1.

Example 6

XRPD Analysis of Compound 2, Morphic Form B

The XRPD pattern of Form B was collected with a PANalytical X'Pert PRO MPD diffractometer using an incident beam of Cu radiation produced using an Optix long, fine-focus source. An elliptically graded multilayer mirror was used to focus Cu Kα X-rays through the specimens and onto the detector. Prior to the analysis, a silicon specimen (NIST SRM 640e) was analyzed to verify the observed position of the Si 111 peak is consistent with the NIST-certified position. The sample was sandwiched between 3-μm-thick films and analyzed in transmission geometry. A beamstop, short anti-scatter extension and an anti-scatter knife edge were used to minimize the background generated by air. Soller slits for the incident and diffracted beams were used to minimize broadening from axial divergence. The diffraction patterns were collected using a scanning position-sensitive detector (X'Celerator) located 240 mm from the specimens and Data Collector software v. 2.2b. Data acquisition parameters for each pattern are displayed above the image in the Data section of this report including the divergence slit (DS) before the mirror.

The XRPD pattern of pure Form B along with the indexing solution is shown in FIG. 7. The pure Form B XRPD pattern exhibited sharp peaks, indicating the sample was composed of crystalline material. The allowed peak positions from the XRPD indexing solution are 6.5, 8.1, 9.4, 9.6, 10.2, 10.6, 11.2, 12.2, 12.9, 13.0, 13.3, 13.4, 14.0, 14.4, 14.6, 15.0, 15.9, 16.2, 16.4, 16.5, 16.8, 18.1, 18.4, 18.5, 18.6, 18.6, 18.9, 19.1, 19.2, 19.3, 19.4, 19.5, 19.6, 19.7, 19.8, 19.9, 20.4, 20.6, 21.3, 21.4, 21.8, 22.0, 22.2, 22.3, 22.4, 22.5, 22.8, 23.0, 23.1, 23.4, 23.8, 24.1, 24.2, 24.3, 24.4, 24.5, 24.6, 25.4, 25.6, 25.7, 25.9, 26.0, 26.1, 26.3, 26.4, 26.5, 26.6, 26.7, 26.8, 26.9, 27.2, 27.3, 27.5, 27.6, 27.7, 27.9, 28.3, 28.4, 28.5, 28.7, 28.9, 29.0, 29.1, 29.3, 29.4, 29.5, 29.6, 29.7, 29.8, 29.9, 30.0, 30.3, 30.4, 30.5, 30.6, 30.7, 30.9, 31.2, 31.5, 31.6, 31.7, 31.8, 31.9, 32.0, 32.2, 32.3, 32.4, 32.5, 32.6, 32.7, 32.8, 33.1, 33.2, 33.3, 33.6, 33.7, 33.8, 34.0, 34.1, 34.2, 34.3, 34.6, 34.7, 34.8, 35.0 35.2, 35.3, 35.5, 35.6, 35.9, 36.0, 36.2, 36.5, 36.6, 36.7, 36.8, 36.9, 37.1, 37.2, 37.3, 37.4, 37.5, 37.6, 37.7, 37.8, 37.9, 38.2, 38.3, 38.4, 38.5, 38.6, 38.7, 38.8, 38.9, 39.0, 39.1, 39.2, 39.3, 39.4, 39.5, 39.6, 39.7, 39.8, 39.9, and 40.0° 2θ.

For example, Form B's XRPD may be indexed as follows 6.47, 8.08, 9.42, 9.59, 10.18, 10.62, 11.22, 12.17, 12.91, 12.97, 13.27, 13.37, 14.03, 14.37, 14.63, 15.02, 15.93, 16.20, 16.35, 16.43, 16.47, 16.81, 18.10, 18.35, 18.41, 18.50, 18.55, 18.6,0 18.91, 19.11, 19.15, 19.24, 19.34, 19.43, 19.51, 19.61, 19.65, 19.76, 19.85, 19.90, 20.44, 20.61, 21.34, 21.43, 21.84, 21.95, 22.17, 22.28, 22.30, 22.33, 22.44, 22.54, 22.76, 22.81, 22.97, 23.00, 23.11, 23.42, 23.80, 24.11, 24.22, 24.34, 24.38, 24.40, 24.48, 24.56, 24.57, 25.40, 25.56, 25.57, 25.59, 25.72, 25.74, 25.94, 25.99, 26.11, 26.28, 26.29, 26.37, 26.51, 26.58, 26.61, 26.73, 26.81, 26.92, 27.15, 27.19, 27.23, 27.31, 27.49, 27.57, 27.61, 27.71, 27.88, 27.94, 28.27, 28.41, 28.53, 28.71, 28.74 28.86, 28.94, 28.98, 29.03, 29.06, 29.08, 29.25, 29.30, 29.38, 29.51, 29.57, 29.61, 29.70, 29.73, 29.75, 29.90, 29.95, 30.31, 30.38, 30.42, 30.54, 30.55, 30.66, 30.73, 30.85, 30.87, 30.89, 31.23, 31.51, 31.55, 31.61, 31.70, 31.76, 31.77, 31.80, 31.81, 31.82, 31.82, 31.90, 31.91, 31.95, 32.17, 32.21, 32.23, 32.25, 32.36, 32.37, 32.43, 32.53, 32.54, 32.56, 32.61, 32.73, 32.80, 32.82, 33.05, 33.13, 33.17, 33.22, 33.28, 33.30, 33.60, 33.65, 33.71, 33.76, 33.77, 33.99, 34.01, 34.01, 34.05, 34.10, 34.17, 34.29, 34.55, 34.60, 34.62, 34.63, 34.68, 34.75, 34.76, 35.03, 35.16, 35.19, 35.21, 35.25, 35.31, 35.46, 35.61, 35.63, 35.85, 35.86, 35.90, 35.97, 36.19, 36.45, 36.56, 36.58, 36.67, 36.68, 36.70, 36.71, 36.77, 36.85, 36.87, 36.90, 37.09, 37.19, 37.27, 37.28, 37.29, 37.32, 37.33, 37.37, 37.38, 37.48, 37.48, 37.50, 37.51, 37.54, 37.61, 37.64, 37.65, 37.68, 37.69, 37.71, 37.74, 37.74, 37.76, 37.81, 37.83, 37.93, 37.94, 38.15, 38.19, 38.32, 38.36, 38.39, 38.46, 38.59, 38.63, 38.69, 38.76, 38.79, 38.85, 38.87, 38.88, 38.96, 38.98, 39.02, 39.05, 39.19, 39.27, 39.33, 39.36, 39.39, 39.43, 39.44, 39.53, 39.53, 39.6, 39.61, 39.70, 39.71, 39.72, 39.82, 39.87, 39.9, and 39.98 ° 2θ.

Observed peaks for Form B include 9.5±0.2, 18.1±0.2, 19.3±0.2, 22.4±0.2, 26.6±0.2, and 27.7±0.2, ° 2θ.

Agreement between the allowed peak positions, marked with bars, and the observed peaks indicated a consistent unit cell determination. Successful indexing of the pattern indicated that the sample was composed primarily of a single crystalline phase. Space groups consistent with the assigned extinction symbol, unit cell parameters, and derived quantities are given in Table 8.

TABLE 8

Parameters of the XRPD of Compound 2, Form B

| | |
|---|---|
| Bravais Type | C-centered Monoclinic |
| a [Å] | 27.719 |
| b [Å] | 9.796 |
| c [Å] | 22.221 |
| α [deg] | 90 |
| β [deg] | 100.16 |
| γ [deg] | 90 |
| Volume [Å³/cell] | 5,939.0 |
| Chiral contents | Not specified |
| Extinction Symbol | C 1 c 1 |
| Space Group(s) | Cc (9), C2/c (15) |

In one embodiment, Form B is characterized by an XRPD pattern comprising at least two 2theta values selected from 6.5±0.2°, 9.5±0.2°, 14.0±0.2°, 14.4±0.2°, 18.1±0.2°, 19.9±0.2°, and 22.4±0.2°. In one embodiment, Form B is characterized by an XRPD pattern comprising at least three 2theta values selected from 6.5±0.2°, 9.5±0.2°, 14.0±0.2°, 14.4±0.2°, 18.1±0.2°, 19.9±0.2°, and 22.4±0.2°. In one embodiment, Form B is characterized by an XRPD pattern comprising at least four 2theta values selected from 6.5±0.2°, 9.5±0.2°, 14.0±0.2°, 14.4±0.2°, 18.1±0.2°, 19.9±0.2°, and 22.4±0.2°. In one embodiment, Form B is characterized by an XRPD pattern comprising at least five 2theta values selected from 6.5±0.2°, 9.5±0.2°, 14.0±0.2°, 14.4±0.2°, 18.1±0.2°, 19.9±0.2°, and 22.4±0.2°. In one embodiment, Form B is characterized by an XRPD pattern comprising at least six 2theta values selected from 6.5±0.2°, 9.5±0.2°, 14.0±0.2°, 14.4±0.2°, 18.1±0.2°, 19.9±0.2°, and 22.4±0.2°. In one embodiment, Form B is characterized by an XRPD pattern comprising the 2theta values selected from 6.5±0.2°, 9.5±0.2°, 14.0±0.2°, 14.4±0.2°, 18.1±0.2°, 19.9±0.2°, and 22.4±0.2°. In one embodiment, Form B is characterized by an XRPD pattern comprising at least the 2theta value of 9.5±0.4°.

Example 7

Six- and Twelve-Month Stability Study of Form B at 25° C./60% RH and at 40° C./75% RH Conditions Form B was stored at 25° C./60% RH for twelve months and at 40° C./75% RH for six months.

Table 9 shows the results from the 25° C./60% RH storage conditions and Table 10 shows the results at the 40° C./75% RH. In both conditions, Form B was 99.5% pure and the XRPD spectrum conformed to the reference spectrum at the longest time point studied.

TABLE 9

Twelve-month Stability Study at the 25° C./60% RH Conditions

| | Storage Time | | | | |
|---|---|---|---|---|---|
| Test | 0 M | 3 M | 6 M | 9 M | 12 M |
| Appearance | Yellow solid | Yellow solid | Yellow solid | Yellow solid | Yellow solid |
| Moisture (%) | 4.9% | 4.07% | 7.53% | 7.29% | 7.48% |
| XRPD | Form B | N/A | N/A | N/A | Form B |
| HPLC Purity | 99.5% | 99.5% | 99.5% | 99.6% | 99.5% |

TABLE 10

Six-month Stability Study at the 40° C./75% RH Conditions

| | Storage Time | | | |
|---|---|---|---|---|
| Test | 0 M | 1 M | 3 M | 6 M |
| Appearance | Yellow solid | Yellow solid | Yellow solid | Yellow solid |
| Moisture (%) | 4.9% | 2.75% | 7.47% | 7.53% |
| XRPD | Form B | N/A | Form B | Form B |
| HPLC Purity | 99.5% | 99.5% | 99.5% | 99.5% |

Example 8

Conversion of Impure Form B Material to Pure Form B Material

Figure 8:
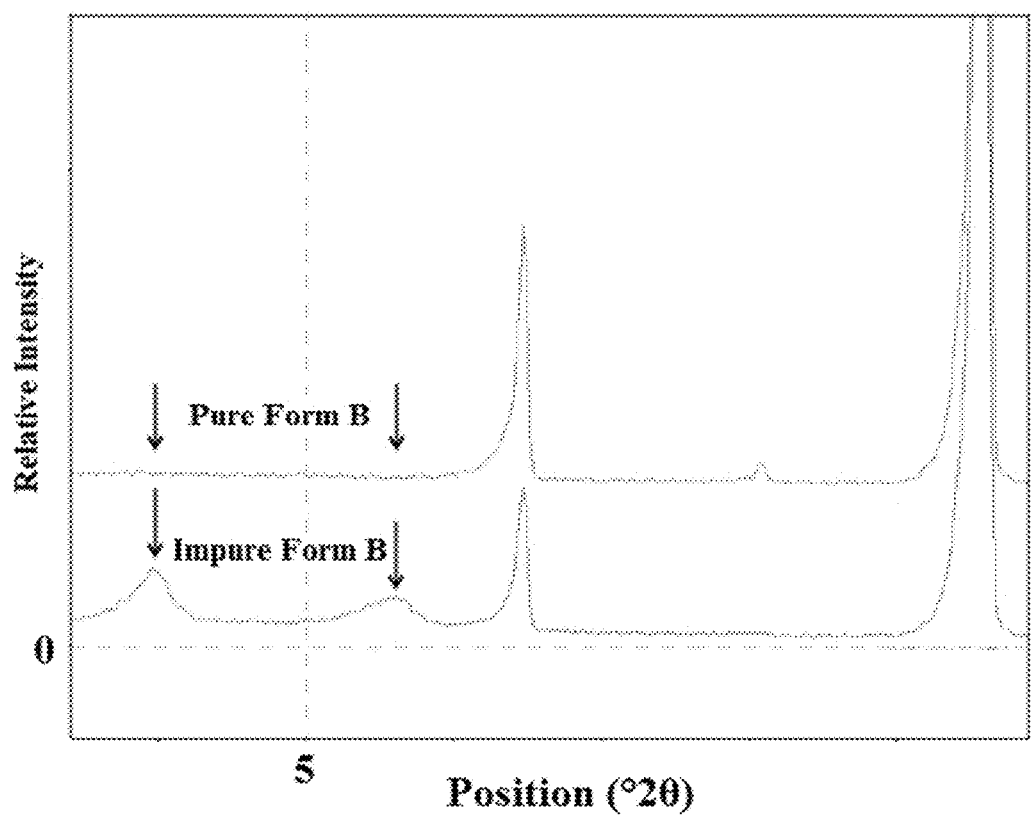
FIG. 8 is a comparison of the XRPD patterns of impure Form B material and pure Form B material as characterized in Example 6. Impure Form B material has two peaks at approximately 4.0 and 5.6 degrees that are missing in the pure Form B material. The x-axis is 2Theta measured in degrees and the y-axis is relative intensity as a means to compare the two Form B materials.

Pure Form B was isolated from impure Form B, material that was characterized as containing a residual amount of an unknown form in addition to Form B. The difference in the XRPD patterns of impure Form B and pure Form B is shown in FIG. 8. (In the following experiments described below, pure Form B is the Form B as characterized in Example 6.) The pattern of pure Form B is visually similar to the pattern of impure Form B, with the exception of the absence of peaks at 2-theta angles of approximately 4.0 and 5.6°. As is common in XRPD analysis, there are also differences in relative peak intensities that are likely due to preferred orientation and/or particle statistics effects.

Solubility studies, small scouting experiments, and experiments with drying conditions were first performed to confirm the conditions suitable for the conversion to pure Form B. TG-IR Characterization was performed on a number of isolated samples of Form B. Once conditions were confirmed, the conversion from impure material to pure material was conducted in water:acetone 1:2 (v/v) slurry at 125 mg/mL concentration and 30° C. for 43 hours as described in more detail below.

Solubility Estimate Experiments for the Development of Conditions Suitable for Recrystallization Solubility estimates of impure Form B were attempted in various predominantly HCl acidic aqueous acetone solvent mixtures using an aliquot addition method that involved visual observation. Aliquots of various solvents or diluent/organic solvent mixtures were added to measured amounts of impure Form B with agitation (typically sonication) at ambient temperature until complete dissolution was achieved, as judged by visual observation. Solubilities were calculated based on the total solvent used to give a solution; actual solubilities may be greater because of the volume of solvent portions utilized or a slow rate of dissolution. If dissolution did not occur as determined by visual assessment, the value was reported as "<". If dissolution occurred at the first aliquot, the value was reported as ">". Due to the haziness of the obtained samples, effective solubility estimates were difficult to discern. In general, impure Form B showed very limited solubility (3-7 mg/mL) in the tested solvent mixtures (Table 11).

TABLE 11

Approximate Solubility of Impure Form B

| Solvent/<br>Solvent System | Temperature<br>(° C.) | Solubility[a] (mg/mL) | Observation |
|---|---|---|---|
| 1M HCl:acetone 20:80 | ambient | <1 | solids remained |
| 0.5M HCl:acetone 20:80 | ambient | <1 | solids remained |
| 0.1M HCl:acetone 20:80 | ambient | <1 | solids remained |
| 1M HCl:acetone 10:90 | ambient | <1 | solids remained |
| 0.5M HCl:acetone 10:90 | ambient | <1 | solids remained |
| 1M HCl:acetone 5:95 | ambient | <1 | solids remained |
| 1M HCl:acetone 33:67 | ambient | 2 | hazy solution |
| 1M HCl:acetone 50:50 | ambient | 4 | hazy solution |
| 1M HCl:acetone 60:40 | ambient | 4 | hazy solution |
| 1M HCl:acetone 67:33 | ambient | 6 | hazy solution |
| 1.0M HCl:acetone 75:25 | ambient | 7 | hazy solution |
| 2.0M HCl | ambient | 4 | hazy solution |
| 5.0M HCl | ambient | 3 | hazy solution |
| Water | ambient | <7 | solids remained |
| Water:acetone 1:2 | ambient | 3 | hazy solution |
| Water:cetone 3:1 | ambient | <3 | solids remained |
| 5.0M HCl:water 1:2 | ambient | 7 | clear solution |

[a]Solubilities were calculated based on the total solvent used to give a solution; actual solubilities may be greater because of the volume of the solvent portions used or a slow rate of dissolution. Values are rounded to whole number. If dissolution did not occur as determined by visual assessment, the value is reported as "<". If dissolution occurred as determined by the visual assessment after the addition of the first aliquot, the value is reported as ">".

Figure 9:
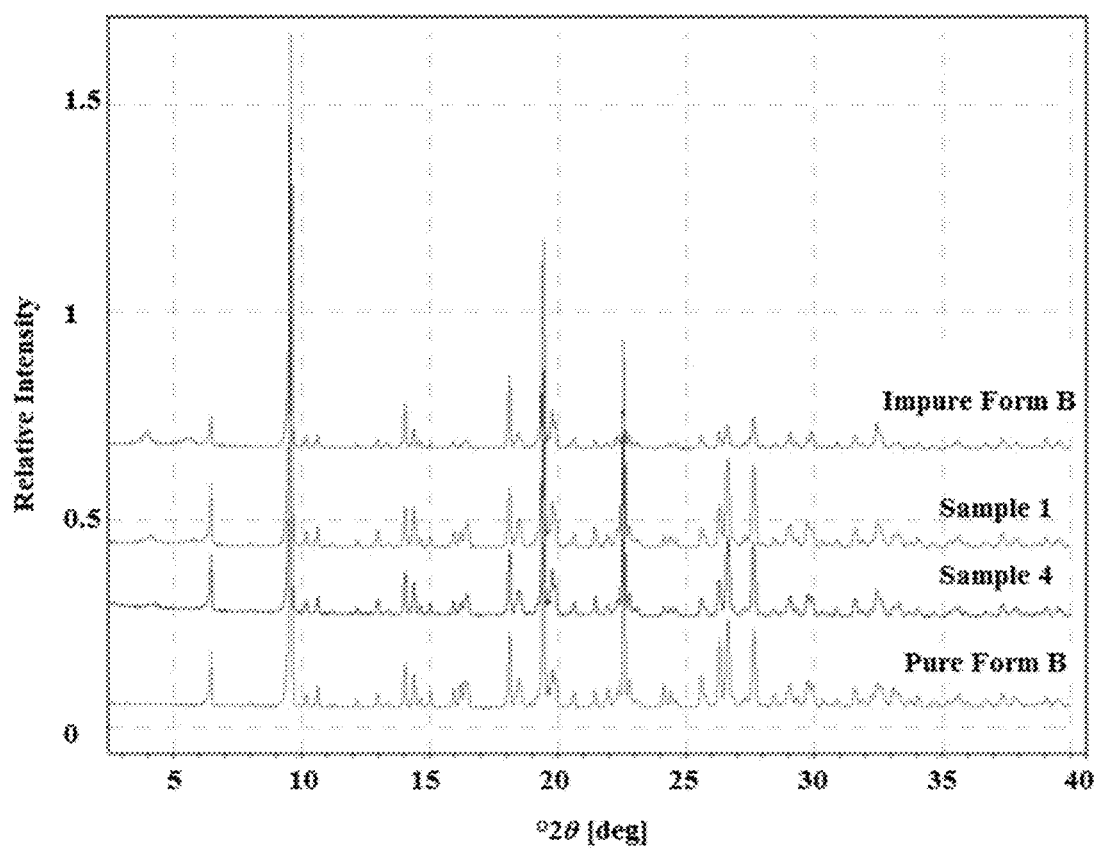
FIG. 9 is a comparison of impure Form B, Samples 1 and 4 from the slurry experiment described in Example 8, and pure Form B. Pure Form B is the Form B characterized in Example 6. A number of experiments were conducted to convert impure Form B to pure Form B material, including a slurry experiment with 1:1 (v/v) 0.1 M HCl:acetone (Sample 1) and 1:2 (v/v) 0.5 M HCl:acetone (Sample 4). The acidic aqueous acetone mixtures failed to convert impure material to pure material. The XRPD patterns of Sample 1 and 4 were not consistent with the XRPD pattern of pure Form B since a peak at approximately 4.0 degrees was still present. The x-axis is relative humidity measured as a percent and the y-axis is weight of water of the material measured as a percent.

Small-Scale Scouting Experiments Towards the Development of Conditions Suitable for Recrystallization Approximately 16 small scale slurry experiments were carried out by varying the slurry concentration, temperature, HCl acid molar concentration, and content in the aqueous acetone mixtures as well as the water content. Slurries of impure Form B were performed in a given solvent system at targeted calculated concentration at ambient or elevated temperatures for various time/durations. The solids were isolated by vacuum filtration and submitted for XRPD analysis. The specific experimental conditions are detailed in Table 12 where solvent system ratios are by volume. The slurries in acidic aqueous acetone mixtures (Samples 1, 2, and 4) at ambient temperature failed to convert impure Form B to pure Form B. FIG. 9 compares the XRPD patterns of Samples 1 and 4 to the XRPD pattern of the starting material of the experiments, impure Form B. FIG. 9 also compares Samples 1 and 4 to pure Form B material previously characterized in Example 6.

Figure 10:
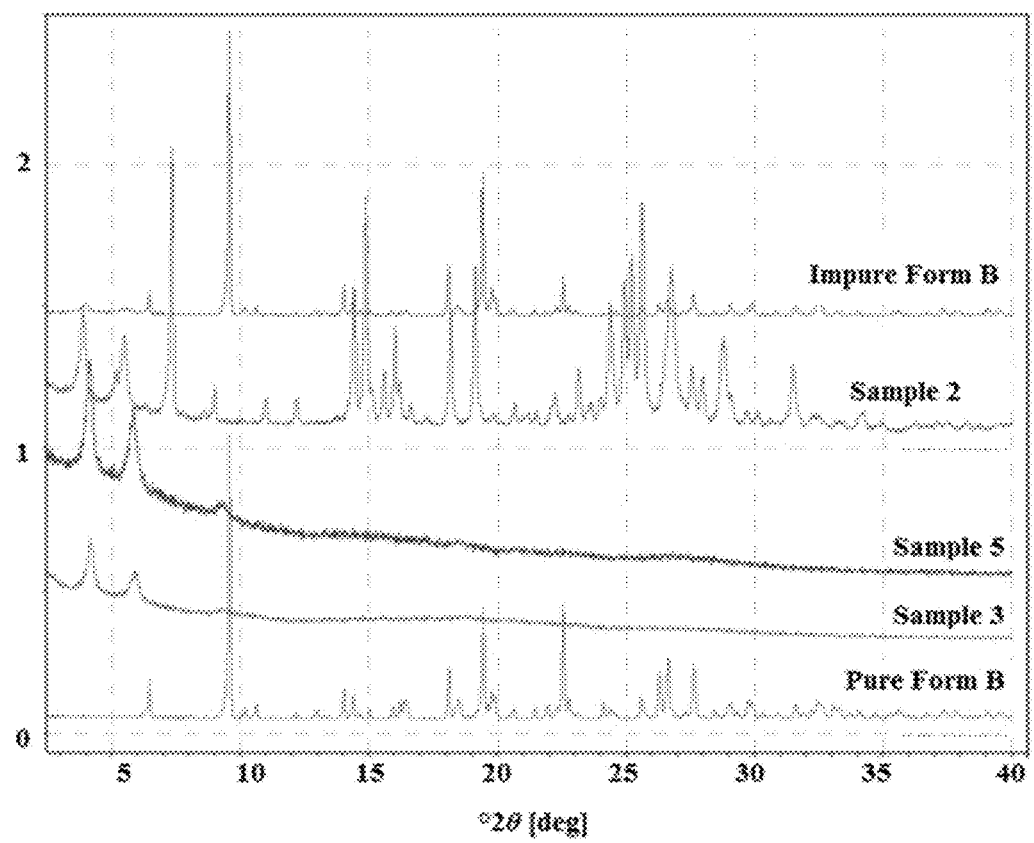
FIG. 10 is a comparison of impure samples of Form B, Samples 3 and 5 from the slurry experiment described in Example 8, and pure Form B. A number of experiments were conducted to convert impure Form B to pure Form B material, including a slurry experiment with 75:25 (v/v) 0.1 M HCl:acetone (Sample 3) and 50:50 (v/v) 0.5 M HCl:acetone (Sample 5). The acidic aqueous acetone mixtures failed to convert impure material to pure material. Pure Form B is the Form B characterized in Example 6. Impure Form B is the material used as starting material in the slurry experiments and impure Form B Sample 2 is a second impure form used as a reference. The x-axis is relative humidity measured as a percent and the y-axis is weight of water of the material measured as a percent.

The slurries in acidic aqueous acetone mixtures at an elevated temperature of 50° C. (Samples 3 and 5) produced a disordered material with two broad low angle peaks material suggestive of a potential mesophase. FIG. 10 compares XRPD patterns of Sample 3 and 5 to the starting material of the experiments, impure Form B and to pure Form B. For comparison purposes, the samples were also compared to a second impure sample of Form B, (Impure Form B Sample 2 in FIG. 10). This second impure Form B contained larger amounts of the unknown Form than the impure Form B previously described in Example 8. When increasing the molar concentration of HCl from 0.1 M (Sample 3) to 0.5 M (Sample 5), the intensity of these two peaks also increased.

Figure 11:
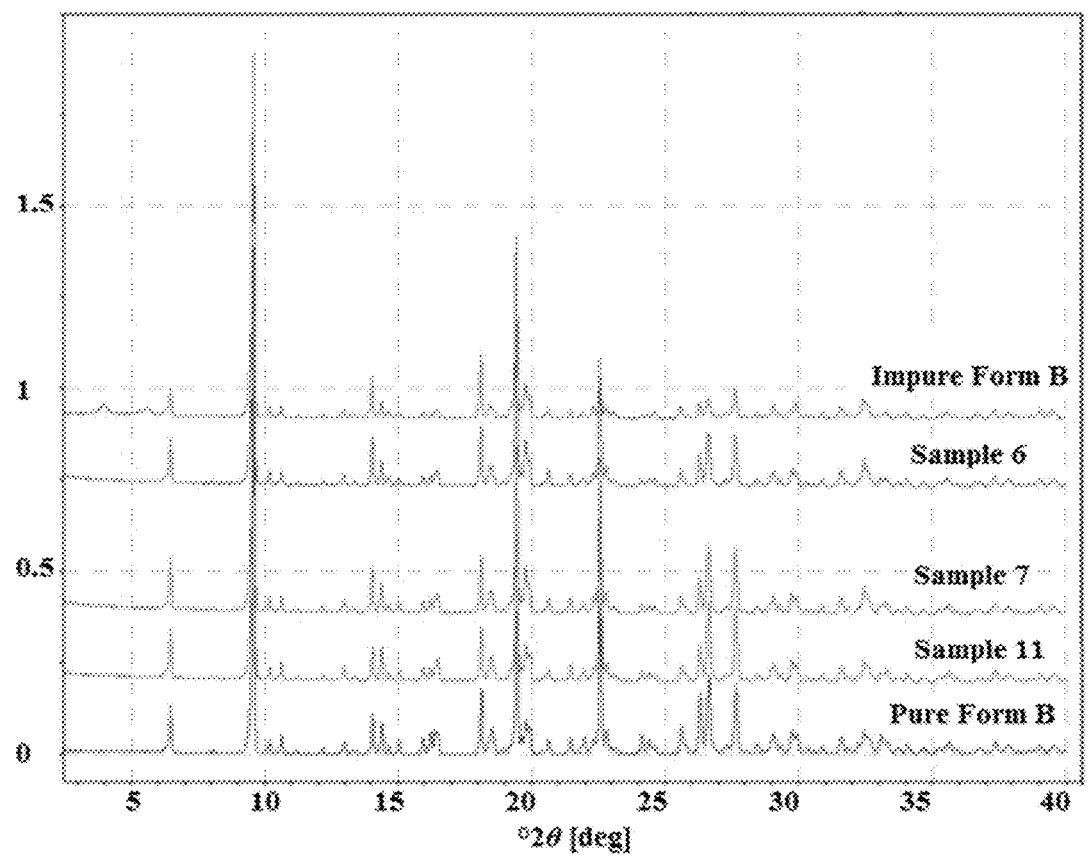
FIG. 11 is a comparison of impure Form B, Samples 6, 7, and 11 from the slurry experiment described in Example 8, and pure Form B. A number of experiments were conducted to convert impure Form B to pure Form B material, including slurry experiments with 1:2 (v/v) water:acetone that stirred at room temperature. Samples 6, 7, and 11 varied in the concentration of impure Form B and the length of time that the samples stirred (details are given in Table 12). All three conditions converted impure Form B to pure Form B since the XRPD patterns from Samples 6, 7, and 11 matched the pure Form B XRPD pattern. Pure Form B is the Form B characterized in Example 6 and impure Form B is the material used as staring material in the slurry experiments. The x-axis is relative humidity measured as a percent and the y-axis is weight of water of the material measured as a percent.

Several slurry experiments were performed in water:acetone solvent systems starting with impure Form B and varying the water:acetone ratio, slurry concentration, and time. Based on the initial slurry results, experiments in 1:2 (v/v) water:acetone at ambient temperature were performed with aliquots taken after 16 hours (Sample 6) and 20.5 hours (Sample 7). The slurry in this solvent system was conducted at a concentration of 100-125 mg/mL and ambient temperature. The XRPD patterns of the resulting materials were consistent with pure Form B (FIG. 11). Using a water:acetone (1:2) solvent system resulted in a low yield of 78-79% that was calculated for solids isolated by vacuum filtration without drying.

Figure 12:
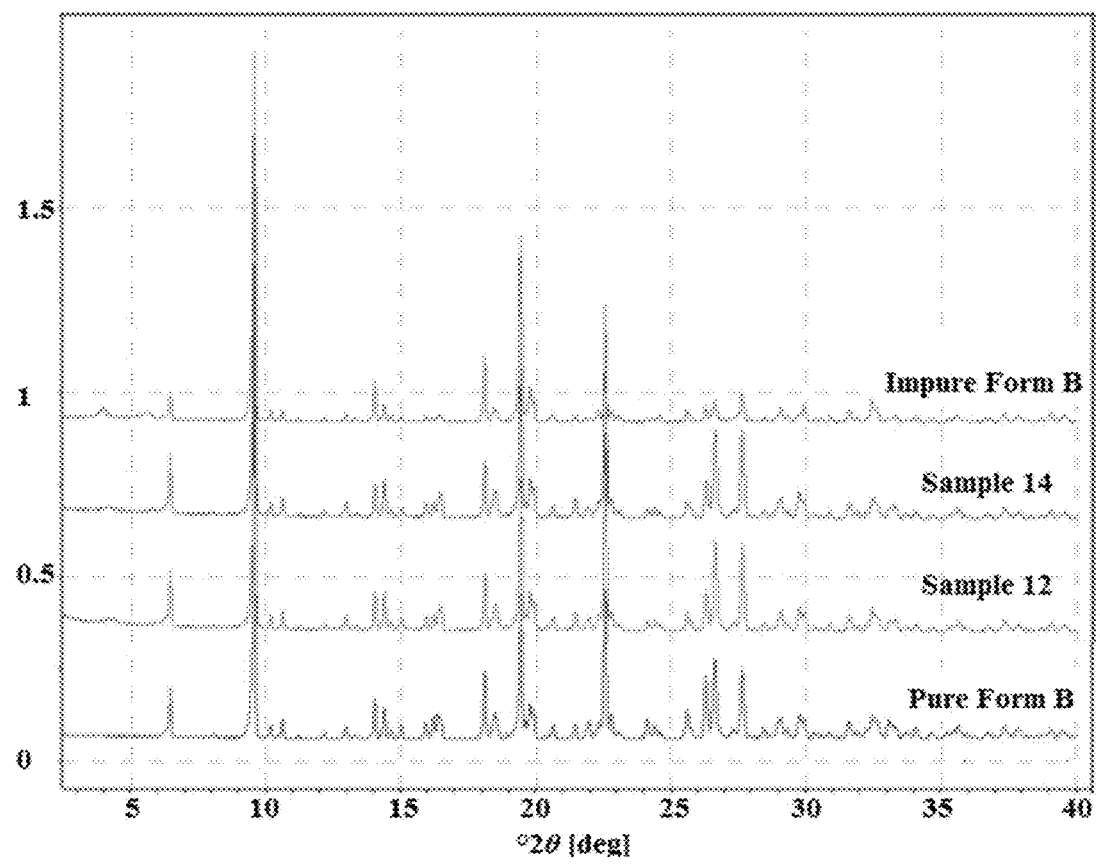
FIG. 12 is a comparison of impure Form B, Samples 12 and 14 from the slurry experiment described in Example 8, and pure Form B. Slurry experiments with 1:3 (v/v) water:acetone (Sample 14) and 1:2 water:acetone followed by additional acetone (Sample 12) were conducted in an effort to improve the yield of the recrystallization process. The XRPD patterns of Samples 12 and 14 were not consistent with the XRPD pattern of Form B since a peak at approximately 4.0 degrees was still present. Pure Form B is the Form B characterized in Example 6 and impure Form B is the material used as staring material in the slurry experiments. The x-axis is relative humidity measured as a percent and the y-axis is weight of water of the material measured as a percent.

In an effort to improve the yield, water:acetone 1:3 (v/v) was used at 150 mg/mL concentration (Samples 13 and 14) however, the conversion was not completed even after 4 days (FIG. 12). Therefore, one experiment was performed using water:acetone 1:2 (v/v) slurry for 18 hours and then adding acetone to reach ratio water:acetone 1:4 (v/v) followed by slurry for 4 hours (Sample 12). The XRPD pattern of the resulting material was consistent with Form B, however, one of the undesired peaks reappeared shifted from 3.95 ° 2θ to 4.2 ° 2θ (FIG. 12).

TABLE 12.

Small-scale Slurry Experiment Conditions and Results

| Sample ID | Solvent System[a] | Conditions | Observation | XRPD Result |
|---|---|---|---|---|
| 1 | 0.5M HCl:acetone 1:1 | 100 mg/mL Slurry, RT, 3 days | Dark yellow solids | B + broad peaks at 3.95 °2θ and 5.55 °2θ |
| 2 | 2.0M HCl | 150 mg/mL Slurry, RT, 3 days | Light yellow solids | B + A |
| 3 | 0.1M HCl:acetone 75:25 | 100 mg/mL | Yellow orange mobile suspension | Two low angle peaks in disordered material |
| 4 | 0.1M HCl:acetone 1:2 | Slurry, 50° C., 15 h | Bright yellow mobile suspension | Form B + broad peak at 3.95 °2θ |

TABLE 12.-continued

Small-scale Slurry Experiment Conditions and Results

| Sample ID | Solvent System[a] | Conditions | Observation | XRPD Result |
|---|---|---|---|---|
| 5 | 0.5M HCl:acetone 50:50 | 100 mg/mL Slurry, RT, 16 h | Dark orange mobile suspension | Two low angle peaks in disordered material |
| 6 | water:acetone 1:2 | 100 mg/mL Slurry, RT, 16 h | Bright yellow mobile suspension | Form B |
| 7 | | 100 mg/mL Slurry, RT, 20.5 h | Bright yellow mobile suspension | Form B |
| 8 | | 100 mg/mL Slurry, RT, 5 days | Bright yellow mobile suspension | Not analyzed |
| 9 | water:acetone 1:2 | 150 mg/mL Slurry, RT, 20 h | | Form B + broad smaller peak at 4.2 °2θ |
| 10 | | 150 mg/mL Slurry, RT, 4 days | Bright yellow suspension with ribbon of orange solids below solvent line | Not analyzed |
| 11 | water:acetone 1:2 | 125 mg/mL Slurry, RT, 20 h | Bright yellow mobile suspension | Form B |
| 12 | 1. water:acetone 1:2 2. water:acetone 1:4 | 1. 125 mg/mL, slurry, RT, 18 h 2. Acetone added to reach H2O:acetone 1:4 3. Slurry, RT, 4 h | 1. Bright yellow mobile suspension 2. No observation 3. Bright yellow mobile suspension | Form B + small broad peak at 4.27 °2θ |
| 13 | water:acetone 1:3 | 150 mg/mL Slurry, RT, 20 h | | Form B + broad peaks at 4.2 °2θ and 5.9 °2θ |
| 14 | | 150 mg/mL Slurry, RT, 4 days | Bright yellow suspension with tiny ring of orange solids below solvent line | Form B + broad peaks at 4.2 °2θ and 5.7 °2θ |
| 15 | 0.1M HCl:EtOH 1:9 | 100 mg/mL Slurry, RT, 16 h | Bright yellow mobile suspension | Form B + broad peak at 3.95 °2θ |
| 16 | | 100 mg/mL Slurry, RT, 20.5 h | Bright yellow mobile suspension | Form B + broad peak at 3.95 °2θ |

Lara Controlled Laboratory Reactor Slurry Experiments

Several scale up experiments were carried out in efforts to demonstrate applicable conditions for the conversion of impure Form B to pure Form B. The slurry conversion experiment was performed using a 1 L round-bottomed controlled laboratory reactor (Radleys Lara CLR) equipped with a Teflon anchor impeller, Julabo temperature control unit, and temperature probe for monitoring of the reactor temperature throughout the experiment. The Julabo FP50 temperature control unit contained Julabo Thermal C10 fluid and the reactor temperature was measured with a K-type PTFE temperature probe. The experiments were carried out with Lara Control software version 2.3.5.0. The software tracked circulator temperature, vessel temperature, and stir rate, recording readings every tenth of a second throughout the experiment.

The reactor vessel was charged with the solids of impure Form B (58.86 g) in 471 mL of a water:acetone 1:2 (v/v) solvent system achieving 125 mg/mL slurry concentration (Samples 20-23). The resulting slurry was stirred at 30° C. for up to 43 hours with stirring speed of 400 rpm. The slurry was cooled to 25° C. over 30 minutes, discharged from the reactor vessel, and immediately slowly filtered (drop by drop) to dry land. A water:acetone 1:2 (v/v) wash solution was prepared in advance and used to wash the filter cake in one portion.

Pulls were taken usually at the 20th hour and if needed at later time points (Table 13). The scale up experiments showed that longer times and slightly elevated temperature (from ambient temperature to 30° C.) were needed at larger scale to convert impure Form B completely to pure Form B. Sample 22 was converted to pure Form B, while Samples 21 and 23 were not analyzed. Sample 20 resulted in Form B, but a broad peak was also observed at 4.2 ° 2θ.

TABLE 13

Scale-up Slurry Experimental Conditions and XRPD Results

| Sample ID | Solvent System (v/v) | Conditions | XRPD Result |
|---|---|---|---|
| 17 | water:acetone 30:70 | 125 mg/mL Slurry, RT, 18 h | B + broad peaks at 4.2 °2θ and 5.8 °2θ |
| 18 | | 125 mg/mL Slurry, RT, 23 h | B + broad peak at 4.2 °2θ |

TABLE 13-continued

Scale-up Slurry Experimental Conditions and XRPD Results

| Sample ID | Solvent System (v/v) | Conditions | XRPD Result |
|---|---|---|---|
| 19 | | 125 mg/mL Slurry, RT, 30 h | B + broad peaks at 4.2 °2θ and 5.8 °2θ |
| 20 | water:acetone 1:2 | 125 mg/mL Slurry, RT, 20 h | B + broad peak at 4.2 °2θ |
| 21 | | 125 mg/mL Slurry, RT, 45 h | Not analyzed |
| 22 | | 125 mg/mL Slurry, 30° C., 20 h | Form B |
| 23 | | 125 mg/mL Slurry, 30° C., 20.5 h | Not analyzed |

TG-IR Characterization of Compound 2, Form B

The TG analyses were performed using a TA Instrument Q5000 thermogravimetric analyzer. Temperature calibration was performed using nickel and Alumel. The sample was placed in a platinum pan and inserted into the TG furnace. The furnace was heated under a nitrogen purge to 350° C. at a rate of 10° C./min.

Thermogravimetric infrared (TG-IR) analysis was performed on a TA Instruments Q5000 IR thermogravimetric (TG) analyzer interfaced to a Magna-IR 560® Fourier transform infrared (FT-IR) spectrophotometer (Thermo Nicolet) equipped with an Ever-Glo mid/far IR source, a potassium bromide (KBr) beamsplitter, and a mercury cadmium telluride (MCT-A) detector. The FT-IR wavelength verification was performed using polystyrene, and the TG calibration standards were nickel and Alumel™. The sample was placed in a platinum sample pan and the pan was inserted into the TG furnace. The TG instrument was started first, immediately followed by the FT-IR instrument. The TG instrument was operated under a flow of helium at 90 and 10 cc/minute for the purge and balance, respectively. The furnace was heated under helium at a rate of 20° C./minute to a final temperature of approximately 140° C. IR spectra were collected approximately every 32 seconds for approximately 7.5 minutes. Each IR spectrum represents 32 co-added scans collected at a spectral resolution of 4 cm-1. Volatiles were identified from a search of the High Resolution Nicolet Vapor Phase spectral library.

A TG-IR experiment was carried out on pure Form B (Sample 11 from the small-scale slurry experiments) at ambient temperature for 20 hours in an effort to investigate the stability of Form B at elevated temperature by monitoring potential release of hydrogen chloride.

Figure 13:
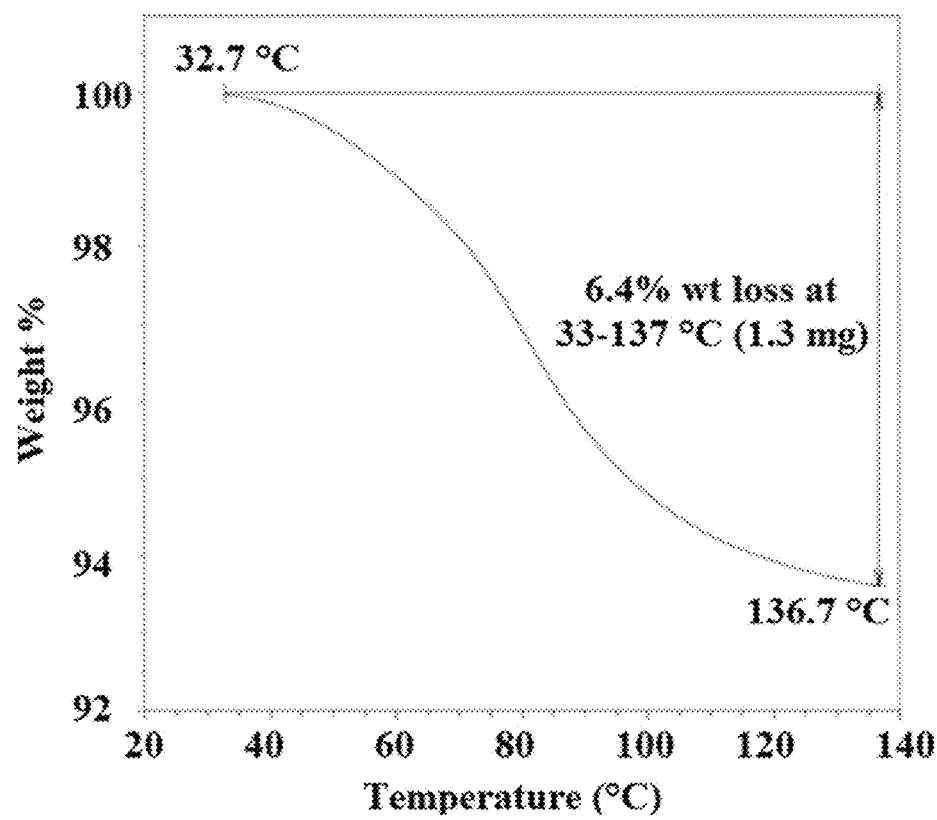
FIG. 13 is a graph from the TG-IR experiment of pure Form B, Sample 11 (Example 8). The TG data showed a 6.4% wt loss at 33-137° C. The x-axis is temperature measured in degrees Celsius and the y-axis is weight of the material measured as a percent.
Figure 14:
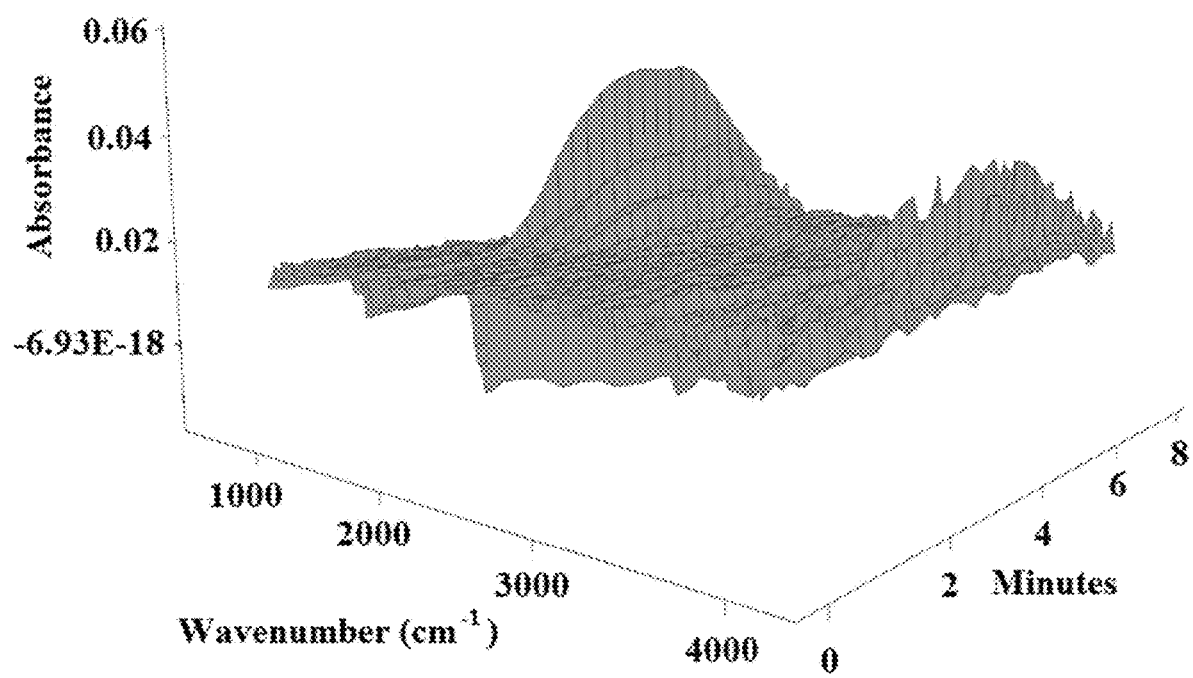
FIG. 14 is IR data from the TG-IR experiment of pure Form B, Sample 11 (Example 8). The x-axes are wavenumber measured in $cm^{-1}$ and time measured in minutes. The y-axis is absorbance.
Figure 15:
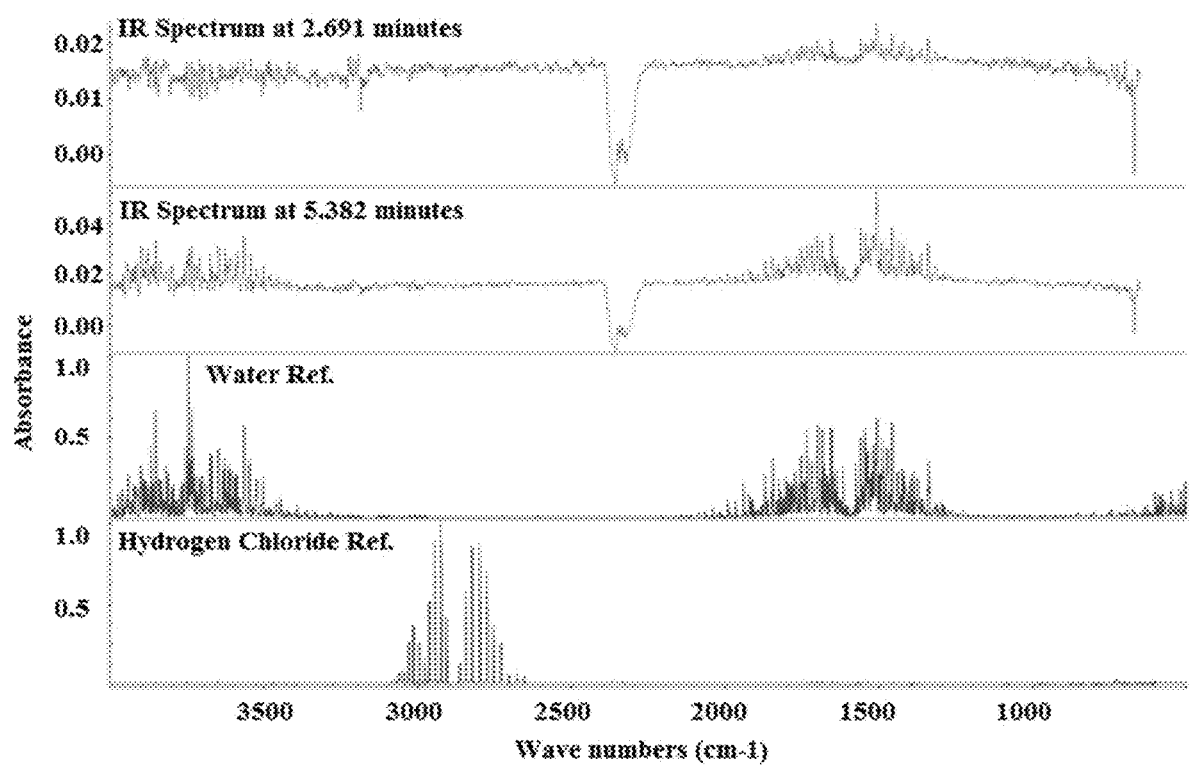
FIG. 15 compares IR spectra of pure Form B, Sample 11 obtained at 2.691 minutes and 5.382 minutes in the TG-IR experiment to IR spectra of water and hydrogen chloride. During the TG-IR experiment, only water, and no hydrogen chloride, was released as a volatile. The x-axis is wavenumber measured in $cm^{-1}$ and the y-axis is absorbance.

The TG data showed 6.4% weight loss at 33-137° C. (FIG. 13). The correlation between the time and temperature is presented in Table 14. The series of IR spectra collected during the TG-IR experiment are presented in FIG. 14 and FIG. 15. The spectra demonstrated that only water was detected as a volatile and that no hydrogen chloride was released.

TABLE 14

Correlation between Time and Temperature for TG-IR of Compound 2, Form B

| Time (min) | Temperature (° C.) | Weight (%) |
|---|---|---|
| 0.13 | 33.00 | 99.98 |
| 0.38 | 36.60 | 99.93 |
| 0.55 | 40.20 | 99.87 |
| 0.73 | 43.80 | 99.77 |
| 0.90 | 47.40 | 99.63 |
| 1.08 | 51.00 | 99.46 |
| 1.25 | 54.60 | 99.26 |

TABLE 14-continued

Correlation between Time and Temperature for TG-IR of Compound 2, Form B

| Time (min) | Temperature (° C.) | Weight (%) |
|---|---|---|
| 1.43 | 58.20 | 99.03 |
| 1.61 | 61.80 | 98.79 |
| 1.78 | 65.40 | 98.52 |
| 1.96 | 69.00 | 98.22 |
| 2.14 | 72.60 | 97.86 |
| 2.32 | 76.20 | 97.44 |
| 2.50 | 79.80 | 96.95 |
| 2.68 | 83.40 | 96.45 |
| 2.86 | 87.00 | 95.97 |
| 3.04 | 90.60 | 95.57 |
| 3.23 | 94.20 | 95.23 |
| 3.41 | 97.80 | 94.95 |
| 3.59 | 101.40 | 94.71 |
| 3.77 | 105.00 | 94.50 |
| 3.95 | 108.60 | 94.32 |
| 4.13 | 112.20 | 94.18 |
| 4.31 | 115.80 | 94.06 |
| 4.50 | 119.40 | 93.96 |
| 4.68 | 123.00 | 93.86 |
| 4.86 | 126.60 | 93.78 |
| 5.04 | 130.20 | 93.71 |
| 5.22 | 133.80 | 93.65 |

Drying Experiments of Compound 2, Form B

Weighted amounts of impure Form B and pure Form B samples from the previous experiments (Samples 14, 8, 11, 19, 21, and 23) were vacuum dried at ambient or elevated temperatures using various vacuum levels from approximately 14 in Hg up 27-28 in Hg. The resulting materials were weighted out prior to submission for XRPD analysis.

Figure 16:
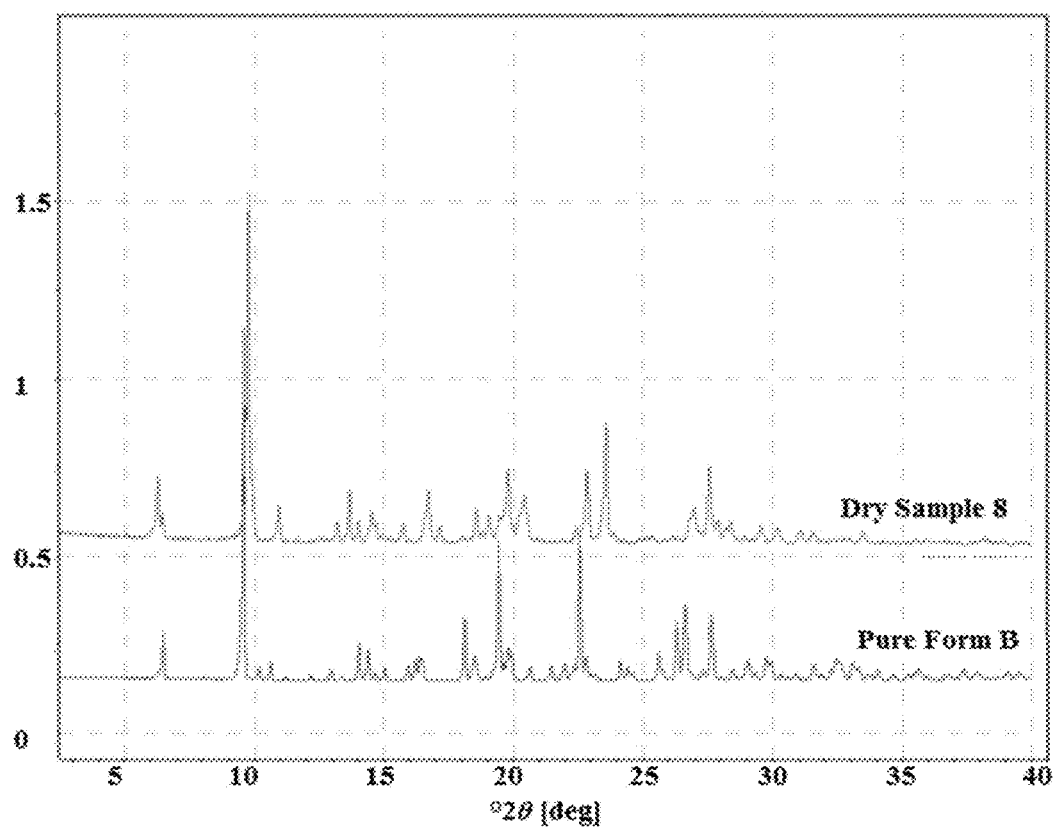
FIG. 16 is a comparison of Sample 8 dried in a vacuum oven for 15 hours at approximately 40° C. (Example 8, Table 15). The XRPD following the vacuum procedure did not correlate with the XRPD pattern of pure Form B. Dry sample 8 is a new crystalline Form. The x-axis is 2Theta measured in degrees and the y-axis is intensity measured in counts.

Two samples (Sample 14 and 8) were vacuum dried at 40° C. for 15 hours (approximately 29 in Hg) and demonstrated approximately 7.4% weight loss. One of the samples (Sample 8) was analyzed by XRPD and a new crystalline XRPD pattern was obtained (FIG. 16) that was not consistent with Form B.

Figure 17:
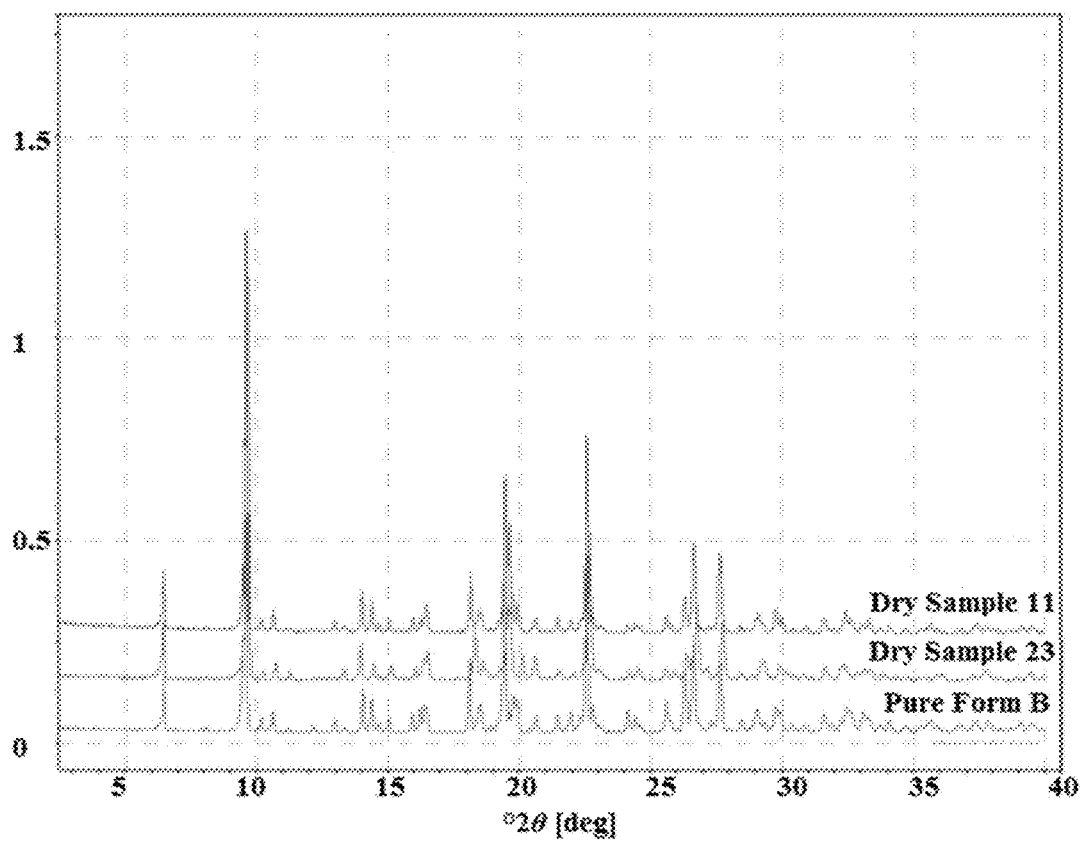
FIG. 17 are the XRPD patterns of Sample 11 and Sample 23 that were both dried in a vacuum oven, but under different conditions (Example 8, Table 15) compared to the XRPD pattern of pure Form B. Both Sample 11 and 23 exhibited XRPD patterns of Form B. The x-axis is 2Theta measured in degrees and the y-axis is intensity measured in counts.

Sample 11 was vacuum dried at ambient temperature for 0.5 hour (approximately 14 in Hg) demonstrating a 1.8% weight loss (calculated from weighing the sample before and after drying). The XRPD pattern of the resulting material was consistent with Form B, however, tiny shifting in a few peak positions in the XRPD pattern was observed (FIG. 17). Significant peak shifting was observed in the XRPD pattern of Sample 23 (FIG. 17) that was vacuum dried at ambient temperature for 1 h (approximately 27-28 in Hg) demonstrating an 4.7% weight loss (calculated from weighing the sample before and after drying).

TABLE 15

Drying Conditions and Results for Compound 2, Form B

| Sample Source | Conditions | Weight Loss (calculated by weight before and after drying) | XRPD Result |
|---|---|---|---|
| Sample 14 | Vacuum oven, ~40° C., 15 h (~29.5 in Hg) | Weight loss: 7.5% | Not analyzed |
| Sample 8 | Vacuum oven, ~40° C., 15 h (~29.5 in Hg) | Weight loss: 7.4% | New crystalline material, not indexable |
| Sample 14 | Vacuum oven, 23° C., 2 h (~29.5 in Hg) | Weight loss: 6.8% | Not analyzed |
| Sample 11 | Vacuum oven, 22° C., 0.5 h (~14 in Hg) | Weight loss: 1.8% | Form B tiny peak shifting |
| Sample 19 | Vacuum oven, RT, 1.0 h (~27-28 in Hg) | Weight loss: 9.7% | Form B + broad peaks at 4.3 °2θ |
| Sample 21 | Vacuum oven, 22° C., 0.5 h (~28 in Hg) | Weight loss: 30.6% | B + broad peaks at 4.2 °2θ and 5.8 °2θ |
| Sample 23 | Vacuum oven, 22° C., 1.0 h (~27-28 in Hg) | Weight loss: 4.7% | Most likely Form B shifted |

Conversion of Impure Form B to Pure Form B

The conversion of impure Form B to pure Form B was conducted in water:acetone 1:2 (v/v) slurry at 125 mg/mL concentration and 30° C. for 43 hours. Very slow filtration was observed and the wet cake was air-dried at ambient conditions for 3.5 hours followed by vacuum drying at ambient temperature and 15 in Hg for 0.5 hour and then at ~27 in Hg for 3.5 hours yielding 49.26 g (84%).

An XRPD pattern was obtained at different points in the conversion as shown in Table 16. After 42 hours of heating, XRPD analysis showed that impure Form B had completely converted to pure Form B. Once the material was filtered and dried, TG analysis was performed in addition to XRPD analysis.

Figure 18:
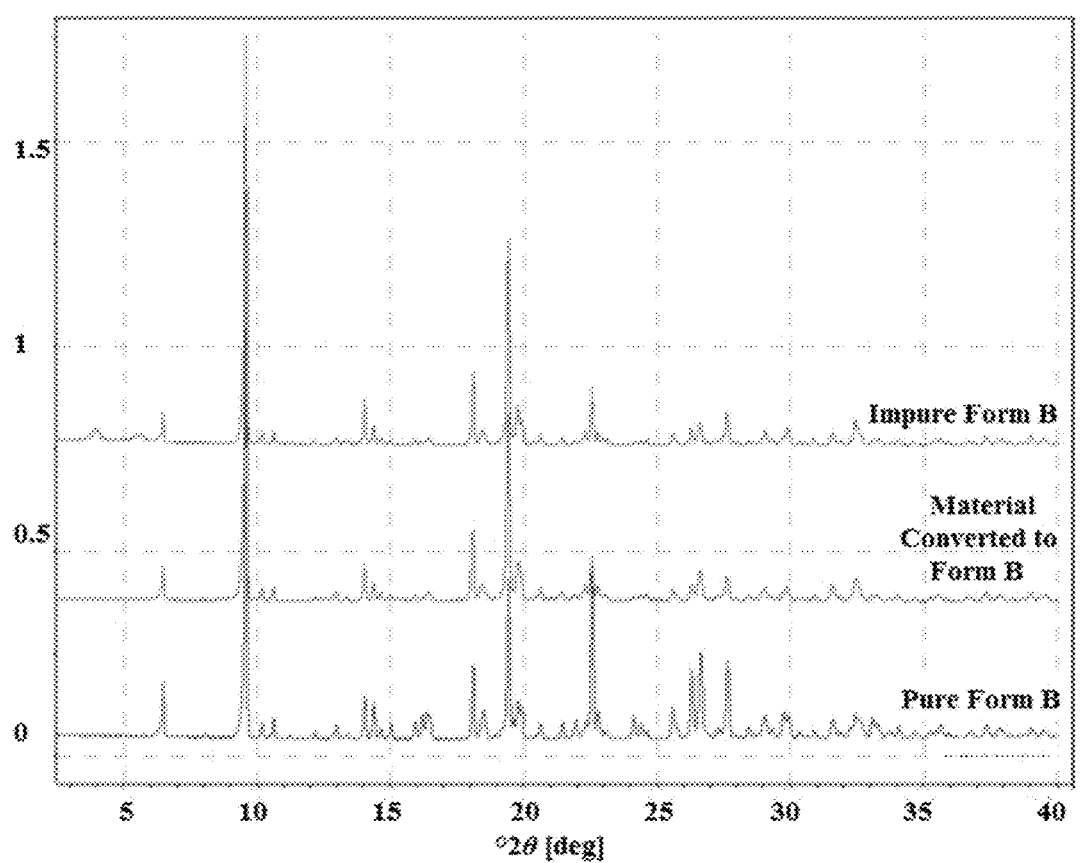
FIG. 18 is a comparison of XRPD patterns from impure Form B, pure Form B, and the material that was converted from impure Form B as described in Example 8. The XRPD pattern of the converted material aligned with the pure Form B material. Pure Form B is the Form B characterized in Example 6 and impure Form B is the material used as staring material in the conversion procedure. The x-axis is 2Theta measured in degrees and the y-axis is intensity measured in counts.

The XRPD pattern exhibited by the converted batch after drying was consistent with the XRPD pattern in FIG. 7 of pure Form B and its peaks aligned with the allowed peak positions from the pattern shown in FIG. 7. FIG. 18 compares the patterns of impure Form B, pure Form B as characterized in Example 6, and the pure Form B converted from impure Form B as described in Example 8.

Figure 19:
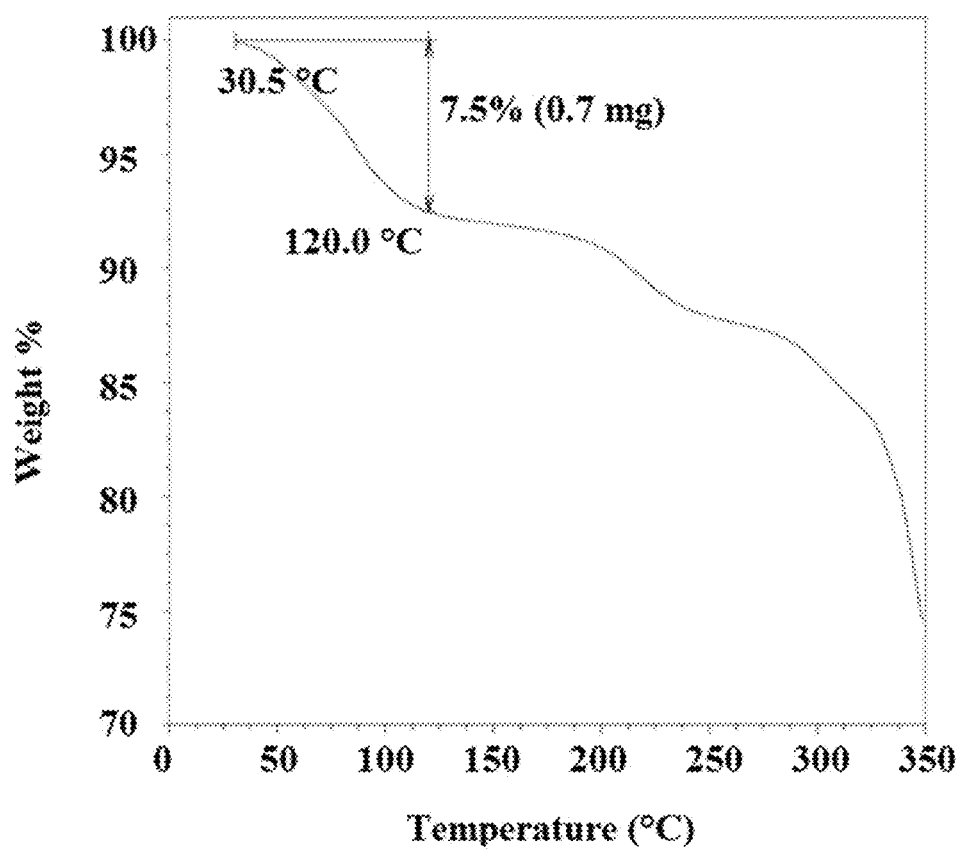
FIG. 19 is the TGA data from the batch converted to pure Form B material from impure Form B as described in Example 8. The TGA data showed a 7.6% weight loss at 31-120° C. it also showed an approximately 20% weight loss from 120-350° C. The x-axis is temperature measured in degrees Celsius and the y-axis is weight of the material measured as a percent.
Figure 20:
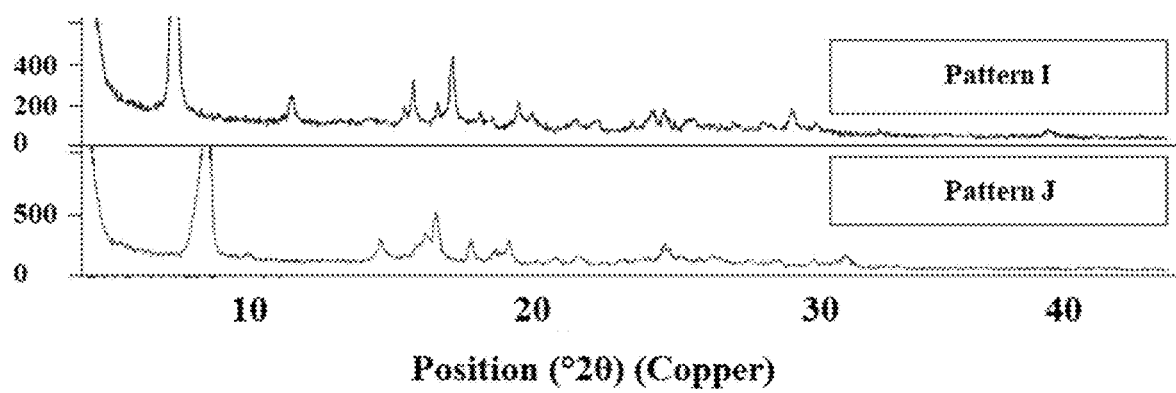
FIG. 20 are XRPD patterns of Form I and Form J. The x-axis is 2Theta measured in degrees and the y-axis is intensity measured in counts.
Figure 21:
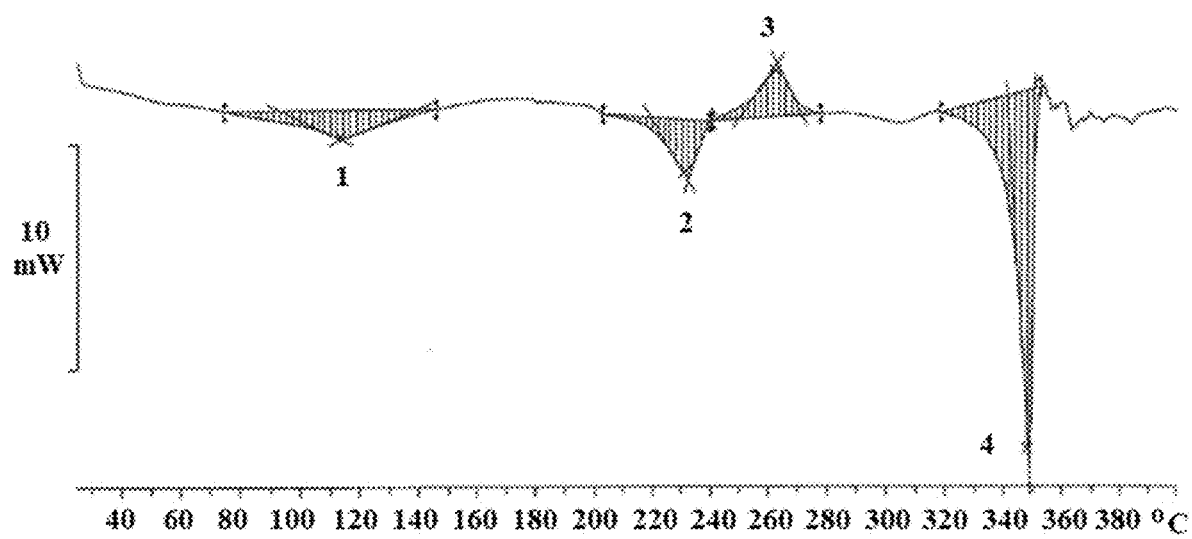
FIG. 21 is the DSC data from a representative batch of Form B material. The DSC data was collected by increasing the temperature of the sample (3.9 mg) from 25-400° C. at a rate of 10° C./minute. Endotherms were observed at 113° C. (1), 231° C. (2), 262° C. (3), and 348° C. (4). Endotherm 1 (integral=−237 mJ; normalized=−60 J/g) exhibited an onset of 113° C. and an endset of 140° C. Endotherm 2 (integral=−182 mJ; normalized=−46 J/g) exhibited an onset of 219° C. and an endset of 239° C. Endotherm 3 (integral=177 mJ; normalized=45 J/g) exhibited an onset of 250° C. and an endset of 271° C. Endotherm 4 (integral=−728 mJ; normalized=−186 J/g) exhibited an onset of 341° C. and an endset of 350° C. The x-axis is temperature measured in Celsius and the y-axis the heat flow measured in milli Watts (mW).
Figure 22:
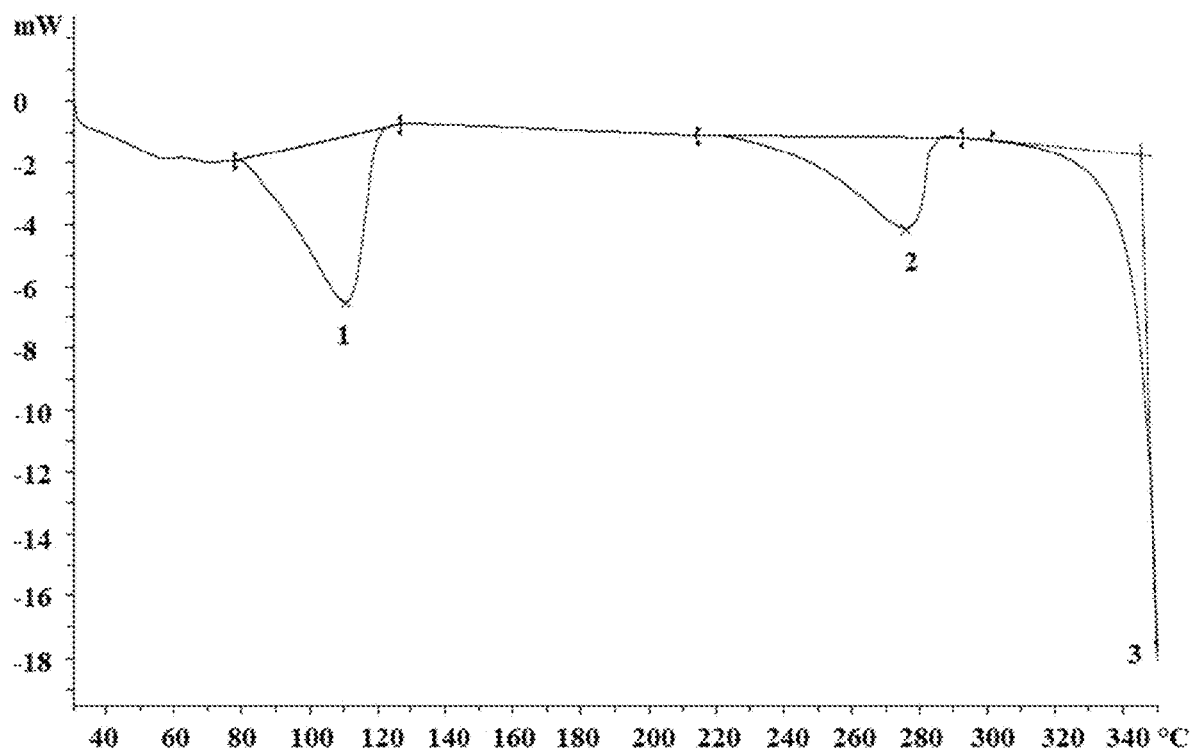
FIG. 22 is the DSC data from a representative batch of Form A. The DSC data was collected by increasing the temperature of the sample (4.4 mg) from 30-350° C. at a rate of 10° C./minute. Endotherms were observed at 110° C. (1), 275° C. (2), and 344° C. (3). Endotherm 1 (integral=−670 mJ; normalized=−151 J/g) exhibited an onset of 84° C. Endotherm 2 (integral=−480 mJ; normalized=−108 J/g) exhibited an onset of 242° C. Endotherm 3 exhibited an onset of 344° C. The x-axis is temperature measured in Celsius and the y-axis the heat flow measured in milli Watts (mW).
Figure 23:
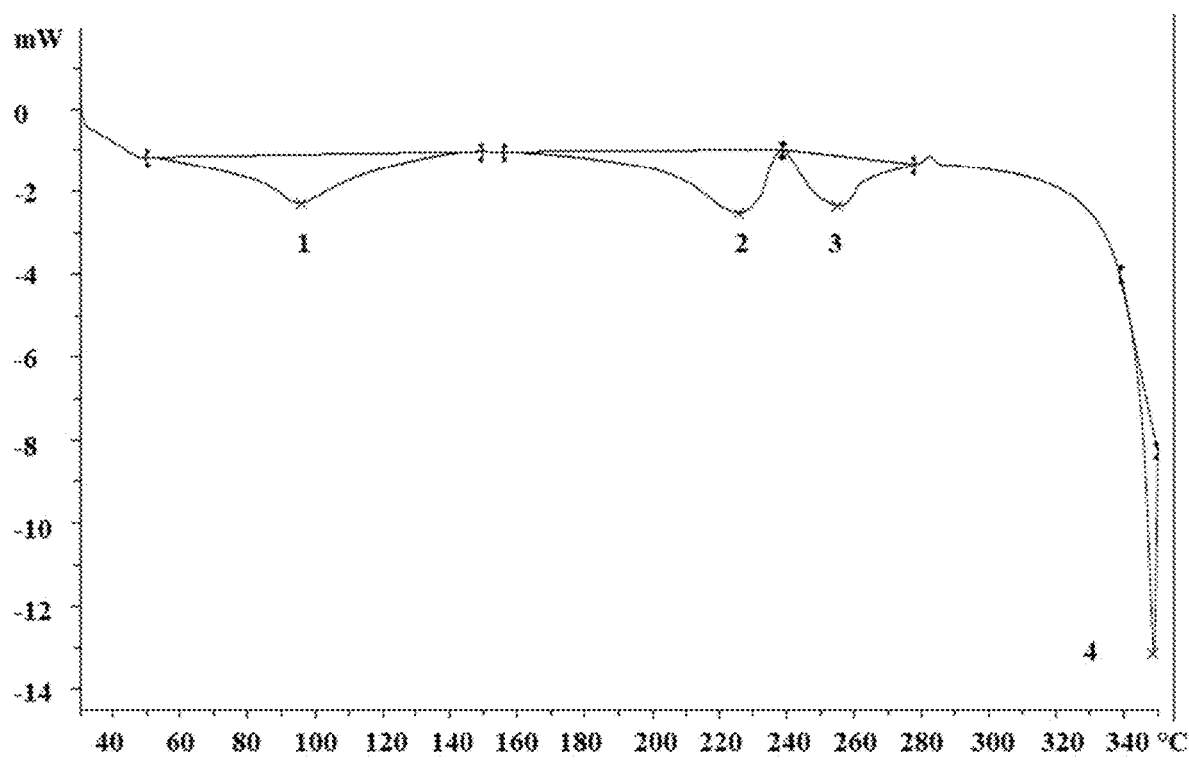
FIG. 23 is the DSC data from a representative batch of Form B. The DSC data was collected by increasing the temperature of the sample (2.6 mg) from 30-350° C. at a rate of 10° C./minute. Endotherms were observed at 95° C. (1), 225° C. (2), 254° C. (3), and 348° C. (4). Endotherm 1 (integral=−256 mJ; normalized=−97 J/g) exhibited an onset of 75° C. Endotherm 2 (integral=−265 mJ; normalized=−101 J/g) exhibited an onset of 199° C. Endotherm 3 (integral=−140 mJ; normalized=−53 J/g) exhibited an onset of 239° C. Endotherm 4 (integral=−94 mJ; normalized=−36 J/g) exhibited an onset of 344° C. The x-axis is temperature measured in Celsius and the y-axis the heat flow measured in milli Watts (mW).
Figure 24:
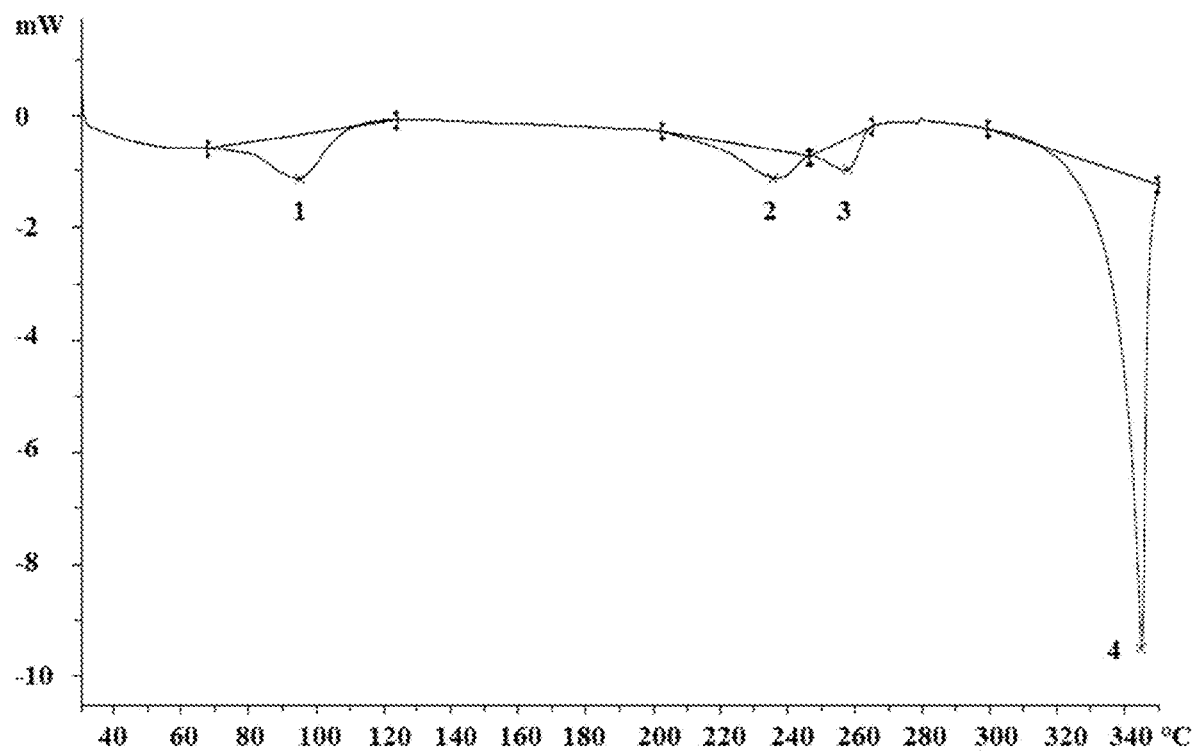
FIG. 24 is the DSC data from a representative batch of Form C. The DSC data was collected by increasing the temperature of the sample (2.5 mg) from 30-350° C. at a rate of 10° C./minute. Endotherms were observed at 95° C. (1), 235° C. (2), 257° C. (3), and 344° C. (4). Endotherm 1 (integral=−88 mJ; normalized=−36 J/g) exhibited an onset of 77° C. Endotherm 2 (integral=−58 mJ; normalized=−23 J/g) exhibited an onset of 216° C. Endotherm 3 (integral=−31 mJ; normalized=−12 J/g) exhibited an onset of 247° C. Endotherm 4 (integral=−379 mJ; normalized=−154 J/g) exhibited an onset of 338° C. The x-axis is temperature measured in Celsius and the y-axis the heat flow measured in milli Watts (mW).
Figure 25:
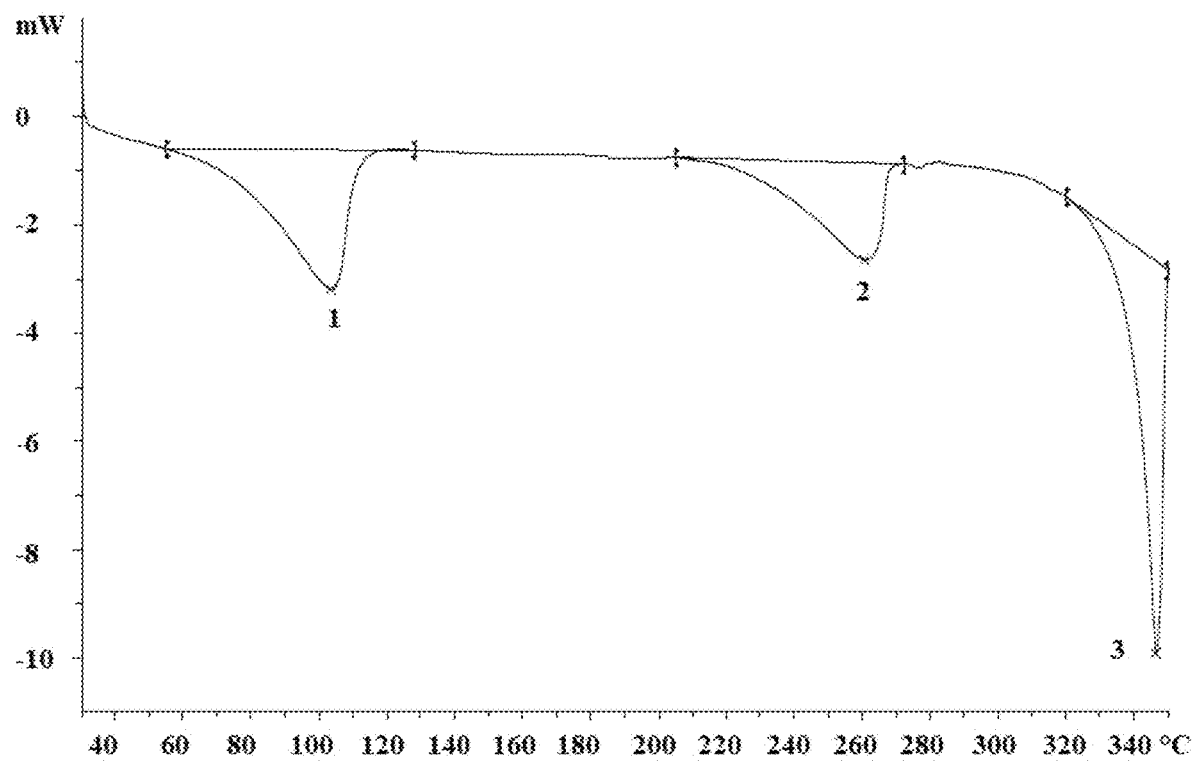
FIG. 25 is the DSC data from a representative batch of Form D. The DSC data was collected by increasing the temperature of the sample (2.5 mg) from 30-350° C. at a rate of 10° C./minute. Endotherms were observed at 103° C. (1), 260° C. (2) and 345° C. (3). Endotherm 1 (integral=−370 mJ; normalized=−149 J/g) exhibited an onset of 73° C. Endotherm 2 (integral=−271 mJ; normalized=−109 J/g) exhibited an onset of 228° C. Endotherm 3 (integral=−321 mJ; normalized=−129 J/g) exhibited an onset of 340° C. The x-axis is temperature measured in Celsius and the y-axis the heat flow measured in milli Watts (mW).
Figure 26:
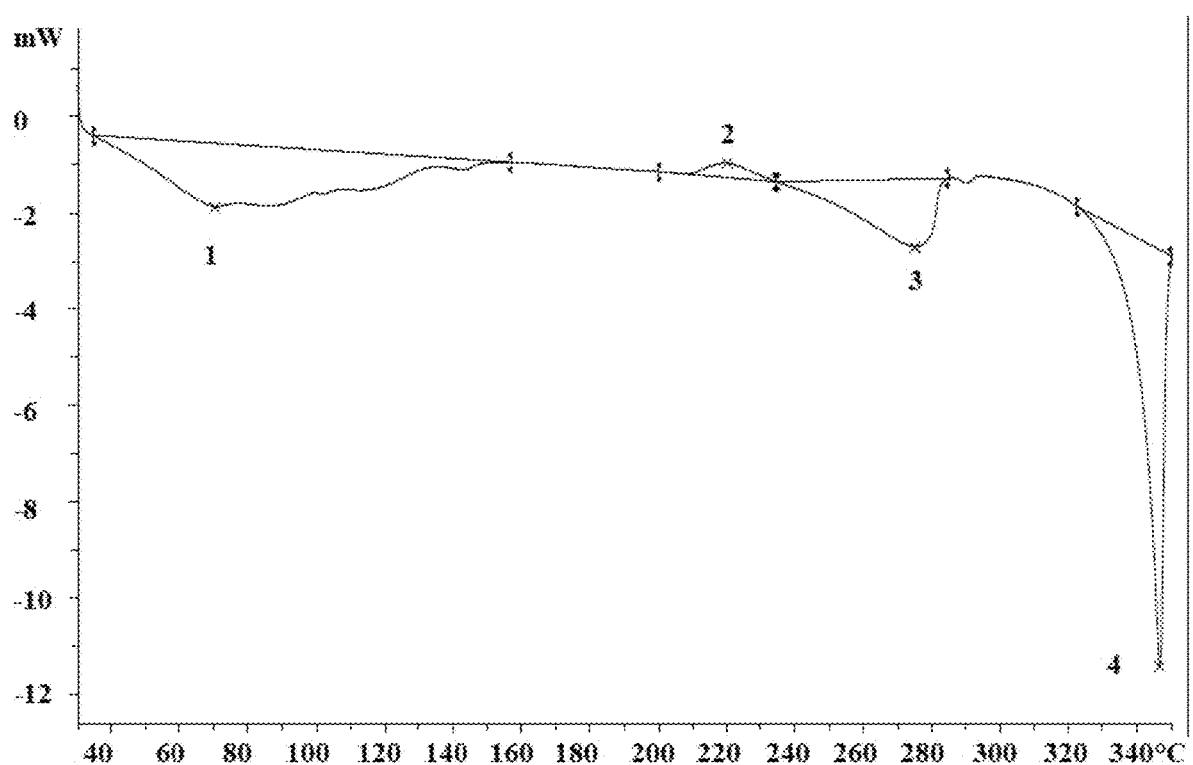
FIG. 26 is the DSC data from a representative batch of Form E. The DSC data was collected by increasing the temperature of the sample (2.5 mg) from 30-350° C. at a rate of 10° C./minute. Endotherms were observed at 70° C. (1), 219° C. (2), 275° C. (3), and 345° C. (4). Endotherm 1 (integral=−495 mJ; normalized=−194 J/g) exhibited an onset of 38° C. Endotherm 2 (integral=25 mJ; normalized=10 J/g) exhibited an onset of 209° C. Endotherm 3 (integral=−208 mJ; normalized=−81 J/g) exhibited an onset of 242° C. Endotherm 4 (integral=−339 mJ; normalized=−133 J/g) exhibited an onset of 340° C. The x-axis is temperature measured in Celsius and the y-axis the heat flow measured in milli Watts (mW).
Figure 27:
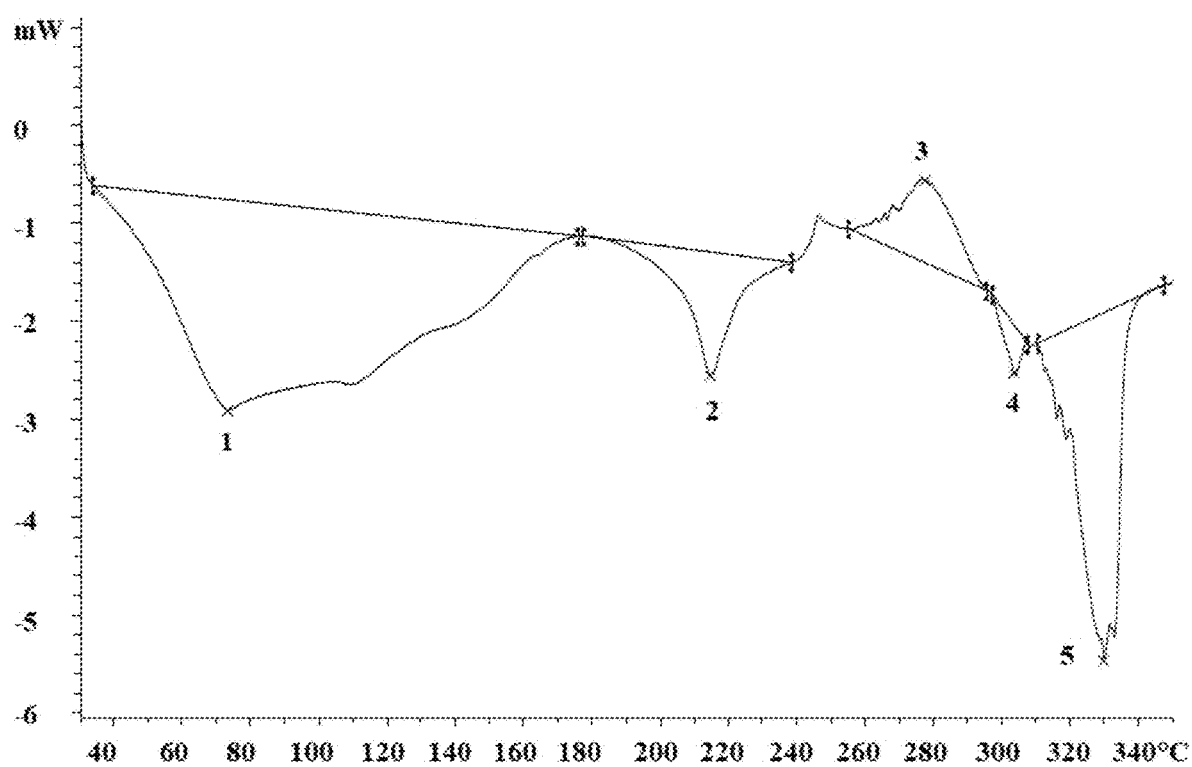
FIG. 27 is the DSC data from a representative batch of Form F. The DSC data was collected by increasing the temperature of the sample (3.0 mg) from 30-350° C. at a rate of 10° C./minute. Endotherms were observed at 73° C. (1), 214° C. (2), 277° C. (3), 303° C. (4), and 329° C. (5). Endotherm 1 (integral=−991 mJ; normalized=−323 J/g) exhibited an onset of 43° C. Endotherm 2 (integral=−121 mJ; normalized=−39 J/g) exhibited an onset of 205° C. Endotherm 3 (integral=98 mJ; normalized=32 J/g) exhibited an onset of 265° C. Endotherm 4 (integral=−15 mJ; normalized=−5 J/g) exhibited an onset of 297° C. Endotherm 5 (integral=−283 mJ; normalized=−92 J/g) exhibited an onset of 318° C. The x-axis is temperature measured in Celsius and the y-axis the heat flow measured in milli Watts (mW).
Figure 28:
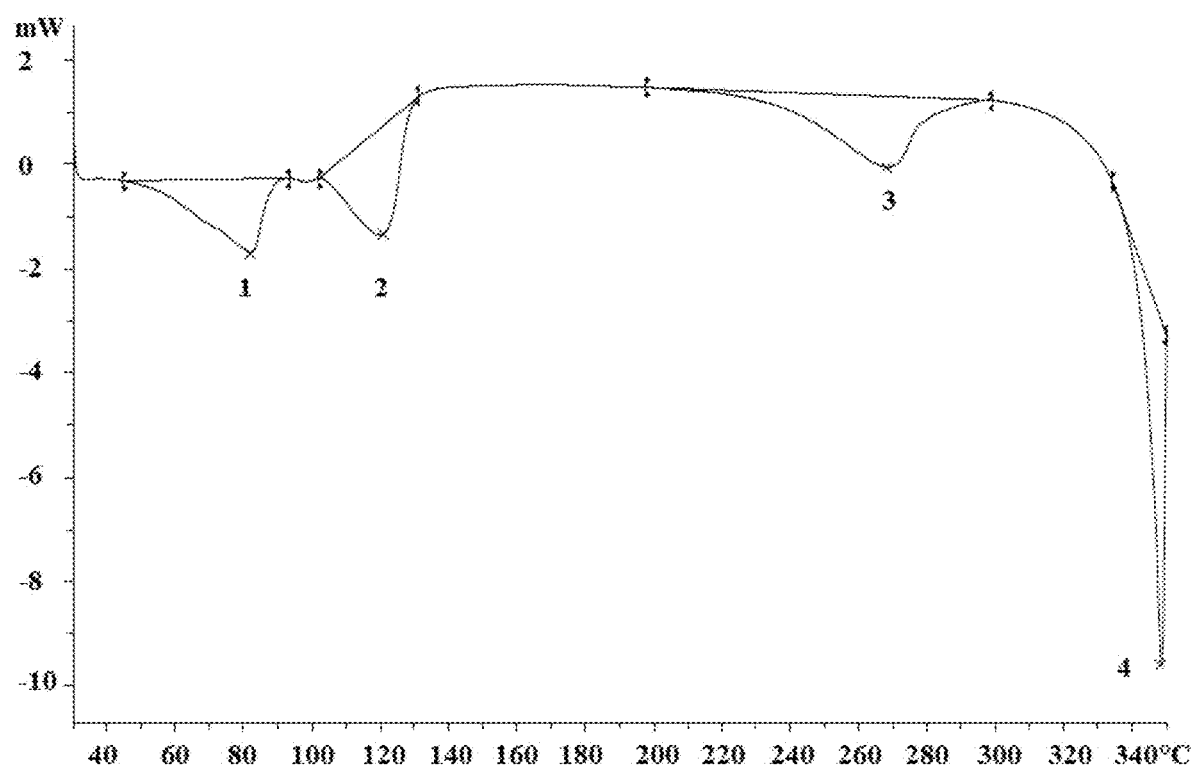
FIG. 28 is the DSC data from a representative batch of Form G. The DSC data was collected by increasing the temperature of the sample (2.8 mg) from 30-350° C. at a rate of 10° C./minute. Endotherms were observed at 81° C. (1), 120° C. (2), 260° C. (3), and 347° C. (4). Endotherm 1 (integral=−167 mJ; normalized=−59 J/g) exhibited an onset of 56° C. Endotherm 2 (integral=−183 mJ; normalized=−65 J/g) exhibited an onset of 103° C. Endotherm 3 (integral=−251 mJ; normalized=−89 J/g) exhibited an onset of 235° C. Endotherm 4 (integral=−164 mJ; normalized=−58 J/g) exhibited an onset of 344° C. The x-axis is temperature measured in Celsius and the y-axis the heat flow measured in milli Watts (mW).
Figure 29:
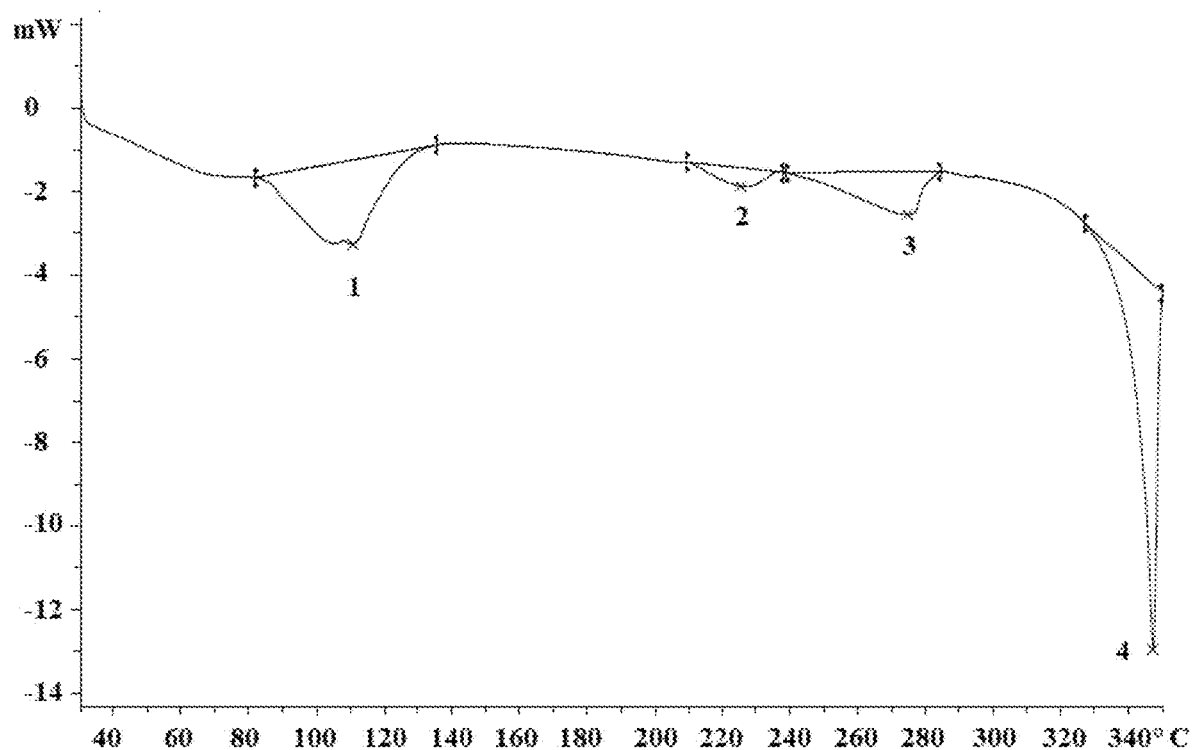
FIG. 29 is the DSC data from a representative batch of Form H. The DSC data was collected by increasing the temperature of the sample (2.7 mg) from 30-350° C. at a rate of 10° C./minute. Endotherms were observed at 110° C. (1), 225° C. (2), 274° C. (3), and 346° C. (4). Endotherm 1 (integral=−300 mJ; normalized=−110 J/g) exhibited an onset of 109° C. Endotherm 2 (integral=−41 mJ; normalized=−15 J/g) exhibited an onset of 210° C. Endotherm 3 (integral=−138 mJ; normalized=−50 J/g) exhibited an onset of 242° C. Endotherm 4 (integral=−301 mJ; normalized=−110 J/g) exhibited an onset of 346° C. The x-axis is temperature measured in Celsius and the y-axis the heat flow measured in milli Watts (mW).
Figure 30:
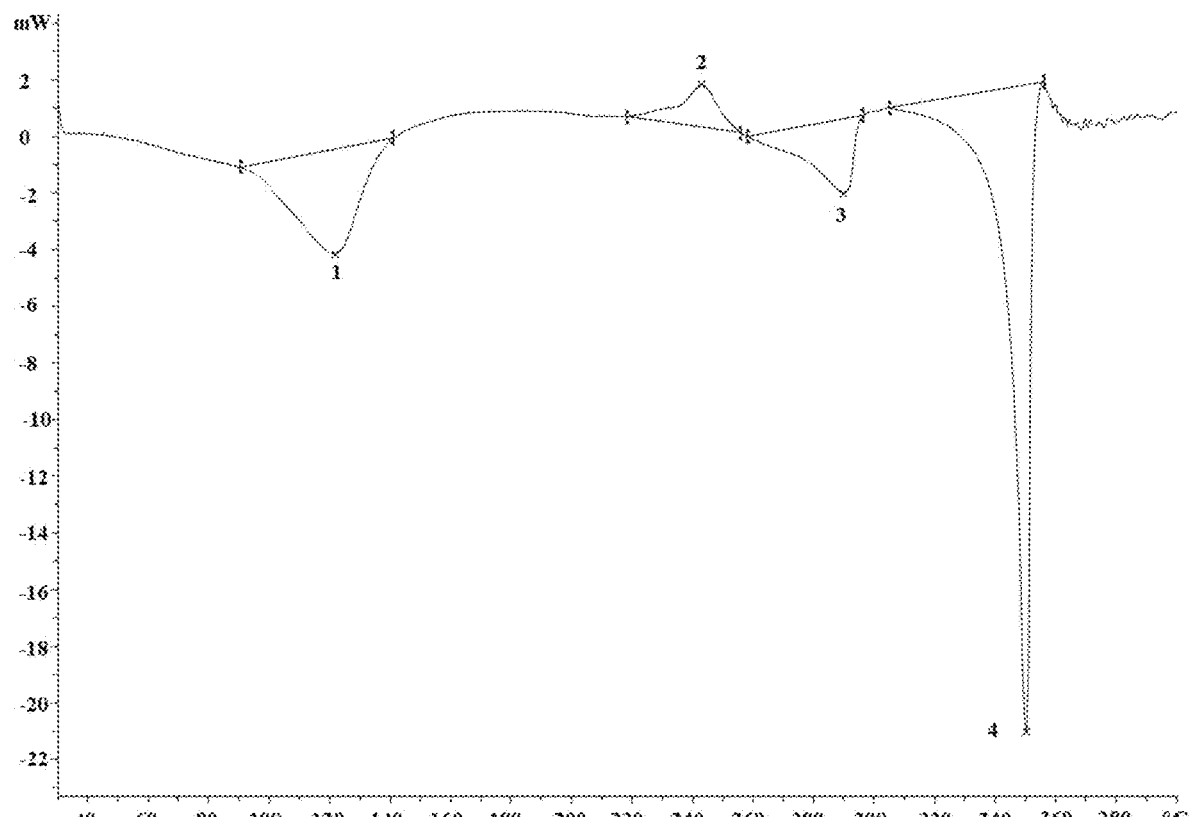
FIG. 30 is the DSC data from a representative batch of Form A. The DSC data was collected by increasing the temperature of the sample (6.0 mg) from 30-350° C. at a rate of 10° C./minute. Endotherms were observed at 121° C. (1), 242° C. (2), 290° C. (3), and 348° C. (4). Endotherm 1 (integral=−541 mJ; normalized=−90 J/g) exhibited an onset of 93° C. Endotherm 2 (integral=133 mJ; normalized=22 J/g) exhibited an onset of 233° C. Endotherm 3 (integral=−272 mJ; normalized=−45 J/g) exhibited an onset of 268° C. Endotherm 4 (integral=−1131 mJ; normalized=−198 J/g) exhibited an onset of 344° C. The x-axis is temperature measured in Celsius and the y-axis the heat flow measured in milli Watts (mW).
Figure 31:
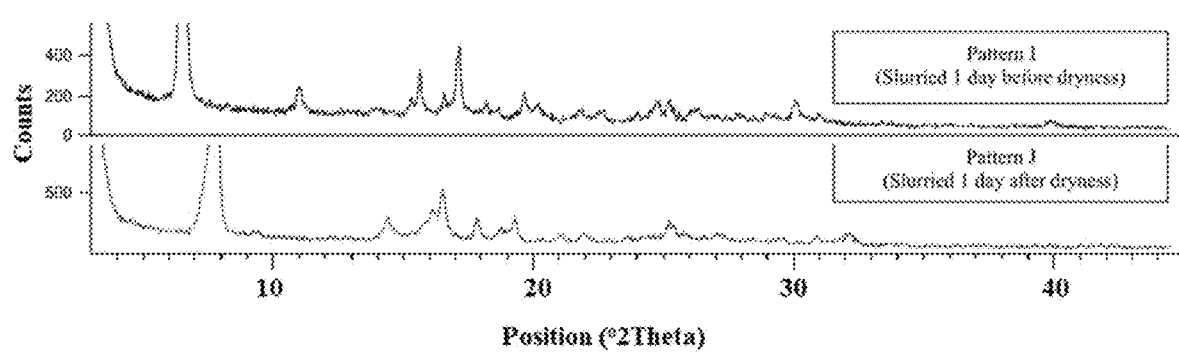
FIG. 31 is the XRPD pattern for Form I and Form J. The x-axis is 2Theta measured in degrees and the y-axis is intensity measured in counts.

The TGA data of the converted batch, Form B showed 7.5% weight loss between 31 and 120° C. (FIG. 19).

TABLE 16

Results of XRPD Analysis and TG Analysis during Conversion of Compound 2 to Form B

| Point in Conversion | Analytical Technique | Result |
|---|---|---|
| 125 mg/mL Slurry, 30° C., 20 h | XRPD | Form B + small broad peak at 4.0 °2θ |
| 125 mg/mL Slurry, 30° C., 24 h | XRPD | B + broad peaks at 4.2 °2θ and 5.7 °2θ |
| 125 mg/mL Slurry, 30° C., 42 h | XRPD | Form B |
| 125 mg/mL Slurry, 30° C., 43 h VF, washed with 50 mL of H₂O:acetone 1:2 Air-dried for 3.5 h | XRPD TGA | Form B 10% weight loss at 26-120° C. |
| Vacuum drying, 22° C., 0.5 h, 15 in Hg Vacuum drying, 22° C. 1.5 h, 27-28 in Hg | XRPD TGA | Form B 9.9% weight loss at 26-120° C. |
| Vacuum drying, 22° C., 2.0 h, 27 in Hg | XRPD TGA | Form B 7.5% weight loss at 31-120° C. |

We claim:

1. An isolated crystalline Form B of the di-HCl salt of structure:

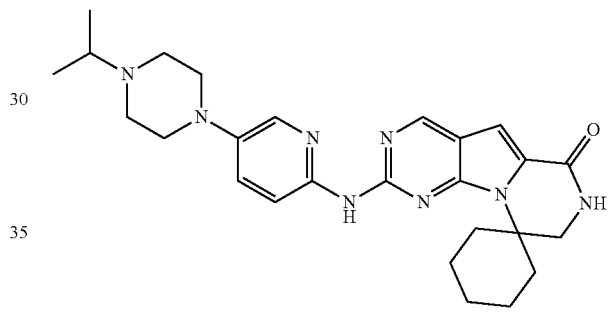

characterized by an X-ray powder diffraction (XRPD) pattern comprising at least three 2θ values selected from 6.5±0.2°, 9.5±0.4°, 14.0±0.2°, 14.4±0.2°, 18.1±0.2°, 19.3±0.2°, 19.9±0.2°, and 22.4±0.2°.

2. The isolated crystalline Form B of claim 1, wherein the XRPD pattern comprises at least four 2θ values selected from 6.5±0.2°, 9.5±0.4°, 14.0±0.2°, 14.4±0.2°, 18.1±0.2°, 19.3±0.2°, 19.9±0.2°, and 22.4±0.2°.

3. The isolated crystalline Form B of claim 1, wherein the XRPD pattern comprises at least the 2θ value of 9.5±0.4°.

4. The isolated crystalline Form B of claim 1, wherein the XRPD pattern comprises at least a 2θ value of 9.5±0.2°.

5. The isolated crystalline Form B of claim 1, wherein the XRPD pattern comprises at least the 2θ value of 19.3±0.2°.

6. The isolated crystalline Form B of claim 1, wherein the XRPD pattern comprises at least the 2θ value of 22.4±0.2°.

7. The isolated crystalline Form B of claim 1, characterized by an XRPD pattern having the characteristic 2θ values of FIG. 7.

8. The isolated crystalline Form B of claim 1 characterized by differential scanning calorimetry (DSC) onset endotherms of about 105±20° C., about 220±20° C., and about 350±20° C.

9. The isolated crystalline Form B of claim 1 characterized by differential scanning calorimetry (DSC) onset endotherms of about 105±10° C., about 220±10° C., and about 350±10° C.

10. A pharmaceutical composition comprising the isolated crystalline Form B of claim 1 and a pharmaceutically acceptable excipient for solid dosage delivery.

11. A process for producing crystalline Form B of 2'-((5-(4-isopropylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one di-HCl salt comprising the steps of
- (i) heating the free base of 2'-((5-(4-isopropylpiperazin-1-yl)pyridin-2-yl)amino)-7',8'-dihydro-6'H-spiro[cyclohexane-1,9'-pyrazino[1',2': 1,5]pyrrolo[2,3-d]pyrimidin]-6'-one in aqueous HCl to at least about 45° C.;
- (ii) stirring the solution for at least about 15 minutes and filtering the resulting solution;
- (iii) adding solvent at a temperature of at least about 45° C. and stirring the solution for at least about 15 minutes;
- (iv) decreasing the temperature of the solution to about 25° C. or lower and stirring the solution for at least about 30 minutes; and
- (v) filtering the solution and washing the solution with additional solvent to afford the crystalline Form B of 2'-((5-(4-isopropylpiperazin-1-yl)pyridin-2-yl)amino)-7',8'-dihydro-6'H-spiro[cyclohexane-1,9'-pyrazino[1',2': 1,5]pyrrolo[2,3-d]pyrimidin]-6'-one di-HCl salt;

wherein crystalline Form B of 2'-((5-(4-isopropylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one di-HCl is characterized by an X-ray powder diffraction (XRPD) pattern comprising at least three 2θ values selected from 6.5±0.2°, 9.5±0.4°, 14.0±0.2°, 14.4±0.2°, 18.1±0.2°, 19.3±0.2°, 19.9±0.2°, and 22.4±0.2°.

12. The process of claim 11, wherein the solvent used is acetone.

13. The process of claim 11, wherein the solution is stirred for about 45 minutes in step (ii).

14. The process of claim 11, wherein the solution is heated to at least about 50° C. in step (i).

15. The process of claim 11, wherein the solution is heated to about 55° C. in step (i).

16. The process of claim 11, wherein the solvent is heated to at least about 50° C. in step (iii).

17. The process of claim 11, wherein the solution is stirred for at least about 1 hour in step (iii).

18. The process of claim 11, wherein the solution is stirred for at least about 1 hour in step (iv).

19. The process of claim 11, wherein the solution is stirred for at least about 2 hours in step (iv).

20. The isolated crystalline Form B of claim 1, wherein the isolated crystalline Form B is a hydrate.

* * * * *